United States Patent
Schwarz et al.

(12) 
(10) Patent No.: US 10,556,122 B1
(45) Date of Patent: Feb. 11, 2020

(54) AESTHETIC METHOD OF BIOLOGICAL STRUCTURE TREATMENT BY MAGNETIC FIELD

(71) Applicant: BTL Medical Technologies S.R.O., Prague (CZ)

(72) Inventors: Tomás Schwarz, Prague (CZ); Ondra Prouza, Ricany u Prahy (CZ)

(73) Assignee: BTL Medical Technologies S.R.O., Prague (CZ)

( * ) Notice: Subject to any disclaimer, the term of this patent is extended or adjusted under 35 U.S.C. 154(b) by 0 days.

(21) Appl. No.: 16/266,494

(22) Filed: Feb. 4, 2019

Related U.S. Application Data

(63) Continuation-in-part of application No. 15/601,719, filed on May 22, 2017.

(60) Provisional application No. 62/357,679, filed on Jul. 1, 2016, provisional application No. 62/440,905, filed on Dec. 30, 2016, provisional application No. 62/440,922, filed on Dec. 30, 2016, provisional application No. 62/786,731, filed on Dec. 31, 2018.

(51) Int. Cl.
| | |
|---|---|
| *A61N 2/02* | (2006.01) |
| *A61F 7/00* | (2006.01) |
| *A61N 2/00* | (2006.01) |
| *A61F 7/02* | (2006.01) |

(52) U.S. Cl.
CPC ............... *A61N 2/02* (2013.01); *A61F 7/007* (2013.01); *A61F 7/0053* (2013.01); *A61N 2/004* (2013.01); *A61F 2007/0056* (2013.01); *A61F 2007/0075* (2013.01); *A61F 2007/029* (2013.01)

(58) Field of Classification Search
CPC .......... A61N 2/00; A61N 2/002; A61N 2/004; A61N 2/02; A61N 1/40; A61N 1/403; A61F 7/007; A61F 2007/0029; A61F 2007/0052; A61F 2007/0056; A61F 2007/0075
See application file for complete search history.

(56) References Cited

U.S. PATENT DOCUMENTS

| | | | |
|---|---|---|---|
| 3,658,051 | A | 4/1972 | MacLean et al. |
| 3,915,151 | A | 10/1975 | Kraus et al. |
| 4,237,898 | A | 12/1980 | Whalley |
| 4,454,883 | A | 6/1984 | Fellus |
| 4,456,001 | A | 6/1984 | Pescatore |
| 4,674,505 | A | 6/1987 | Pauli et al. |
| 4,850,959 | A * | 7/1989 | Findl ............... A61B 5/14532 604/14 |

(Continued)

FOREIGN PATENT DOCUMENTS

| | | |
|---|---|---|
| CN | 201906360 U | 7/2011 |
| DE | 1118902 B | 12/1961 |

(Continued)

OTHER PUBLICATIONS

Magneticky Stimulator DuoMAG, Alien Technik User Manuel, Jun. 26, 2012, 24 pages, Version 2.1.

(Continued)

*Primary Examiner* — Carrie R Dorna
(74) *Attorney, Agent, or Firm* — Sterne, Kessler, Goldstein & Fox P.L.L.C.

(57) ABSTRACT

Combined methods for treating a patient using time-varying magnetic field are described. The treatment methods combine various approaches for aesthetic treatment. The methods are focused on enhancing a visual appearance of the patient.

29 Claims, 22 Drawing Sheets

(56) References Cited

U.S. PATENT DOCUMENTS

| | | | |
|---|---|---|---|
| 5,067,940 | A | 11/1991 | Liboff et al. |
| 5,718,662 | A | 2/1998 | Jalinous |
| 5,766,124 | A | 6/1998 | Polson |
| 5,782,743 | A | 7/1998 | Russell |
| 5,807,232 | A | 9/1998 | Espinoza et al. |
| 5,984,854 | A | 11/1999 | Ishikawa et al. |
| 6,063,108 | A | 5/2000 | Salansky et al. |
| 6,086,525 | A | 7/2000 | Davey et al. |
| 6,099,459 | A | 8/2000 | Jacobson |
| 6,117,066 | A | 9/2000 | Abrams et al. |
| 6,179,770 | B1 | 1/2001 | Mould |
| 6,213,933 | B1 | 4/2001 | Lin |
| 6,402,678 | B1 | 6/2002 | Fischell et al. |
| 6,418,345 | B1 | 7/2002 | Tepper et al. |
| 6,527,694 | B1 | 3/2003 | Ishikawa et al. |
| 7,520,849 | B1 | 4/2009 | Simon |
| 7,608,035 | B2 | 10/2009 | Farone |
| 7,744,523 | B2 | 6/2010 | Epstein |
| 7,946,973 | B2 | 5/2011 | Peterchev |
| 7,998,053 | B2 | 8/2011 | Aho |
| 8,979,727 | B2 | 3/2015 | Ron et al. |
| 9,586,057 | B2 | 3/2017 | Ladman et al. |
| 9,636,519 | B2 | 5/2017 | Ladman et al. |
| 9,919,161 | B2 | 3/2018 | Schwarz et al. |
| 9,937,358 | B2 | 4/2018 | Schwarz et al. |
| 10,124,187 | B2 | 11/2018 | Schwarz et al. |
| 10,245,439 | B1 | 4/2019 | Schwarz et al. |
| 2001/0031906 | A1 | 10/2001 | Ishikawa et al. |
| 2003/0158585 | A1 | 8/2003 | Burnett |
| 2006/0004244 | A1* | 1/2006 | Phillips ............ A61N 2/006 600/13 |
| 2006/0152301 | A1 | 7/2006 | Rohwedder |
| 2006/0187607 | A1 | 8/2006 | Mo |
| 2006/0287566 | A1 | 12/2006 | Zangen et al. |
| 2007/0083237 | A1* | 4/2007 | Teruel ............ A61N 2/004 607/1 |
| 2008/0249350 | A1 | 10/2008 | Marchitto et al. |
| 2008/0306325 | A1 | 12/2008 | Burnett et al. |
| 2008/0306326 | A1 | 12/2008 | Epstein |
| 2009/0018384 | A1 | 1/2009 | Boyden et al. |
| 2009/0108969 | A1 | 4/2009 | Sims et al. |
| 2010/0036368 | A1 | 2/2010 | England et al. |
| 2010/0081971 | A1 | 4/2010 | Allison |
| 2010/0087699 | A1 | 4/2010 | Peterchev |
| 2010/0121131 | A1 | 5/2010 | Mathes |
| 2010/0152522 | A1 | 6/2010 | Roth et al. |
| 2010/0160712 | A1 | 6/2010 | Burnett et al. |
| 2010/0179372 | A1 | 7/2010 | Glassman |
| 2010/0222629 | A1 | 9/2010 | Burnett et al. |
| 2010/0309689 | A1 | 12/2010 | Coulson |
| 2010/0331603 | A1 | 12/2010 | Szecsi |
| 2011/0021863 | A1 | 1/2011 | Burnett et al. |
| 2011/0077451 | A1 | 3/2011 | Marchitto et al. |
| 2011/0130618 | A1 | 6/2011 | Ron et al. |
| 2012/0053449 | A1 | 3/2012 | Moses et al. |
| 2012/0108884 | A1* | 5/2012 | Bechler ............ A61N 2/06 600/15 |
| 2012/0302821 | A1 | 11/2012 | Burnett |
| 2012/0310033 | A1* | 12/2012 | Muntermann ......... A61N 2/02 600/9 |
| 2013/0030239 | A1 | 1/2013 | Weyh et al. |
| 2013/0053620 | A1 | 2/2013 | Susedik et al. |
| 2013/0123568 | A1 | 5/2013 | Hamilton et al. |
| 2013/0123764 | A1 | 5/2013 | Zarsky et al. |
| 2013/0123765 | A1 | 5/2013 | Zarsky et al. |
| 2013/0137918 | A1* | 5/2013 | Phillips ............ A61N 2/02 600/14 |
| 2013/0150653 | A1 | 6/2013 | Borsody |
| 2013/0331637 | A1 | 12/2013 | Greff |
| 2014/0148870 | A1 | 5/2014 | Burnett |
| 2014/0330067 | A1 | 11/2014 | Jordan |
| 2014/0371515 | A1 | 12/2014 | John |
| 2015/0025299 | A1 | 1/2015 | Ron et al. |
| 2015/0123661 | A1 | 5/2015 | Yui et al. |
| 2015/0133717 | A1 | 5/2015 | Ghiron et al. |
| 2015/0157873 | A1* | 6/2015 | Sokolowski ............ A61N 2/02 600/14 |
| 2015/0216719 | A1 | 8/2015 | Debenedictis et al. |
| 2015/0328475 | A1 | 11/2015 | Kim et al. |
| 2015/0367141 | A1 | 12/2015 | Goetz et al. |
| 2016/0030763 | A1 | 2/2016 | Midorikawa et al. |
| 2016/0250494 | A1 | 9/2016 | Sakaki et al. |
| 2017/0001024 | A1 | 1/2017 | Prouza |
| 2017/0001025 | A1 | 1/2017 | Schwarz et al. |
| 2017/0001029 | A1 | 1/2017 | Pribula et al. |
| 2017/0001030 | A1 | 1/2017 | Pribula et al. |
| 2017/0072212 | A1 | 3/2017 | Ladman et al. |
| 2017/0106201 | A1 | 4/2017 | Schwarz et al. |
| 2017/0120067 | A1 | 5/2017 | Prouza |
| 2018/0001106 | A1 | 1/2018 | Schwarz |
| 2018/0125416 | A1 | 5/2018 | Schwarz et al. |
| 2018/0236254 | A1 | 8/2018 | Schwarz et al. |

FOREIGN PATENT DOCUMENTS

| | | |
|---|---|---|
| DE | 3205048 A1 | 8/1983 |
| EP | 0459401 A1 | 12/1991 |
| IE | 3610474 A | 10/1986 |
| JP | 2017/518857 A | 7/2017 |
| WO | 03/103769 A1 | 12/2003 |
| WO | 2015/179571 A1 | 11/2015 |

OTHER PUBLICATIONS

Obsluze, N.K., Uzivatelsky manual, Pristroj pro vysokoindukcni magnetickou stimulaci, typove oznaceni, Saluter Moti, 2016, 42 Pages.

Wasilewski, M.L., Academy of Aesthetic and Anti-Aging Medicine, Application of magnetic fields with deep stimulation in the fight against local obesity of lower limbs, BTL, 2012, 4 pages.

Course in Physical Therapy, Presentation, Jan. 4, 2013.

Abulhasan, J.F., et al., "Peripheral Electrical and Magnetic Stimulation to Augment Resistance Training," Journal of Functional Morphology and Kinesiology, 1(3):328-342, (2016).

Bachasson, D., et al., "Quadriceps Function Assessment Using an Incremental Test and Magnetic Neurostimulation: a Reliability Study," Journal of Electromyography and Kinesiology, 23(3):649-658, Elsevier, England, (Jun. 2013).

Barker, A.T, "An Introduction to the Basic Principles of Magnetic Nerve Stimulation," Journal of Clinical Neurophysiology, 8(1):26-37, Lippincott Williams & Wilkins, United States, (Jan. 1991).

Behrens, M., et al., "Repetitive Peripheral Magnetic Stimulation (15 Hz RPMS) of the Human Soleus Muscle did not Affect Spinal Excitability," Journal of Sports Science and Medicine, 10(1):39-44, Dept. of Sports Medicine, Medical Faculty of Uludag University, Turkey (Mar. 2011).

Beilin, G., et al., "Electromagnetic Fields Applied to the Reduction of Abdominal Obesity," Journal of Cosmetic & Laser Therapy, 14(1):24-42, Informa Healthcare, England, (Feb. 2012).

Bustamante, V., et al., "Muscle Training With Repetitive Magnetic Stimulation of the Quadriceps in Severe COPD Patients," Respiratory Medicine, 104(2):237-245, Elsevier, England, (Feb. 2010).

Bustamante, V., et al., "Redox Balance Following Magnetic Stimulation Training in the Quadriceps of Patients With Severe COPD," Free Radical Research, 42(11-12):939-948, Informa Healthcare, England, (Nov. 2008).

Caress, J.B., et al., "A Novel Method of Inducing Muscle Cramps Using Repetitive Magnetic Stimulation," Muscle Nerve, 23(1):126-128, John Wiley & Sons, United States, (Jan. 2000).

Increasing Physiotherapy Presence in Cosmetology, Spa Inspirations, Jan. 2012, pp. 34-35.

CR Technology, Salus-Talent, Technical File of Electro-magnetic Stimulator, Document No. TF-005, 2008, 241 pages.

CR Technology, Technology for Health and Business for Human Being, investor relations, 2008, 21 pages.

Effective PEMF Magnetic Fat Reduction Slimming Body Beauty Salon Machine (PEMF Star), Wolfbeauty 1980, PEMF Star, China,

(56) References Cited

OTHER PUBLICATIONS

Retrieved from the Internet: (URL: https://www.ec21.com/product-details/Effective-PEMF-Magnetic-Fat-Reduction--8928746.html), 2019, 5 pages.

Goetz, S.M., et al., "Coil Design for Neuromuscular Magnetic Stimulation Based on a Detailed 3-D Thigh Model," IEEE Transactions on Magnetics, 50(6):10, IEEE, (Jun. 2014).

Gorodnichev, R.M., "Magnetic Stimulation of Muscles as New Method to Enhance Their Strength," Velikie Luki State Academy of Physical Culture and Sport, Velikie Luki, 2016, 5 pages.

Hamnegard, C.H., et al., "Quadriceps Strength Assessed by Magnetic Stimulation of the Femoral Nerve in Normal Subjects," Clinical Physiology and Functional Imaging, 24(5):276-280, Blackwell, England, (Sep. 2004).

Han, T.R., et al., "Magnetic Stimulation of the Quadriceps Femoris Muscle: Comparison of Pain With Electrical Stimulation," American Journal of Physical Medicine & Rehabilitation, 85(7):593-599, Lippincott Williams & Wilkins, United States, (Jul. 2006).

Iskra Medical, Magneto System, 2012, 2 pages.

Katuscakova, Z.L., et al., High Induction magnet therapy in rehabilitation, Department of Physiactric Rehabilitation, 2012, 36 pages.

Lampropoulou, S.I., et al., "Magnetic Versus Electrical Stimulation in the Interpolation Twitch Technique of Elbow Flexors," Journal of Sports Science and Medicine, 11(4):709-718, Dept. of Sports Medicine, Medical Faculty of Uludag University, Turkey (Dec. 2012).

Lin, V.W., et al., "Functional Magnetic Stimulation for Restoring Cough in Patients With Tetraplegia," Archives of Physical Medicine and Rehabilitation, 79(5):517-522, W.B. Saunders, United States, (May 1998).

Lin, V.W., et al., "Functional Magnetic Stimulation of Expiratory Muscles: a Noninvasive and New Method for Restoring Cough," Journal of Applied Physiology (1985), 84(4):1144-1150, American Physiological Society, United States, (Apr. 1998).

Madariaga, V.B., et al., "[Magnetic Stimulation of the Quadriceps: Analysis of 2 Stimulators Used for Diagnostic and Therapeutic Applications]," Archivos De Bronconeumologia, 43(7):411-417, Elsevier Espana, Spain, (Jul. 2007).

Mag Venture, Magnetic Stimulation, Accessories Catalogue, Accessories Catalogue, 2011, 54 pages.

MagVenture, MagPro® by MagVenture®, Versatility in Magnetic Stimulation, World Leading Transcranial Magnetic Stimulation Systems, 2011, 9 Pages.

Neuro Star, TMS Therapy, Bringing Hope to Patients with Depression, 2013, 6 Pages.

Neurosoft, Ivanovo, Since 1992, Magnetic Stimulator, NEURO-MS, Technical Manual, Neurosoft Ltd, Ivanovo, Russia, 2006, 67 Pages.

Nexstim NBS System, Navigated Brain Stimulation, Noninvasive, direct cortical mapping, 2012, 5 Pages.

Operating Manual: Magstim D70$^2$ Coil, MOP06-EN, Revision 01, The Magstim Company Limited, Feb. 2012, 14 Pages.

Operating Manual: Magstim Magstim 200$^2$, MOP01-EN, Revision 01, The Magstim Company Limited, Sep. 2011, 25 Pages.

Operating Manual: Magstim, Magstim Alpha Coil Range, MOP11-EN, Revision 01, Oct. 2012, 18 Pages.

Operating Manual: Magstim, Magstim Bistim$^2$, MOP02-EN, Revision, The Magstim Company Limited, 01, Sep. 2011, 27 Pages.

Operating Manual, Magstim, Model 200, P/N 3001-01, Double 70mm, Remote Coil, P/N 3190-00, The Magstim Company Limited, 2006, 32 pages.

Operating Manual: Magstim R, 2nd, Generation Coil Family, 3100-23-02, Magstim Coils, The Magstim Company Limited, Nov. 2002, 14 Pages.

Operating Manual, Magstim R Air-Cooled Double 70mm Coil System, 1600-23-04, The Magstim Company Limited, 18 Pages.

Operating Manual: Magstim R, Bistim System, P/N 3234-23-01, The Magstim Company Limited, Nov. 2004, 30 Pages.

Operating Manual: Magstim R, Coils & Accessories, 1623-23-07, Magstim Coils & Accessories, May 2010, 24 Pages.

Operating Manual: MAGSTIM, RAPID2, P/N 3576-23-09, The MAGSTIM Company Ltd, Nov. 2009, 61 Pages.

Operator'S Manual: BTL EMSCULPT, BTL Industries Ltd, United Kingdom, 2018, 35 pages.

Operator'S Manual: BTL, HPM-6000U, BTL Industries Ltd, United Kingdom, Dec. 2016, 36 pages.

Papimi, For Scientific Research, Pap Ion Magnetic Inductor, Presentation, Magnetotherapeutic Device, Nov. 2009, 61 Pages.

Podebradsky.K., et al., Clinical study of high-induction electromagnetic stimulator SALUS talent, 2010, 8 pages.

Polkey M.I., et al., "Functional Magnetic Stimulation of the Abdominal Muscles in Humans," American Journal of Respiratory and Critical Care Medicine, 160(2):513-522, American Thoracic Society, United States (Aug. 1999).

Polkey, M.I., et al., "Quadriceps Strength and Fatigue Assessed by Magnetic Stimulation of the Femoral Nerve in Man," Muscle Nerve, 19(5):549-555, John Wiley & Sons, United States, (May 1996).

Quick Start Manuals, MAGSTIM Super Rapid Plus Quick Start, Aalto TMS Laboratory, Aalto School of Science, 2013, 7 Pages.

Salus Talent-A, REMED, User Guide, High Intensity Electro Magnetic Field Therapy, 2017, 37 pages.

Szecsi, J., et al., "A Comparison of Functional Electrical and Magnetic Stimulation for Propelled Cycling of Paretic Patients," Archives of Physical Medicine and Rehabilitation, 90(4):564-570, W.B. Saunders, United States, (Apr. 2009).

Szecsi, J., et al., "Force-pain Relationship in Functional Magnetic and Electrical Stimulation of Subjects With Paresis and Preserved Sensation," Clinical Neurophysiology, 121(9):1589-1597, Elsevier, Netherlands, (Sep. 2010).

Taylor, J.L, "Magnetic Muscle Stimulation Produces Fatigue Without Effort," Journal of Applied Physiology (1985), 103(3):733-734, American Physiological Society, United States, (Sep. 2007).

Tesla Stym, Iskra Medical, Tone the inner muscle with FMS Functional Magnetic Stimulation, 2013, 4 pages.

User Guide: Mag Venture, Magpro family, MagPro R30, MagPro R30 with MagOption, MagPro X100, MagPro X100 with MagOption, MagPro software v.5.0, US-edition, MagPro family User Guide, 2010, 52 Pages.

User Guide, Salus Talent Pro, REMED, High Intensity Electro magnetic Field Therapy-2 Channel, 2017, Version M-1.0.0, 45 pages.

User Guide, Salus Talent, REMED, High Intensity Electro magnetic Field Therapy, Version. 1.0.0, 2017, 40 pages.

User'S Manual: BTL-6000, Super Inductive System Elite, BBTL Industries Ltd, United Kingdom, Sep. 2016, 36 pages.

User Manual: Electro-magnetic Stimulator, Salus-Talent, Version 1.00, Rehabilitation Medical Company, 2013, 34 Pages.

User Manual: Regenetron Pro, System Information, Regenetron Pro User Manual, Nov. 2014, 7 Pages.

Verges S., et al., "Comparison of Electrical and Magnetic Stimulations to Assess Quadriceps Muscle Function," Journal of Applied Physiology (1985), 106(2):701-710, American Physiological Society, United States, (Feb. 2009).

\* cited by examiner

AESTHETIC METHOD OF BIOLOGICAL STRUCTURE TREATMENT BY MAGNETIC FIELD

CROSS-REFERENCE RELATED APPLICATIONS

This Application is a Continuation-in-Part of U.S. patent application Ser. No. 15/601,719, filed May 22, 2017, now pending; which claims priority to U.S. Provisional Patent Application Nos. 62/357,679 filed Jul. 1, 2016; 62/440,905 filed Dec. 30, 2016; and 62/440,922 filed Dec. 30, 2016. These applications are incorporated herein by reference.

This Application further claims priority to U.S. Provisional Patent Application No. 62/786,731, filed Dec. 31, 2018.

FIELD OF THE INVENTION

The present invention generally relates to device and methods using the influence of magnetic and induced electric field on biological structure. The magnetic field is time-varying and high powered therefore the method is based on a value of magnetic flux density sufficient to induce at least muscle contraction. The invention proposes further to combine the magnetic field with radiofrequency, light, mechanical or pressure source in order to provide an apparatus for improved treatment.

BACKGROUND OF THE INVENTION

Aesthetic medicine includes all treatments resulting in enhancing a visual appearance and satisfaction of the patient. Patients want to minimize all imperfections including body shape and effects of natural aging. Indeed, patients request quick, non-invasive procedures providing satisfactory results with minimal risks.

The most common methods used for non-invasive aesthetic applications are based on application of mechanical waves, e.g. ultrasound or shock wave therapy; or electromagnetic waves, e.g. radiofrequency treatment or light treatment, such as intense pulsed light or laser treatment. The effect of mechanical waves on tissue is based especially on cavitation, vibration and/or heat inducing effects. The effect of applications using electromagnetic waves is based especially on heat production in the biological structure. However the currently used treatment methods are used separately.

A mechanical treatment using mechanical waves and/or pressure were used for treatment of cellulite or adipose cells. However, mechanical treatment includes several drawbacks such as risk of a panniculitis and/or non-homogenous result.

A thermal treatment is applied to the patient for enhancing a visual appearance of the skin by e.g. increasing production of collagen and/or elastin, smoothing the skin or reduction of cellulite and/or adipose cell. However, thermal treatment includes several drawbacks such as risk of overheating a patient or even causing a thermal damage to the patient, risk of a panniculitis and/or non-homogenous result.

The mechanical and/or the thermal treatment is not able to provide enhanced visual appearance of a muscle, e.g. muscle shaping, toning and/or volumization effect. Mechanical treatment and/or the thermal treatment includes several drawbacks such as risk of a panniculitis, non-homogenous result and others.

Current magnetic methods are limited in key parameters which do not allow satisfactory enhancement of visual appearance. As a result, new methods are needed to enhance the visual appearance of the patient.

Existing devices have low efficiency and they waste energy, which limits their use. Eddy currents induced within the magnetic field generating device create engineering challenges. Existing devices contain magnetic field generating devices which are made of metallic strips, electric wires or hollow conductors. Since the therapy requires large currents, significant losses are caused by induced eddy currents within the magnetic field generating device. Eddy currents lead to production of unwanted heat and therefore there is need to sufficiently cool the magnetic field generating device. Also, the energy source must be protected during reverse polarity of resonance. This requires using protective circuits which consume significant amounts of energy. Skin tissue is composed of three basic elements: epidermis, dermis and hypodermis or so called subcutis. The outer and also the thinnest layer of skin is the epidermis. The dermis consists of collagen, elastic tissue and reticular fibers. The hypodermis is the lowest layer of the skin and contains hair follicle roots, lymphatic vessels, collagen tissue, nerves and also fat forming a subcutaneous white adipose tissue (SWAT). The adipose cells create lobules which are bounded by connective tissue, fibrous septa (retinaculum cutis).

Another part of adipose tissue, so called visceral fat, is located in the peritoneal cavity and forms visceral white adipose tissue (VWAT) located between parietal peritoneum and visceral peritoneum, closely below muscle fibers adjoining the hypodermis layer.

The currently used aesthetic applications don't provide any treatment combining the effect of time-varying magnetic field treatment and an auxiliary treatment method, e.g. treatment by thermal treatment and/or mechanical treatment. The currently used thermal treatment includes many adverse events such as non-homogenous temperature distribution, panniculitis, insufficient blood and/or lymph flow during and/or after the treatment. Additionally several adverse event such as panniculitis may occur after the treatment. Further the treatment may be painful so that a topical anesthetic is recommended.

The development of new aesthetic treatment methods providing improved results in shorter time periods is needed.

SUMMARY OF THE INVENTION

The treatment methods and devices as described below produce a time varying magnetic field for patient treatment which better optimizes energy use, increases the effectiveness of the treatments and provide a new treatment. The magnetic impulses may be generated in monophasic, biphasic or polyphasic regimes. In a first aspect, the device has one or more magnetic field generating devices; a switch; an energy storage device and a connection to an energy source. The magnetic field generating device may be made of wires with a cross-section surface less than 100 cm$^2$. The magnetic field generating device may be flexibly attached in a casing of device. The casing may comprise a blower or blowers which ensure cooling of the magnetic field generating device.

The present methods provide new aesthetic applications for focused remodeling of the patient's body. The magnetic field generating device of the magnetic treatment device may be flexibly attached to casing of the device. The blower or blowers may be arranged to blow air on both sides of magnetic field generating device. Optionally, the magnetic field generating device may be a flat type magnetic field generating device.

The new magnetic treatment methods may improve a muscle of the patient. Further the new magnetic treatment method enables improved treatment results. Alternatively the magnetic treatment may provide pain relief and/or myorelaxation effect to the patient.

The method of treating a biological structure uses a combination of non-invasive methods for enhancing human appearance. The invention utilizes electromagnetic field. Methods may be used for targeted remodeling of adipose tissue, focused treatment of cellulite, body contouring, skin tightening or skin rejuvenation. The invention relates to focused heating of the target tissue by electromagnetic waves, whereas the effect of focused heating of the target tissue is amplified by the effect of a magnetic treatment.

The time-varying magnetic field induces the muscle contraction at higher repetition rates and the contraction is stronger. The treatment ma be more efficient for reducing the number and/or volume of adipocytes and enhancing the visual appearance of the treated body region via targeted muscle contraction. Further the temperature homogeneity of is improved. Additionally, strong muscle contractions at higher repetition rates cause mechanical movement of all the layers in proximity of the contracted muscle. The methods therefore cause remodeling and/or neogenesis of the collagen and elastin fibers.

The methods enable new treatments by magnetic and/or electromagnetic field. The repetition rate of the magnetic field is in the range of 1 to 300 Hz with high magnetic flux density up to 7 Tesla (equivalent to 70000 Gauss). The frequency of the electromagnetic field is 13.56 or 40.68 or 27.12 MHz or 2.45 GHz.

On the other hand, a combination with a magnetic treatment method may enhance the visual appearance of the muscle and/or other soft tissue such as skin or adipose tissue, including increase of apoptotic index.

The methods enable combined treatment using different treatment methods such as magnetic and/or auxiliary treatment methods. The combination of different treatment methods provide a complex treatment method for focused treatment of a treated body region.

The present methods provide combined treatment using influence of magnetic treatment and mechanical treatment by shock waves, ultrasound waves, acoustic waves and/or pressure application. The mechanical treatment may induce mechanical damage to the treated biological structure and/or tissues. Ultrasound waves may heat adipose cells, dermis, hypodermis or other target biological structure. Ultrasound waves may also induce a cavitation.

The present methods and devices may include a handheld applicator, for manual and precise treatment of tissue, particularly of uneven areas, and scanning unit providing automated or manual positioning of the optical spot created by the optical waves (for example light) on the tissue of a subject for homogenous treatment of large areas of tissue. In some embodiments, the handheld applicator may be connected to the scanning unit by an attaching mechanism which in turn provides the handheld applicator with optical treatment. The handheld applicator may apply optical waves onto the tissue of the subject to be scanned during treatment.

Present method and devices may also include sensors configured to measure various parameters of the scanning unit and the subject tissue. Based on the information from the at least one sensor a controller connected to scanning unit may change parameters of the optical treatment system and method, including but not limited to the optical output, the duration of treatment, the optical spot size or shape, the scanning speed or direction of movement of the optical spot, the wavelength or wavelengths of the optical waves, the frequency, or optical flux density. Such a change may provide more homogenous treatment or may protect the patient from discomfort or harm.

The present method provides combined treatment using magnetic treatment and thermal treatment. A combination of heating/cooling may cause an increase in apoptotic index, increase in muscle thickness, apoptosis and/or necrosis of the target biological structure such as adipose cells. Remodeling of the target biological structure is more significant and treatment duration is reduced. Potential risks for the patient associated with single treatment methods are avoided. Further the side effects such as swelling and/or inflammation are reduced and/or eliminated.

Although methods of the present invention may be described herein as a sequence of steps in a particular order, it is understood that, unless explicitly stated otherwise, the steps of any methods of the present invention may alternatively be performed in a different order. In some embodiments, some or all of the steps of a method of the present invention may be repeated.

DETAILED DESCRIPTION

Figure 1:
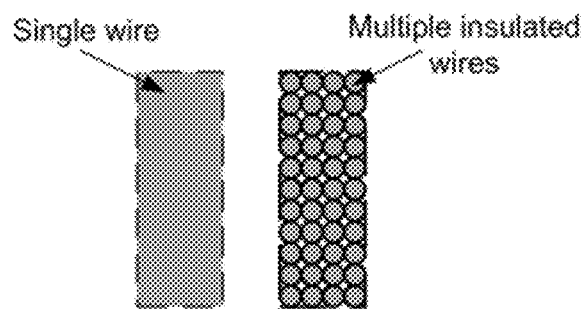
FIG. 1 is a cross section view of a magnetic field generating device winding.

It is to be understood that the figures and descriptions of the present invention have been simplified to illustrate elements that are relevant for a clear understanding of the present invention, while eliminating, for the purpose of clarity, many other elements found in related systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

As used herein, "auxiliary treatment" may refer to an additional treatment other than treatment via time-varying magnetic field. Examples of auxiliary treatments may include, but are not limited to, application of mechanical waves, e.g. acoustic wave, ultrasound or shock wave therapy; or electromagnetic waves, e.g. radiofrequency or diathermy treatment or light treatment, such as intense pulsed light or laser treatment; or mechanical treatment, e.g. positive or negative pressure, rollerball, massage etc.; or thermal treatment, e.g. cryotherapy; or electrotherapy method; or mesotherapy methods and/or any combination thereof. Auxiliary treatments may be invasive or non-invasive, or may include a combination of invasive and non-invasive treatment steps.

Individual embodiments of an auxiliary treatment may be used interchangeably herein in exemplary embodiments. Unless explicitly stated otherwise, any exemplary embodiment referring to one auxiliary treatment should be treated as a disclosure of an exemplary embodiment referring to any of the listed auxiliary treatments.

Thermal treatment may refer to treatment by heating or cooling, e.g. a cryotherapy treatment.

Mechanical treatment may refer to treatment methods using applying a pressure such as positive or negative; applying mechanical waves such as shock waves, ultrasound waves or vibration.

Biological structure may be at least one neuron, neuromuscular plate, muscle fiber, adipose cell or tissue, collagen, elastin, pigment or skin.

Remodeling target biological structure may refer to reducing the number and/or volume of the adipocytes by apoptosis and/or necrosis, cellulite treatment, body shaping and/or contouring, muscle toning, skin tightening, collagen treatment, skin rejuvenation, wrinkle removing, reducing stretchmarks, breast lifting, buttock lifting, buttock rounding, buttock firming, lip enhancement, treatment of vascular or pigmented lesions of the skin or hair removing.

Body region may include a muscle or a muscle group, buttock, saddlebag, love handle, abdomen, hip, leg, calf, thigh, arm, limb, face or chin and/or any other tissue.

Muscle may include at least one of muscle fiber, muscle tissue or group, neuromuscular plate or nerve innervating the at least one muscle fiber.

Deep muscle may refer to a muscle that is at least partly below superficial muscles and/or to the muscle covered by the thick layer of other tissue, e.g. mostly adipose tissue and/or the skin, with thickness 0.5, 1, 2, 3, 4, 5 or more centimeters.

Adipose tissue may refer to at least one lipid rich cell, e.g. adipocyte.

Bolus may refer to a layer of fluid material, e.g. water or fluid solution of ceramic particles, preferably enclosed in a flexible sac made of biocompatible material.

Impulse may refer to a magnetic stimulus, i.e. generating/applying of magnetic field causing at least one muscle contraction. The impulse may be but not limited to monophasic, polyphasic, biphasic magnetic field.

Pulse may refer to a period of treatment consisted of one impulse and time duration of a) no magnetic field applied to the patient or b) application magnetic field insufficient to cause a muscle contraction.

Repetition rate may refer to frequency of firing the pulses; it is derived from the time duration of a pulse. It equals to a frequency of switching the switch on.

The train may refer to a plurality of pulses, i.e. at least two pulses followed one by another. Train may cause multiple muscle contractions followed one by one, at least one incomplete tetanus muscle contraction or at least one complete tetanus muscle contraction.

Burst may refer to one train and a time with no magnetic field generated, or the train followed by a static magnetic field, or the train followed by a time-varying magnetic field insufficient to cause a muscle contraction; it refers to at least one muscle contraction followed by no muscle contraction and/or muscle relaxation.

Combined treatment may refer to a combination of at least two different treatment methods, e.g. application of magnetic field and one or more auxiliary treatments, application of magnetic field and thermal treatment, application of magnetic field and mechanical treatment, or application of magnetic field with thermal treatment and mechanical treatment.

Hardware panel may refer to at least one hardware component used for controlling the optical and/or magnetic treatment. The hardware panel includes at least one of input interface for inputting treatment parameters by an operator and processing unit for controlling the optical and/or magnetic treatment.

Optical waves may refer to UV radiation, visible light, IR radiation, far IR radiation. Further optical waves may be coherent and/or non-coherent, monochromatic or polychromatic.

Optical waves generating device may refer to laser or laser diode, light emitting diode (LED), electric discharge source, incandescent source, fluorescent source, luminescent source, electroluminescent source etc.

Optical treatment parameter may refer but not limited to the optical output, treatment duration, optical spot size and shape, scanning speed, direction of the movement of the optical spot, treatment pattern, a wavelength or wavelengths of the optical radiation, the frequency energy flux or the distance between the subject tissue and the scanning unit or handheld applicator.

The magnetic treatment device may include at least one magnetic field generating device. Alternatively the magnetic treatment device may include a plurality of the magnetic field generating devices. The at least one applicator may include at least one magnetic field generating device. Alternatively at least one applicator may include the plurality of the magnetic field generating devices.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

FIG. 1 illustrates an exemplary embodiment of a cross section of winding of a magnetic field generating device for a magnetic treatment device. The magnetic field generating device may be constructed from litz-wire, wherein each wire is insulated separately. Each individual conductor is coated with non-conductive material so the magnetic field generating device constitutes multiple insulated wires. Alternatively the magnetic field generating device may be made of bare wire e.g. litz-wire without insulation, or conductive tapes, conductive strips, or copper pipe with hollow inductors. The insulation of wires separately may be a substantial improvement, since it may lead to a significant reduction of the induced eddy currents. Power loss due to eddy currents, per single wire, is described by Equation 1 below. The small diameter of wires may reduce self-heating of the magnetic field generating device and therefore increase efficiency of the present magnetic treatment device.

$$P_{EDDY} = \frac{\pi^2 \cdot B_P^2 \cdot d^2 \cdot f^2}{6 \cdot k \cdot \rho \cdot D}, \qquad \text{Eq. 1}$$

where: $P_{EDDY}$ is power loss per unit mass (W·kg$^{-1}$); $B_p$ is the peak of magnetic field (T); f is frequency (Hz); d is the thickness of the sheet or diameter of the wire (m); k is constant equal to 1 for a thin sheet and 2 for a thin wire; $\rho$ is the resistivity of material ($\omega$·m); D is the density of material (kg·m$^3$).

The individual insulation of each wire may reduce eddy currents. The individually insulated wires may be wound either one by one or in a bundle of individually insulated wires so as to form a magnetic field generating device, which may serve as a magnetic field generator. The magnetic field generating device may provide an improvement in the efficiency of energy transfer in the LC resonant circuit and also reduces or eliminates unwanted thermal effects.

The magnetic field generating device may include at least one conductor with a cross-section surface in a range of 0.0001 to 100 cm$^2$. Alternatively the cross-section surface may be in a range of 0.001 to 50 cm$^2$, preferably in a range of 0.01 to 20 cm$^2$, more preferably in a range of 0.5 to 1 cm$^2$, even more preferably in a range of 0.1 to 0.75 cm$^2$, most preferably in a range of 0.25 to 0.5 cm$^2$. The wires are preferably made of materials with higher density and higher resistivity e.g. gold, platinum or copper. The cross-section surface of the single wires should be minimal. On the other hand the total cross-section surface should be maximal because of inverse proportion between the cross-section of all wires forming the magnetic field generating device and the electrical resistance. Therefore the ohmic part of the heat is then lower. Eq. 2 describes power loss of the magnetic field generating device:

$$P_R = \frac{\rho \cdot \frac{l}{S} \cdot I^2}{m} \qquad \text{Eq. 2}$$

Where: $P_R$ is the power loss heat dissipation (W); $\rho$ is the resistance ($\Omega$·m); l is the length of wire (m); S is the surface area (m$^2$); I is the current (A) and m is 1 kg of wire material.

Total power loss is (Eq.3):

$$P_{TOT} = P_{EDDY} + P_R. \qquad \text{Eq. 3}$$

Where: $P_{TOT}$ is the total power losses (W·kg$^{-1}$); $P_{EDDY}$ is the power dissipation of eddy currents (W·kg$^{-1}$); $P_R$ is the power loss heat dissipation (W·kg$^{-1}$).

Dynamic forces produced by current pulses passing through the wires of the magnetic field generating device cause vibrations and unwanted noise. The individual insulated wires of the magnetic field generating device may be impregnated under pressure so as to eliminate air bubbles between the individual insulated wires. The space between wires can be filled with suitable material which causes unification, preservation and electric insulation of the system. Suitable rigid impregnation materials like resin, and elastic materials like PTE can be also used. With the magnetic field generating device provided as a solid mass, the vibrations and resonance caused by movements of the individual insulated wires are suppressed. Therefore noise is reduced.

The magnetic field generating device may be attached to the case of the applicator, such as a hand held applicator of the magnetic treatment device; build-in applicator in e.g. chair, bed; or stand-alone applicator e.g. on mechanical fixture. The hand held applicator may include a display unit for controlling the magnetic treatment device. Alternatively the display unit may display treatment parameters such as a repetition rate, a magnetic flux density or lapsed time of the treatment. The magnetic treatment device may preferably include a human machine interface (HMI) for displaying and/or adjusting the treatment parameters. The HMI may include at least one button, knob, slide control, pointer or keyboard. Alternatively the HMI may include a touchscreen, an audio-visual input/output device such as PC including display unit, an input unit and/or a graphical user interface.

The mechanical fixture may be rigid with the applicator hanging on the rigid mechanical fixture. Alternatively the mechanical fixture may be articulated. The mechanical fixture may include at least one joint to enable tailor made position of the applicator. The attachment may be provided by an elastic material e.g., silicone, gum; or other flexible manner. Connection with the magnetic field generating device of the applicator's casing may be ensured by several points. The several fastening points ensure the connection of the magnetic field generating device to the casing by flexible material so that the main part of the magnetic field generating device and the main part of the casing of applicator are spaced apart. The spacing should be at least 0.1 mm so that air can easily flow. Alternatively the spacing may be at least 1 mm, most preferably at least 5 mm to enable cooling media flow. The gap between the magnetic field generating device and the casing can be used either for spontaneous or controlled cooling. The magnetic field generating device may optionally be connected to the case of the applicator by only one fastening point. The fastening points eliminate vibrations of wires which could be transferred to casing of the applicator and therefore reduce noise of the magnetic treatment device.

Figure 2:
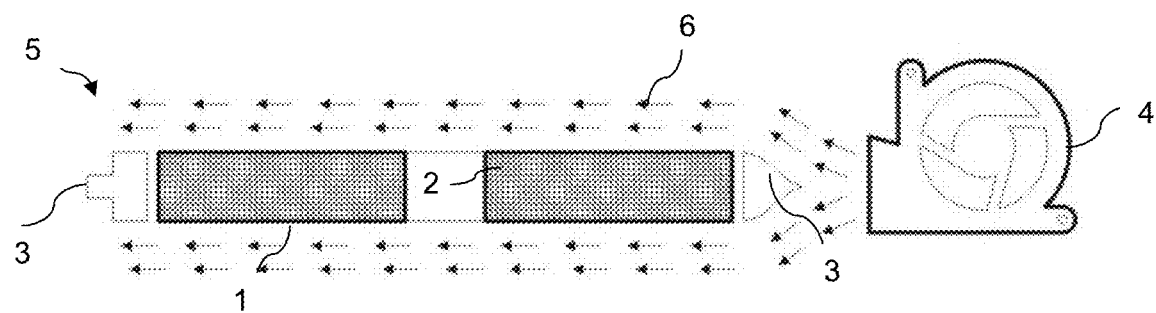
FIG. 2 is a cross-section of a magnetic applicator.

FIG. 2 is a cross-section of the magnetic applicator which allows better flow on the lower and upper sides of the magnetic field generating device and thus more efficient heat dissipation. The magnetic treatment device includes a magnetic field generating device 1, the circuit wires 2 and the fastening points 3 for connection of the magnetic field generating device to the casing of the applicator (not shown). The fastening points 3 are preferably made of flexible material however the rigid material may be used as well. The fastening points 3 may be located on the outer circumferential side of the magnetic field generating device. However, alternatively it is possible to put these fastening points to a lower or upper side of the magnetic field generating device.

The fastening points 3 connect the magnetic field generating device to the case of the applicator in at least one point. The fastening points 3 maintain the magnetic field generating device and the main part of the case of the applicator spaced apart so that fluid (which may be air or any liquid) can flow between them. At least one blower 4 can be placed around the circumference of the magnetic field generating device, or perpendicular to the magnetic field generating device. The blower can be any known kind of device for directing the fluid e.g. outer air directed into the case of the applicator. The blower may be e.g. a fan or a suction pump. This arrangement of the blower allows air to bypass the magnetic field generating device from upper and lower (patient's) sides. In still another embodiment the outer air can be cooled before directing into the case. The blower can have an inlet placed around the circumference of the magnetic field generating device for injecting air, to remove heat from the magnetic field generating device. A connecting tube (not shown) can ensure connection of the applicator 5 with the energy source and/or control unit of magnetic treatment device. The connecting tube may also contain a conduit of the fluid, e.g. a pressurized air.

Alternatively the magnetic field generating device may be attached to the casing of the applicator via a circular rigid member encircling the magnetic field generating device. The outer circumference of the circular rigid member may be attached to the casing of the applicator. The magnetic field generating device may be flexibly attached to the inner circumference of the circular rigid member by at least one attaching point. Alternatively the magnetic field generating device may be attached to the circular member by its entire circumference.

The arrows 6 indicate the air flow through the applicator 5. This arrangement of the blower allows the air to bypass the magnetic field generating device from upper and lower (patient's) side. Outlet may be preferably placed on upper side of the casing. The outlet may include a plurality of holes enabling unimpeded removing of heated cooling media from the casing of the applicator. By placing the blower around the circumference of the magnetic field generating device instead of on the top/below the magnetic field generating device, the blower 4 does not interfere with the magnetic flux peak and therefore its lifespan and reliability is increased.

Figure 3A:
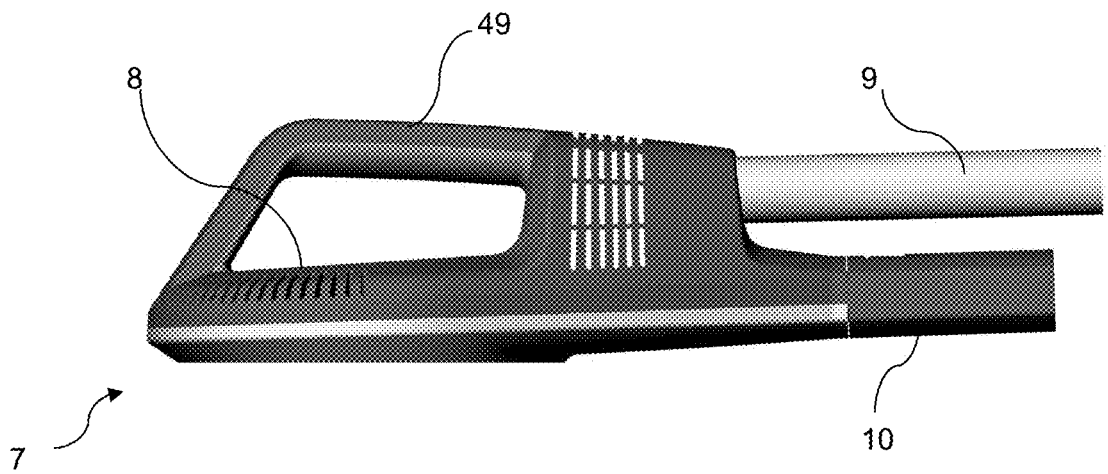
FIG. 3a-e illustrate exemplary embodiment of an applicator.

FIG. 3a is an illustrative embodiment of a casing of the magnetic applicator. The overview drawing contains casing itself 7, which might contain an outlet 8 preferably placed on upper side of the casing 7. The applicator may further include a handle 49 on the upper side of the casing. The handle 47 may be used for manual positioning the applicator. A connecting tube 9 may not only ensure connection of the applicator with the energy source and/or control unit of magnetic treatment device, but also connection to a source of the fluid; however the conduit of the fluid 10 may also be connected separately.

The connecting tube 9 may include a connector for connecting the applicator to the treatment device. The connector may be connected to the connecting tube 9 either on its first end between the connecting tube and the casing 7 of the applicator or the second end between the connecting tube and the treatment device. The applicator including the coil may be preferably connected to the magnetic treatment device by the connector independently on the positioning arm. The connector may be any kind of electromechanical connector providing electrical communication of the applicator to the treatment device. Mechanical connection may be provided by additional latching mechanism known in the art. The applicator may be replaced by another applicator. Each applicator may include unique identifier of the applicator for communication with the control unit of the treatment device. The communication may be via NFC, RFID, ZigBee, IRDC, Bluetooth or wired communication. Alternatively the applicator may include a mechanical identifier such as a specific combination of a plurality of pins in a pattern.

In an alternative embodiment cooling may be provided by a member using thermoelectric effect, e.g. a Peltier cooler. Alternatively, cooling may be provided by Stirling engine cooling system.

Figure 3B:
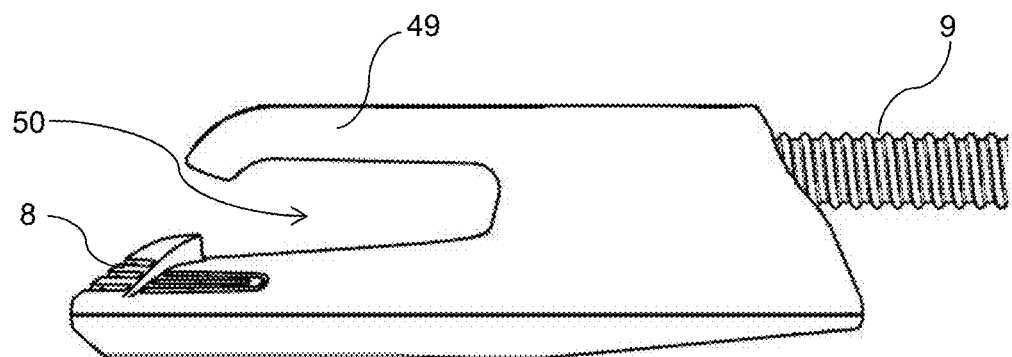

FIG. 3b illustrates a side view of an exemplary embodiment of concave applicator. The applicator of concave shape includes a handling member 49 as a concavity 50 of the applicator. The concavity may enable inserting a positioning member such as a length adjustable belt. The handling member 49 may be also used for manual positioning of the applicator. The handling member 49 may be preferably is a center of the applicator.

Figure 3C:
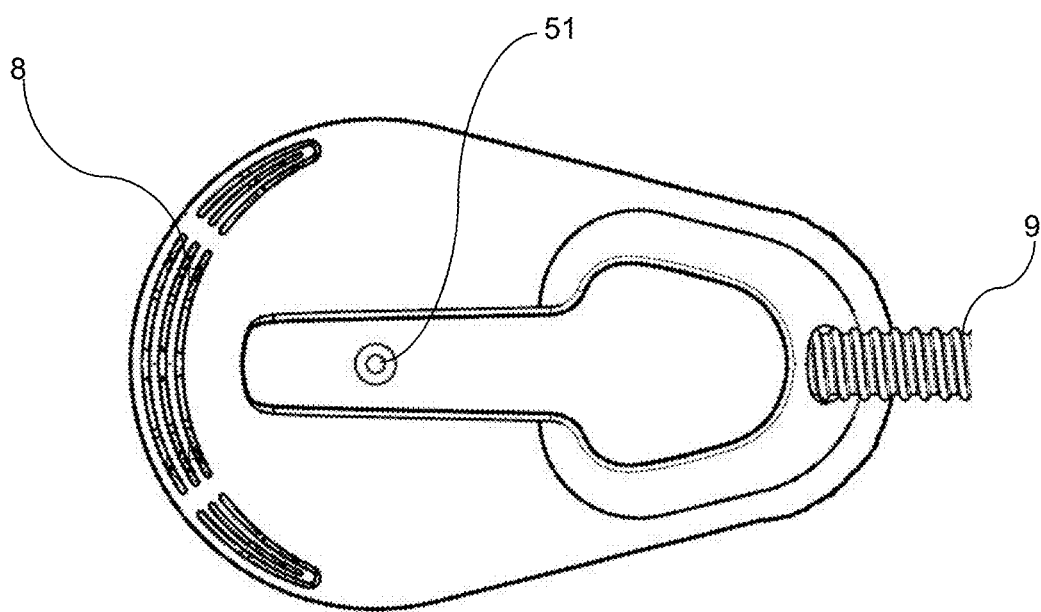

FIG. 3c illustrates a top view of the concave applicator. The applicator may preferably include a marker 51 above the center of the magnetic field generating device. The marker 51 may enable comfortable positioning the applicator by the operator. The marker may be a recess in a surface of the casing. Alternatively the marker may be different surface cover. Alternatively the upper side of the casing may include two colors. One color may be over the magnetic field generating device to enable correct positioning of the applicator. The rest of the applicator may be of different color. The color may be interpreted as a paint reflecting a specific wavelength and/or spectra.

The applicator may be made of biocompatible material enabling high hygiene standard, e.g. a fluidly sterilizable plastic.

Alternatively the applicator may be adapted to fit a body region of the patient including leg, arm, buttock or abdomen. The applicator may be shaped to correspond with the patient's body region such as a limb. The shape may include a concavity for maintaining the body region in the correct treatment location. The body region applicator, herein after as BR applicator, may be of a plurality of sizes configured to fit the patient's body region following the patient's needs.

The BR applicator may include a first portion on the patient's side, i.e. the first portion may be in a contact with the patient. The BR applicator may include a second portion on a side opposite to the first portion, i.e. the second portion may be farther from the patient than the first portion.

Figure 3D:
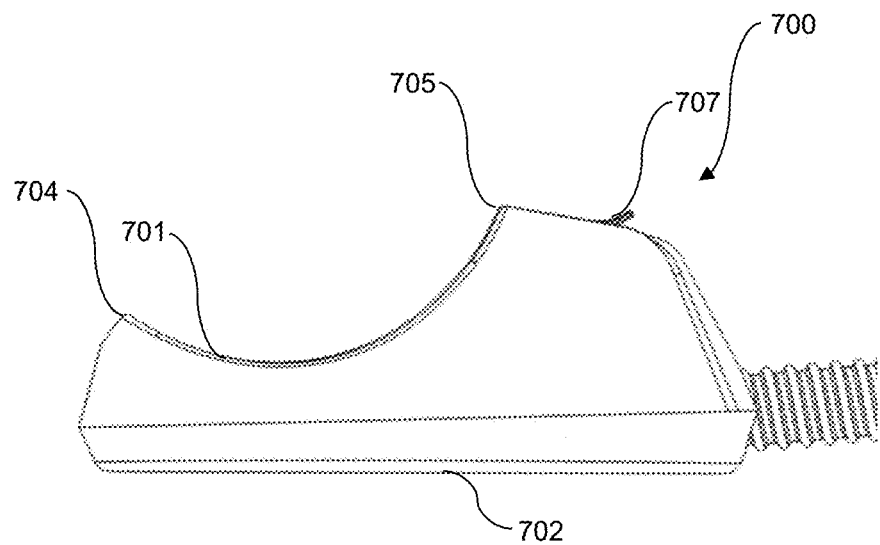
Figure 3E:
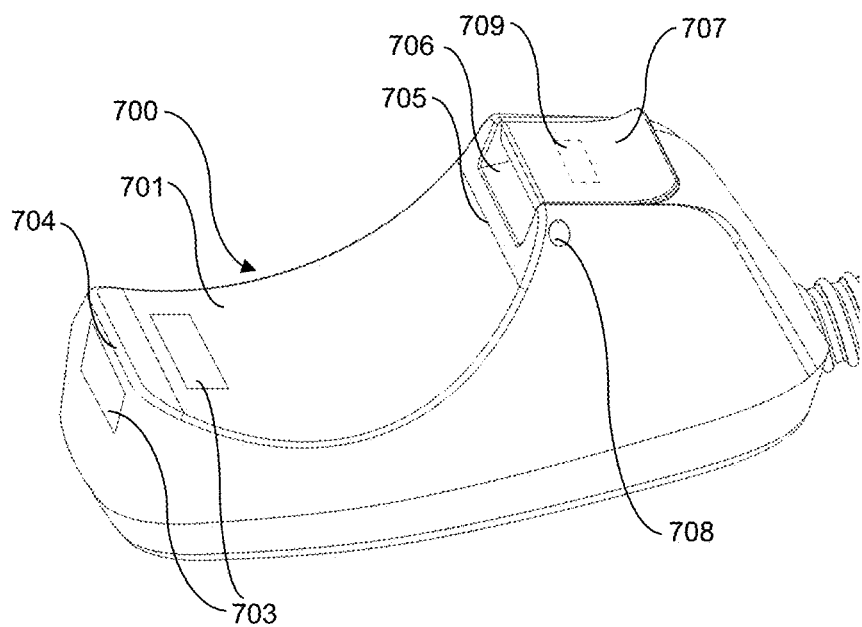

FIGS. 3d and 3e illustrate an exemplary embodiment of the BR applicator 700 used for a limb. The first side portion 701 may be at least partially concave. The first side portion 701 may be V-shaped or preferably U-shaped. A curvature radius of the first side portion 701 may be at least 1 mm, preferably in a range of 10 to 750 mm, more preferably in the range of 50 to 500 mm, most preferably in the range of 60 to 250 mm or up to 1 m. The curvature radius may correspond with a size of a limb. The first side portion 701 being at least partially concave may be a part of a total curvature of oval or circular shape. The first side portion may be at least 5° section of the total curvature, the section may be preferably in a range of 10 to 270°, more preferably in the range of 30 to 235°, even more preferably in the range of 45 to 180°, most preferably in the range of 60 to 135°. The first side portion may be configured to maintain the limb within the first side portion during the treatment. The first side portion may provide a stable equilibrium for the treated body region. The limb of the patient may be maintained in the first side portion even though the limb may move by the muscle contractions. The lateral movement and/or rotation of a limb may be limited due to the first side portion and the limb may be in stable position. The rotation movement with respect to the BR applicator may be limited by attaching the BR applicator to the body region.

The second side portion 702 may be preferably on the opposite side of the BR applicator 700 with respect to the first side portion 701. The second side portion 702 may be substantially planar. The second side portion may be configured to maintain the applicator on the patient support which the patient may lay on during the treatment. In an exemplary embodiment the second side portion may include a positioning mechanism for manual adjusting a position of the magnetic field generating device within the BR applicator.

The BR applicator 700 may be attached to the patient by a positioning mechanism such as a length adjustable belt which may be flexible. In exemplary embodiment the length adjustable belt may be fixed in a recess/cutout 703 at first end 704 of the first side portion 701. Second end 705 of the first side portion 701 may include a recess 706 and a clip mechanism for fixing the length adjustable member in the recess 706. The clip 707 may move around the pin 708 in a clockwise or counterclockwise direction. The clip may be biased by a spring. Alternatively the clip may be locked by a suitable locking mechanism, or by any other movement restraining manner. The clip may include a fastener 709 on lower side of the clip for fixing a correct length of the length adjustable member. The fastener may be hook-and-loop fastener, e.g. Velcro fastener, pin type etc.

In an alternative embodiment the BR applicator may include a counterpart to the part including the magnetic field generating device. The at least one counterpart may be configured to maintain the limb applicator in static position with respect to the body region. The counterpart may be preferably placed on the opposite side of the body region. The counterpart may be attached to the part including the magnetic field generating device by a flexible member or a length adjustable belt. Alternatively the counterpart may be attached by a hinge. Alternatively the counterpart may be attached to the BR applicator by a suitable locking mechanism, e.g. clip, spring clip, pin-type etc. The counterpart and the part including the magnetic field generating device may preferably at least partially encircle the limb.

An exemplary application may be limb treatment. The limb applicator may be placed around entire circumference of the limb.

According to an exemplary application m. triceps brachii may be treated by the time-varying magnetic field. The patient may lay in supine position on a patient support such as a bed, a couch or a chair. An arm of the patient may be set into the concavity of the applicator including the magnetic field generating device, i.e. to the first side portion 701. The second side portion 702 may be in contact with the patient support. The time-varying magnetic field may be applied to the muscle and/or to the nerve innervating the muscle. The time-varying magnetic field may be applied to the arm with a magnetic flux density and/or a maximum value of the magnetic flux density derivative sufficient to cause a contraction of the muscle within the arm. The applicator may be attached to the limb of the patient by a length adjustable member such as a belt. The potential energy of the treated body region may be maintained at minimum.

According to another exemplary application m. biceps brachii may be treated by the time-varying magnetic field. The patient may lay in supine position on the patient support. The arm may be preferably in supine position. The applicator may be placed within proximity of the patient's arm, preferably within close proximity of the muscle. Alternatively the patient may sit on the patient support such as chair with arm resting on armrest of the patient support. The arm may be bent in the elbow in order to enable correct treatment of the particular muscle. The applicator may be attached to the arm as well.

The limb applicator may be used for treatment of leg as well. According to another exemplary application the patient may lay in prone position on the patient support and the limb applicator may be placed over the leg of the patient, such as over a calf or thigh. Alternatively the patient may lay in supine position on the patient support and the limb applicator may be placed below the leg of the patient, i.e. the leg may lay on the limb applicator. Alternatively the patient may have bent knee with limb applicator on the treated body region. Alternatively the thigh may be in vertical position and the calf may be in horizontal position.

The magnetic field generating device may correspond with a shape of the applicator. The magnetic field generating device may not be planar. The magnetic field generating device may be conical, convex and/or concave, e.g. biconvex, plano-convex, positive meniscus, negative meniscus, planoconcave or biconcave. The non-planar shape of the magnetic field generating device may enable larger cooling surface and the cooling may be more efficient. Further the non-planar shape may enable shifting the peak of the magnetic field closer/farther to/from the patient or the profile of the magnetic field may be adjusted by the non-planar shape of the magnetic field generating device. The treatment by non-planar magnetic field generating device may be more efficient compared to treatment by planar magnetic field generating device. The magnetic flux density, generated by the magnetic field generating device, sufficient for causing muscle contraction might be of lower value compared to planar coil. Heat dissipation may be enhanced by the larger surface cooled by a cooling media. The power consumption may be lower.

A static position of the at least one applicator may be provided by a positioning member. The positioning member may be e.g. an arm or an adjustable flexible belt. The positioning member may ensure tight attachment of the applicator within the proximity of the body region, or alternatively, direct contact with the patient. The direct contact with the patient may include direct contact with the skin of the patient, i.e. the applicator including the magnetic field generating device touching the patient's skin or the applicator contacting the patient's skin through a garment or any spacing object. Alternatively, the positioning member may hold the applicator including the magnetic field generating device in no contact with patient's skin.

The positioning member may include a buckle for adjusting the length of the belt. The applicator may be placed within predefined locations of the belt. Alternatively the applicator may be shaped to be moveable along the positioning member, e.g. the shape of the applicator may be preferably concave, e.g. V-shaped or U-shaped. The positioning member may be inserted itself into the concavity of the applicator. The position of the applicator may be adjusted by limited movement along the positioning member because the positioning member may be used as guiding member. However, the applicator may not be fixed to a particular static position. The position of the applicator may be dynamically adjusted during the treatment following the patient's needs. The position of the applicator may be adjusted manually by the operator, or automatically by the treatment device. In one exemplary embodiment a plurality of applicators may be used for treating larger body regions, e.g. buttock, abdomen or thigh, or pair muscles.

The positioning arm may include a plurality of moveable members which may be articulated. A motion of the at least one moveable member may be translational and/or rotational. The positioning arm may include at least on joint providing at least one degree of freedom for the positioning arm. In more preferred embodiment the positioning arm includes a plurality of degrees of freedom, e.g. two, three or more. An example of such positioning arm may be an open kinematic chain including at least two, more preferably four, even more preferably six degrees of freedom. A fixed frame of the open kinematic chain may be a body of the magnetic treatment device. An endpoint of the kinematic chain may be an applicator and/or a magnetic field generating device.

Figure 4A:
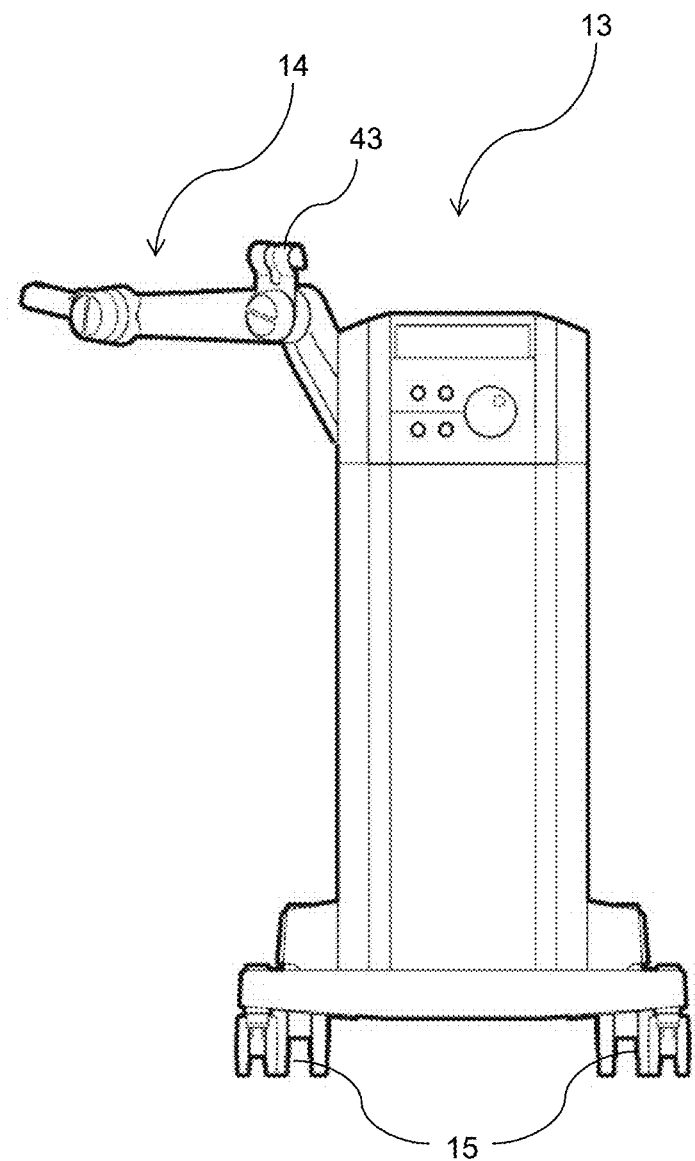
FIG. 4a-4c illustrates a positioning arm

FIG. 4a illustrates an exemplary embodiment of the treatment device 11 including a positioning arm 12 for positioning the applicator (not shown). The treatment device 11 may include wheels 14 for moving the treatment device. The wheels may be propelled. A plurality of the wheels may be preferably outside of a floor projection of the body of the treatment device in order to provide improved stability of the treatment device.

Figure 4B:
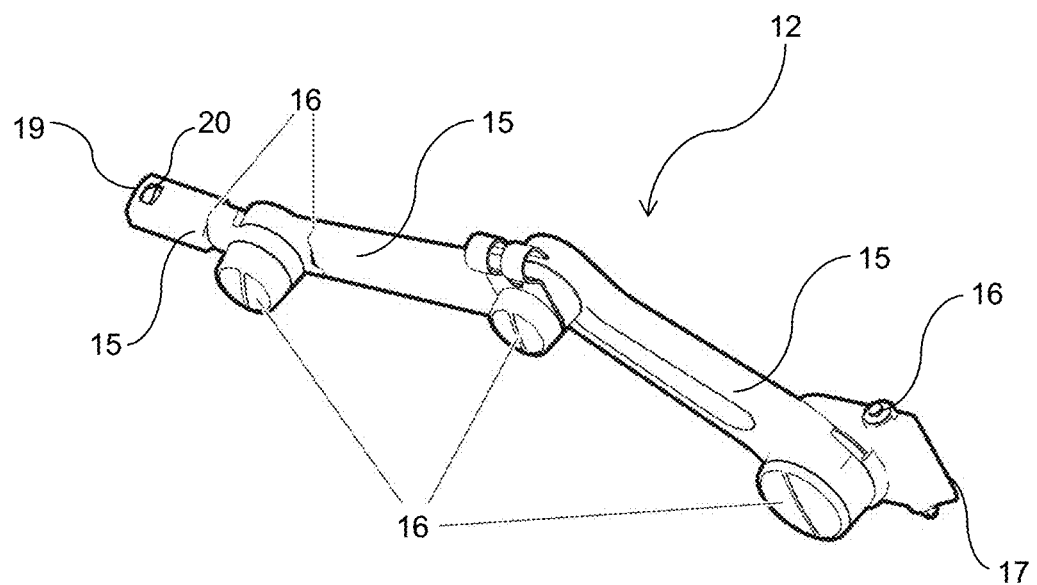

FIG. 4b illustrates the positioning arm 12 including moveable links 15 connected by joints 16 enabling two, four most preferably six degrees of freedom. Three of these joints may be locked by a locking mechanism such as a screw mechanism. The positioning arm may include a support member for attaching the connecting tube to the positioning arm. The support member may maintain the connecting tube in parallel direction with respect to the positioning arm.

The positioning arm 12 is attached to the treatment device 11 at first end of the positioning arm 17 (not shown). In an exemplary embodiment the positioning arm is attached to a circumferential side of the treatment device.

The positioning arm further includes a hollow sleeve 18 at the second end 19. The sleeve 18 includes a gap 20 for removably attaching the applicator 13 to the positioning arm 12.

The positioning arm may include a member for guiding the connecting tube.

Figure 4C:
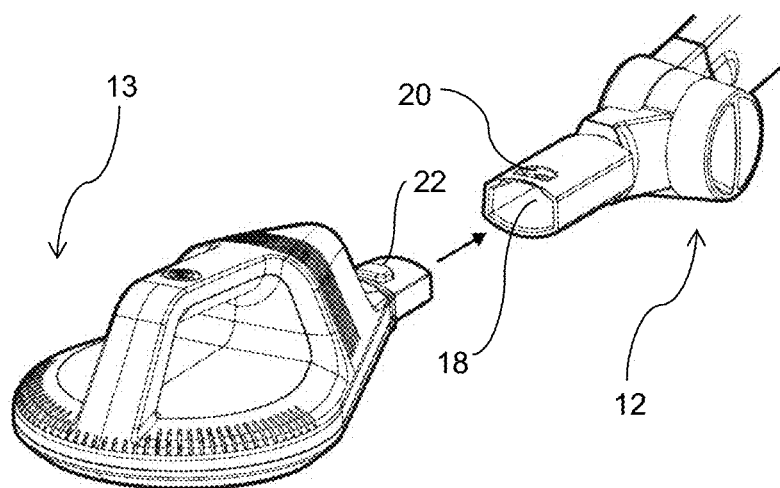

FIG. 4c illustrates an applicator 13 which may be removably attached to the positioning arm 12. The connection of the applicator 13 to the positioning arm is enabled by a locking mechanism. The applicator 13 includes a latching member 22 biased by a resilient member. The latching member 22 is adapted to fit the gap 20 in the hollow sleeve 18 at the second end of the positioning arm. The applicator 13 is attached to the positioning arm 12 by inserting the applicator 13 into the sleeve 18 and locking the latching member 22 in the gap 20. Applicator may be removed by pressing the latching member and pulling the applicator from the sleeve.

Still other embodiments of positioning member may be found in provisional U.S. patent application No. 62/357,679 incorporated herein by reference.

Figure 5A:
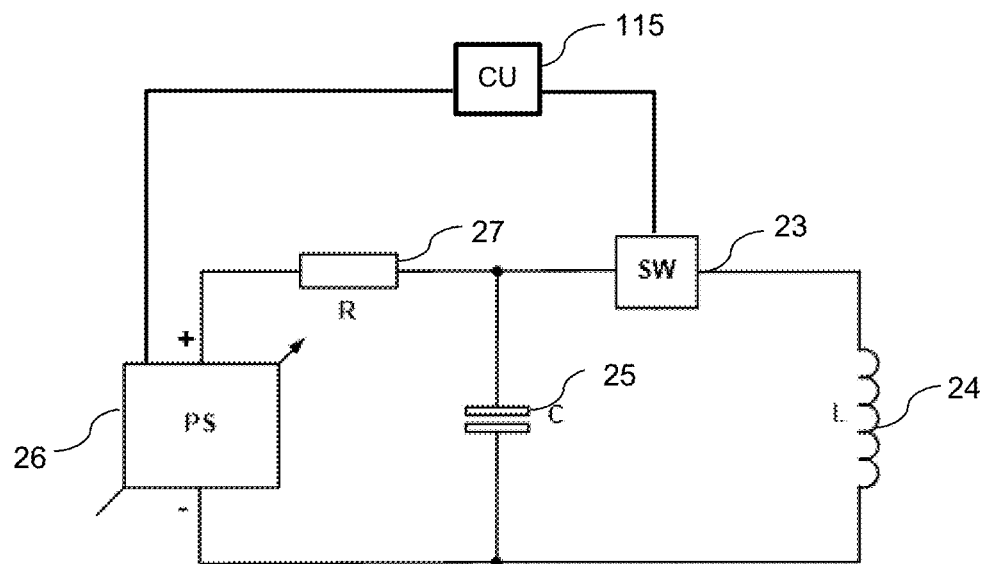
FIGS. 5a and 5b illustrate circuits for providing high power pulses to a stimulating magnetic field generating device.
Figure 5B:
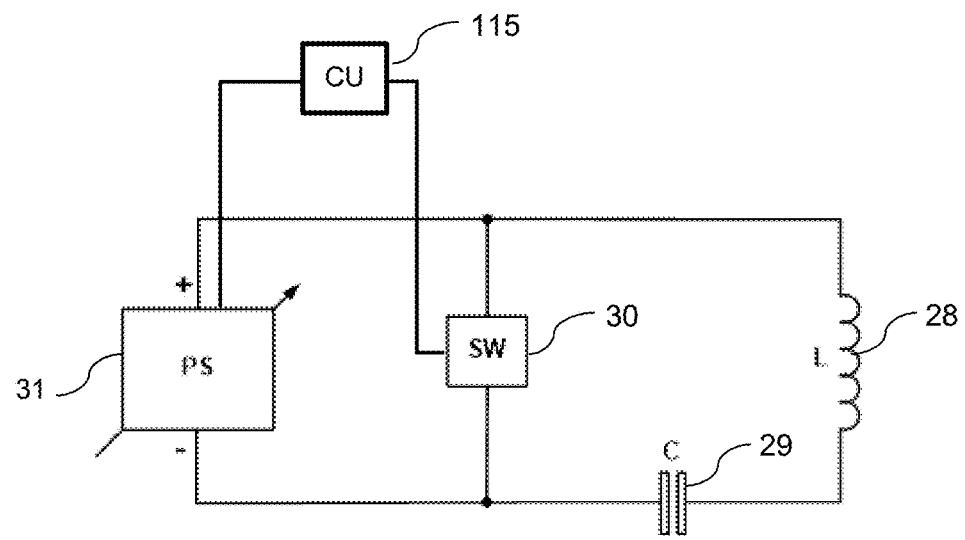

FIG. 5a and FIG. 5b illustrate exemplary embodiments of circuits for providing high power pulses to the stimulating magnetic field generating device. The proposed circuits include charging the energy storage device from the energy source, repetitively switching the switching device, and discharging the energy storage device to the magnetic field generating device in order to generate the time-varying magnetic field. Either the energy source or the switching device, or alternately both the energy source and the switching device, may be regulated by a control unit. The control unit may also enable regulating and/or adjusting the treatment parameters described in this document in order to generate time varying magnetic field for the treatment. The regulation may be done by the preset protocol or by the operator/end user of the device through HMI.

Referring to FIG. 5a, the circuits for providing high power pulses to the stimulating magnetic field generating device contain a series connection to the switch 23 and the magnetic field generating device 24. The switch 23 and the magnetic field generating device 24 together are connected in parallel with an energy storage device 25. The energy storage device 25 is charged by the energy source 26 and the energy storage device 25 then discharges through the switching device 23 to the magnetic field generating device 24.

During second half-period of LC resonance, the polarity on the energy storage device 25 is reversed in comparison with the energy source 26. In this second half-period, there is a conflict between energy source 26, where voltage on positive and negative terminals is typically thousands of Volts. The energy storage device 25 is also charged to the positive and negative voltage generally to thousands of Volts. As a result, there is in the circuit, consequently, twice the voltage of the energy source 26. Hence the energy source 26 and all parts connected in the circuit are designed for a high voltage load. Therefore, the protective resistors and/or protection circuitry 27 must be placed between energy source 26 and energy storage device 25. Either the energy source 26 or the switch 23, or alternately both the energy source 26 and the switch 23 may be regulated by a control unit 115. The control unit 115 may enable regulating and/or adjusting the parameters described in this document in order to generate time varying magnetic field for the treatment. The regulation may be done by the preset protocol or by the operator/end user of the device through HMI.

FIG. 5b shows a circuit for providing high power pulses for improved function of the treatment device. The magnetic field generating device 28 and an energy storage device 29 are connected in series and disposed in parallel to the switch 30. The energy storage device 29 is charged through the magnetic field generating device 28. To provide an energy pulse, controlled shorting of energy source 31 takes place through the switch 30. In this way the high voltage load at the terminals of the energy source 31 during the second half-period of LC resonance associated with known devices is avoided. The voltage on the terminals of energy source 31 during second half-period of LC resonance is a voltage equal to the voltage drop on the switch 30. Either the energy source 31 or the switch 30, or alternately both the energy source 31 and the switch 30, may be regulated by a control unit 115. The control unit 115 may enable regulating and/or adjusting the parameters described in this document in order to generate time varying magnetic for the treatment. The regulation may be done by the preset protocol or by the operator/end user of the device through HMI.

A capacitance of the energy storage device may be in the range of 5 nF to 100 mF, preferably in the range of 25 nF to 50 mF, more preferably in the range of 100 nF to 10 mF, even more preferably in the range of 1 µF to 1 mF, most preferably in the range of 5 to 500 µF.

The energy storage device may be charged on a voltage of at least 100, 250, 500, 1000, 1500, 2500 V or more.

The energy storage device may provide a current pulse discharge at least 100, 250, 500, 750, 1000, 1500, 2000 A or more. The current may correspond with a value of the peak magnetic flux density of the magnetic field generated by the coil.

The switch 30 can be any kind of switch such as diode, MOSFET, JFET, IGBT, BJT, thyristor or their combination. Depending on the type of component the load of energy source 31 is reduced to a few Volts, e.g., 1-10 volts. Consequently, it is not necessary to protect the energy source 31 from a high voltage load, e.g., thousands of Volts. The use of protective resistors and/or protection circuits is reduced or eliminated. The present designs simplify the circuits used, increase efficiency of energy usage and provide higher safety.

An inductance of the magnetic field generating device may be up to 1 H, or in the range of 1 nH to 500 mH, or in the range of 1 nH to 50 mH, preferably in the range of 50 nH to 10 mH, more preferably in the range of 500 nH to 1 mH, most preferably in the range of 1 to 500 pH.

Figure 6:
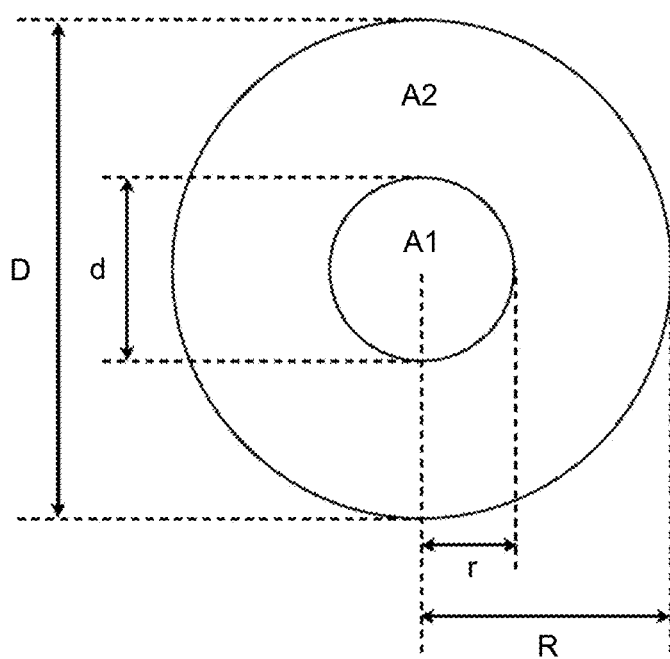
FIG. 6 illustrates dimensions of a magnetic field generating device.

FIG. 6 illustrates a floor projection of an exemplary embodiment of circular planar magnetic field generating device. The magnetic field generating device is characterized by dimensions including outer diameter D; inner diameter d; inner radius r and outer radius R. The magnetic field generating device is further characterized by areas A1 and A2. Alternatively the magnetic field may be oval, rectangular or square with corresponding dimensions.

The area A1 is associated with dimensions r and d. The area A1 includes no winding. The area A1 may be represented by a core. The core may be preferably air core. Alternatively the core may be a permeable material having high field saturation, e.g. iron alloys such as permendur, permalloy or silicon iron/steels.

The area A2 is associated with dimensions R and D. The area A2 includes the magnetic field generating device itself, i.e. windings of the magnetic field generating device.

The dimension r may be in the range of 1 to 99% of the dimension R, more preferably in the range of 2 to 95% or 3 to 80% of the dimension R, even more preferably in the range of 4 to 60% or 6 to 50% of the dimension R, most preferably in the range of 7 to 40%. The dimensions of r and R may be used for achieving convenient shape of the generated magnetic field.

In an exemplary embodiment the magnetic field generating device diameter D is 100 mm and the dimension r is 10% of the dimension R. In that exemplary case the dimension R is 50 mm and the dimension r is 5 mm.

The area A2 includes a plurality of windings. One winding may include a plurality of wires, preferably insulated wires. The windings are preferably tightly arranged, most preferably one winding touching the adjacent winding. The winding area A2 may be at least 0.99 cm². The winding area A2 may be in the range of 4 to 7900 cm², preferably in the range of 9 to 1950 cm², more preferably in the range of 15 to 975 cm², most preferably in the range of 45 to 450 cm².

Alternatively the windings may include a gap between each other. The gap may be up to 50, 25 15, 10, 5, 1, 0.5 or 0.1% of the dimension R-r.

A total magnetic field generating device surface, i.e. A1+A2, may be in the range of at least 1 cm². The total magnetic field generating device surface may be up to 8000 cm², or in the range of 5 to 8000 cm², preferably in the range of 10 to 2000 cm², more preferably in the range of 20 to 1000 cm², most preferably in the range of 50 to 500 cm².

The core area A1 may be in a range of 0.01% to 99% of the total magnetic field generating device surface. Alternatively the core area A1 may be in a range of 0.05% to 95%, preferably in a range of 0.5 to 90%, more preferably in a range of 1 to 75%, even more preferably in a range of 5% to 60%, most preferably in a range of 10% to 40% of the total magnetic field generating device surface.

A total weight of the magnetic field generating device may be in a range of 1 gram to 50 kg. The total weight of the magnetic field generating device may be preferably in a range of 10 gram to 25 kg, more preferably in a range of 0.1 to 15 kg, even more preferably in a range of 0.5 to 10 kg, most preferably on the order of kilograms, for example 1 kg, 2 kg, 3 kg, 5 kg, or more.

A magnetic fluence is defined by Equation 4.

$$MF = B_{PP} \cdot A_{MFGD}$$ Eq. 4 where: MF is magnetic fluence [T·cm²]; $B_{PP}$ is maximal peak to peak magnetic flux density generated by the magnetic field generating device [T]; $A_{MFGD}$ is area of the magnetic field generating device [cm²].

The at least one magnetic field generating device may generate the time-varying magnetic field of the magnetic fluence in a range of 5 to 60000 T·cm², or in a range of 60 to 60000 T·cm², or in a range of 70 to 60000 T·cm², or in a range of 5 to 40000 T·cm², preferably in the range of 70 to 20000 T·cm², more preferably in the range of 75 to 15000 T·cm², even more preferably in the range of 80 to 2000 T·cm² or up to 60000 T·cm².

Alternatively the time-varying magnetic field with the magnetic fluence may be generated by a plurality of magnetic field generating devices.

A winding magnetic fluence is defined by Equation 5.

$$WMF = B_{PP} \cdot A_2$$ Eq. 5 where: WMF is winding magnetic fluence [T·cm²]; $B_{PP}$ is maximal peak to peak magnetic flux density generated by the magnetic field generating device [T]; $A_2$ is winding area of the magnetic field generating device [cm²].

The at least one magnetic field generating device may generate the time-varying magnetic field with the winding magnetic fluence of at least 5, 10, 15 or 20 T·cm², or in a range of 5 to 40000 T·cm², or in a range of 40 to 40000

T·cm², or in a range of 40 to 20000 T·cm², preferably in the range of 50 to 10000 T·cm² or in a range of 75 to 7500 T·cm², more preferably in the range of 100 to 5000 T·cm² or 150 to 2750 T·cm², even more preferably in the range of 200 to 2000 T·cm² or 275 to 1500 T·cm², or up to 40000 T·cm². Alternatively the time-varying magnetic field with the winding magnetic fluence may be generated by a plurality of magnetic field generating devices.

According to some embodiments, the magnetic field generating device may have round, circular, oval, square, rectangular or any other shape. Alternatively, the magnetic field generating device may be a solenoid.

Figure 7:
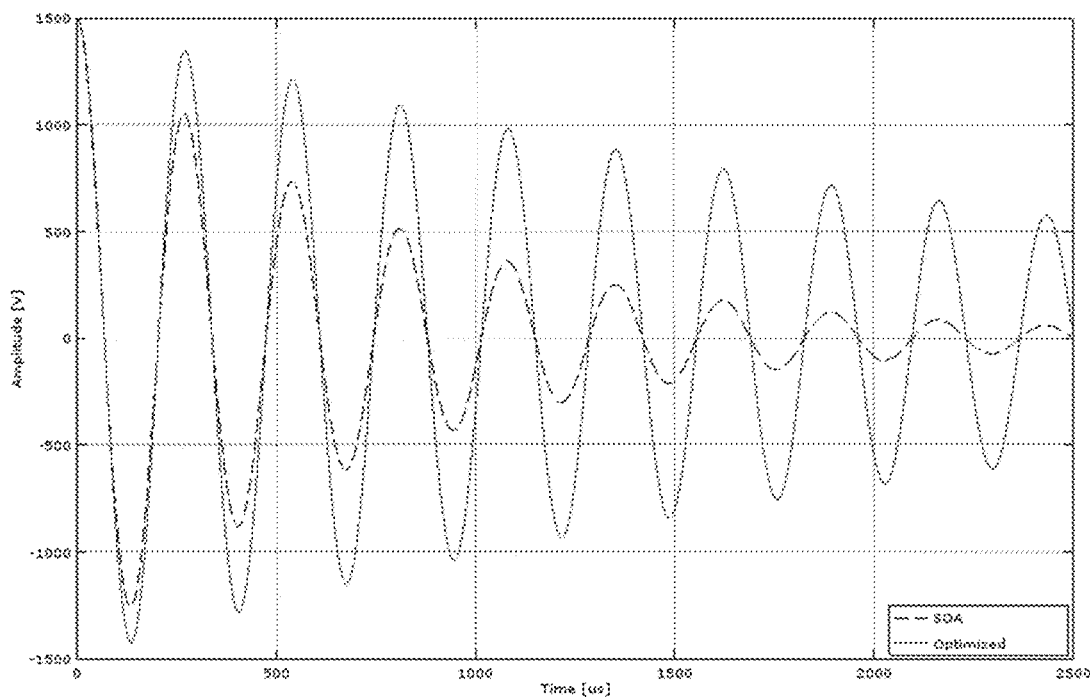
FIG. 7 is a graph showing voltage drop in the energy storage device.

FIG. 7 shows an exponential voltage drop in the energy storage device. Energy savings during treatment may be characterized by reduced voltage drop in the energy storage device between the first, second and subsequent maximums of the resonant oscillation. The magnitude of the individual voltage oscillations is exponentially dampened up to establishing the energy balance. This allows increasing the maximum possible frequency/repetition rate of magnetic pulses, since the frequency/repetition rate is dependent on the speed with which it is possible to recharge the energy storage device. Since the energy storage device is recharged by the amount of energy loss during the previous pulse, it is possible to increase the frequency/repetition rate of the treatment device up to hundreds of magnetic pulses per second without the need to increase the input power. The voltage drop between any of the successive amplitudes is not higher than 45, 40, 30, 21, 14 or 7%.

The treatment device may include at least one sensor for measuring operation parameter such as voltage, current or phase. The measured operation parameter may be processed by control unit of the treatment device and it may be used for determining a value of the generated heat. The generated heat may be used for prediction of a temperature of the magnetic treatment device. Typically the method may be used for treatment planning and/or to predict the temperature of the applicator and/or the part of the magnetic treatment device which is the most susceptible to overheating such as wires and/or resistors etc.

The magnetic treatment device may be described by the transition thermal characteristic (TTC). The TTC may be determined by experimental measurement during standard ambient conditions such as temperature and/or pressure, or it may be a mathematical model based on technical and/or electric specifications of all components of the magnetic treatment device. TTC characterizes the temperature dependence of the magnetic treatment device on generated heat. TTC is established by the manufacturer as the factory settings.

The value of generated heat determined by the recited application of the invention corresponds with the treatment parameters. The temperature evolution of the magnetic treatment device is dependent during the treatment on at least one of treatment parameters, actual temperature of the magnetic treatment device, ambient temperature, cooling medium temperature, cooling medium flow or heat dissipation.

A control unit is set up to operate with at least TTC and treatment parameters to determine the temperature of the magnetic treatment device during the treatment. The maximal temperature of the magnetic treatment device is limited and predetermined. However, in alternative application the maximal temperature of the magnetic treatment device may be adjusted by the operator. The maximal temperature may be considered to be safe for the patient.

The magnetic treatment device may include a system for monitoring a presence of the patient on a patient support. The patient support may include at least one pressure sensor such as a load cell, an accelerometer, an optical sensor, or a capacitive sensor. Alternatively the sensor may be a camera placed a predetermined distance from the patient support. The sensor may measure one or more physical quantities. The control unit of the magnetic treatment device may evaluate one or more signals from the sensor. The control unit may start and/or stop the treatment in response to a signal value from the pressure sensor.

The magnetic treatment device may include a plurality of pressure sensors. The plurality of pressure sensors may enable determination of at least a position of the patient on the patient support. The control unit may adjust a position of the magnetic field generating device in the patient support to improve a treatment effect. Alternatively the control unit may notify an operator to reposition the patient.

The device may be used for treatment/successive treatments in continual, interrupted or various duty cycle regime. The treatment duty cycle may be higher than 10%, which means interrupted regime with the ratio up to 1 active to 9 passive time units. The ratio may possibly change during the therapy. In the preferred application the treatment duty cycle may be at least 15, 20, 25, 40, 50, 75, 85 or 90%.

In an exemplary embodiment the magnetic treatment device include a main body of the magnetic treatment device and a plurality of applicators. Preferably two applicators may be used. The main body of the magnetic treatment device may include a connection to a power grid and two independent circuits for generating the magnetic field. Each independent circuit may include a power source, a switching device, an energy storage device and a magnetic field generating device. Alternatively one energy source may be common for a plurality magnetic field generating circuits. The magnetic field generating device may be preferably externally from the main body of the magnetic treatment device, i.e. in the applicator. Each applicator may include one magnetic field generating device. Alternatively a plurality of the magnetic field generating devices may be in one applicator. In an alternative embodiment the device may include a common energy storage device and/or switch for the plurality of coils.

Alternatively the magnetic field generating devices may generate the time-varying magnetic field simultaneously. The magnetic field generated simultaneously may interfere. Alternatively the plurality of magnetic field generating devices may generate the magnetic field in different time, e.g. sequentially.

Figure 12:
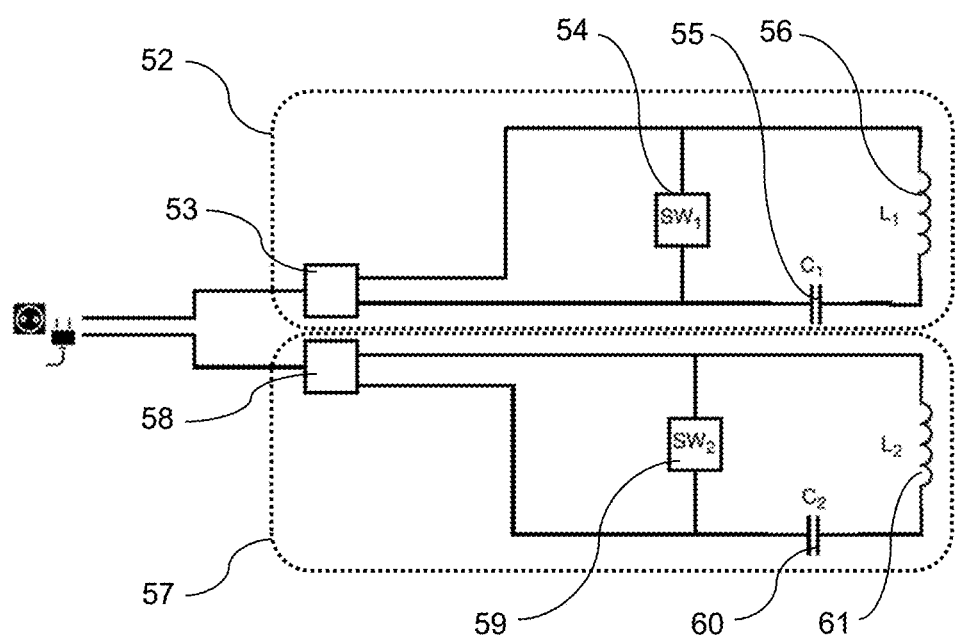
FIG. 12 illustrates an exemplary embodiment of a treatment device including two circuits generating independent magnetic fields.

FIG. 12 illustrates an exemplary embodiment of the magnetic treatment device including two independent magnetic field generating circuits (dotted lines). Magnetic field generating circuit 52 may include an energy source 53; switching device 54; energy storage device 55 and magnetic field generating device 56. Magnetic field generating circuit 57 may include an energy source 58; switching device 59; energy storage device 60 and magnetic field generating device 61.

Alternatively the magnetic field generating circuit may include a plurality of energy storage devices providing energy to a magnetic field generating device in order to enable higher energy pulse. Alternatively at least one energy storage device may provide energy to a plurality of magnetic field generating devices. Alternatively both circuits may include common power supply.

Circuit 52 may generate the time-varying magnetic field independently on Circuit 57. The magnetic treatment device may generate the magnetic field by one circuit while the second circuit is being turned off, i.e. Circuit 52 may generate the magnetic field while Circuit 57 is turned off or Circuit 57 may generate the magnetic field while Circuit 52 is turned off.

Alternatively Circuit 52 may generate the magnetic field of equal treatment parameters as the magnetic field generated by Circuit 57. Both circuits may be set up individually or synchronously. Each of the plurality of the magnetic field generating device 56, 61 may provide the magnetic treatment at the same time without necessity of alternating the magnetic field generating devices during the treatment.

Alternatively Circuit 52 may generate magnetic field of treatment parameters different from magnetic field generated by Circuit 57.

The control unit may control providing energy from the at least one energy storage device to the plurality of coils in order to generate a plurality of magnetic impulses by each coil. All coils of the plurality of coils may generate magnetic field within the treatment without any operator's input. The treatment may include a plurality of impulses, pulses, trains, bursts, a time period of no magnetic field applied to the patient or the time period when the magnetic flux density of the magnetic field is insufficient to induce eddy current in the patient in order to cause a muscle contraction.

Figure 8:
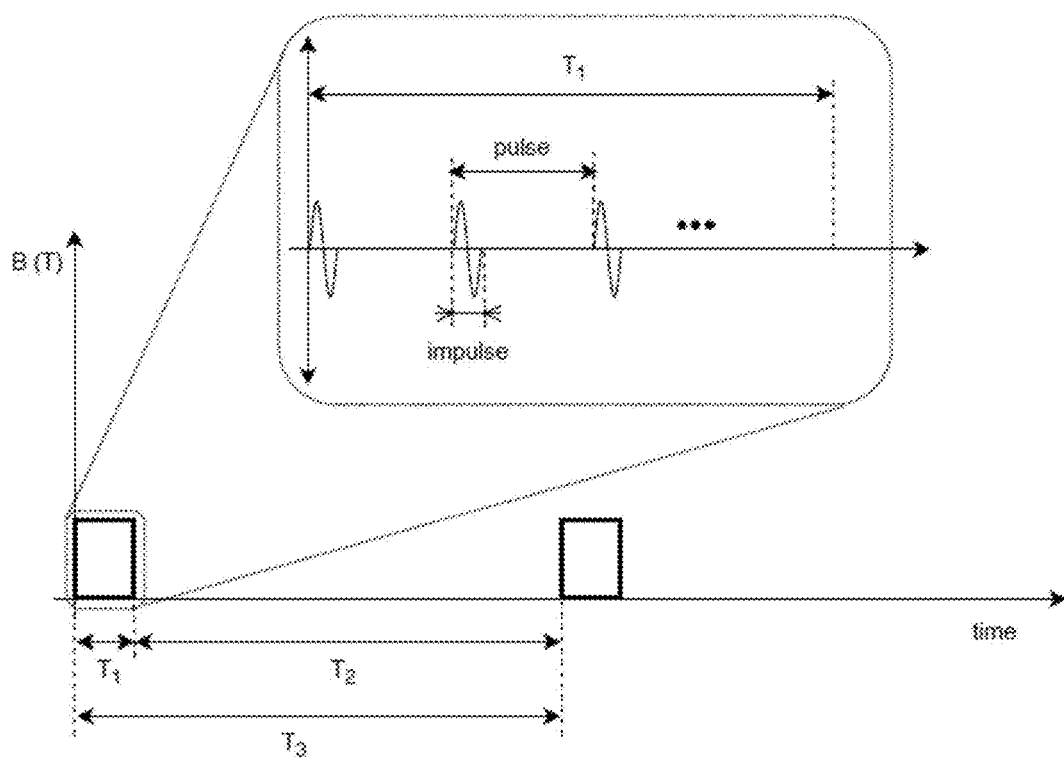
FIG. 8 illustrates an exemplary treatment duty cycle

FIG. 8 illustrates an exemplary treatment duty cycle of 10% while the exemplary repetition rate is 10 Hz. An active treatment (e.g. train of pulses) lasts for a period T1. Active treatment period may be called a train. T1 lasts 2 s. Hence the target biological structure is treated by 20 magnetic pulses. Passive treatment lasts for a period T2. T2 lasts 18 second. The period T1 is repeated after T2. In this exemplary treatment the period including active and passive period lasts 20 seconds. Active treatment followed by passive treatment may be called a burst, i.e. the burst includes one train and a period of no magnetic field applied to the patient. Time of burst T3 equals to T1+T2. The train includes a plurality of pulses, i.e. at least two pulses. The bursts may be repetitively applied to the patient. The burst repetition rate may be in a range of 100 Hz to 0.01 Hz, more preferably in a range of 50 Hz to 0.02 Hz or most preferably in a range of 10 Hz to 0.05 Hz.

An exemplary application of a burst repetition rate of 4 Hz may be the time-varying magnetic field applied to the patient with a repetition rate of 200 Hz and with a treatment duty cycle of 50% in trains lasting 125 ms; i.e. the train includes 25 pulses. An alternative exemplary application of a burst repetition rate of 6/min may be the time-varying magnetic field applied to the patient with a repetition rate of 1 Hz and with a treatment duty cycle of 30% in trains lasting 3 s; i.e. the train includes 3 pulses.

The device enables operation defined by the peak to peak magnetic flux density on the magnetic field generating device surface at least 3 T, more preferably at least 2.25 T, most preferably at least 1.5 T at repetition rates above 50 Hz, more preferably at repetition rates above 60 Hz, even more preferably at repetition rates above 70, most preferably at repetition rates above 80 Hz with treatment/successive treatments lasting several seconds or longer, for example, for at least 5, 10, 30, 60, 120 or 240 seconds, or longer. The total power consumption is below 1.3 kW and the width of pulses is in the range of hundreds of µs.

The device enables achieving repetition rates above 100 Hz, more preferably repetition rates above 150 Hz, most preferably repetition rates above 200 Hz with the magnetic flux density providing a therapeutic effect on neurons and/or muscle fibers and/or endocrine cells (e.g. at least muscle contraction, action potential in cell). Based on achievement of repetition rates in order of few hundreds the device also enables assembling the magnetic pulses into the various shapes (e.g. triangular, rectangular, exponential, trapezoidal), with the shape widths from 6 ms to several seconds or longer.

The device may enable a continual treatment and continual magnetic treatment where the set of the magnetic flux density and frequency/repetition rate of magnetic pulses does not lead to exceeding of the operating temperature 60° C., preferably 56° C., more preferably 51° C., even more preferably 48° C. most preferably 43° C. on the casing of the device operating in an ambient temperature of 30° C. regardless of the duration of therapy.

The treatment device may include a communication module connected with the control unit. The communication module may collect service data of the treatment device, such as number of pulses, hardware or software errors etc. The communication module may communicate with a remote control station, e.g. server, central computer or main control center via a datalink. The datalink may be any kind of communication link, e.g. wired such as Ethernet, or wireless such as wireless internet connection, IRDC, Bluetooth, Dial-up connection, Wi-Fi, GSM, PCS. The data may be processed by a software and displayed for further analysis. The data may be displayed on mobile application. Alternatively the service data may be evaluated and any notification may be provided to the end user of the treatment device. In an exemplary application the data may correspond with treatment credits (corresponding to the treatment device or its part wear out) and it may decrease after each treatment. The treatment device may disable generating the magnetic field after running out the credits. Alternatively the treatment device may disable generating the magnetic field after reaching a predetermined number of treatments.

Alternatively the magnetic field generating device may generate a static magnetic field. The magnetic field generating device generating the static magnetic field may be e.g. permanent magnet or electromagnet. The magnetic field generating device may be powered by a power source, a transformer and/or an energy storage device. The magnetic field may be applied as time-varying magnetic field by movement of the magnetic field generating device. Alternatively the magnetic field generating device may be switched on and off.

During last few decades patient have not only wanted to be in good health, they have also wanted to look well, i.e. to be well shaped, without any unattractive fat and to have a young appearance, without wrinkles, stretchmarks or sagging breasts. This has resulted in a progressive evolution of invasive aesthetic methods such as surgical removing of fat and remodeling the human body by invasive and potentially dangerous methods, e.g. liposuction or inserting implants into human body. The side effects of invasive methods may be scars, swelling or bruising. The side effects resulted in the rapid progress in non-invasive method, e.g. lipolysis or removing skin imperfections. One example of the last few years may is rapid increase of patients' demand for enhancing the visual appearance of buttock. This has resulted in a higher percentage of these operations by plastic surgeons.

Electric current may be induced in the treated biological structure during pulsed magnetic treatment. Due to the high value of magnetic flux density the biological structure may be targeted and treated more specifically. A distribution of magnetic field is uniform in the biological structure. Particles (e.g. atoms, ions, molecules etc.) in the biological structures are influenced by the magnetic field and permeability of a cell membrane may also increase.

Due to increased permeability of the cell membrane, the pulsed magnetic field may induce following effects: at least muscle contraction; reduction of adipose tissue—volume and/or number of the adipose cells including increase of apoptotic index; intramuscular fat decrease, cellulite reduction; neogenesis and/or remodeling of collagen and/or elastin fibers, i.e. collagen and/or elastin increase; skin elasticity and/or skin texture improvement; skin tightening; waist reduction. Further magnetic treatment may improve circulation of blood and/or lymph and improve local and/or adipose tissue metabolism. Treatment by time-varying magnetic field may also cause muscle hypertrophy and/or hyperplasia; reduce diastasis recti (abdominal separation); increase fat and/or basal metabolism; and/or reduce visceral fat. The treatment effect may be known as contouring, circumferential reduction, core strengthening, body shaping, body contouring, body sculpting, core shaping, muscle forming, muscle shaping skin laxity reduction, muscle strengthening, muscle toning, muscle firming, muscle volumization, muscle tightening, e.g. butt lifting.

Repetitive application may be more efficient than standard workout in fitness since the fitness machines strengthen only the isolated muscles. The results may be achieved in very short-time periods with minimal time of treatment.

With the present methods, factors for enhancing visual appearance of the body include: treatment of major muscle, e.g. gluteus maximus; treatment of deep muscle which may be enabled by high value of magnetic flux density; non-contact application of magnetic flux density, it may be applied even through clothing; stronger muscle contraction due to higher value of magnetic flux density; higher-quality of muscle targeting; treatment may not be influenced by small movements during treatment; treatment time duration may be shortened due to high value of magnetic flux density and/or higher repetition rate; no delays may occur.

It is to be understood that the method is not limited to the particular applications and that the method may be practiced or carried out in various ways.

Present method may be applied for enhancing the visual appearance of body parts including or proximate to major muscle structures. Further the method may be applicable for enhancing the visual appearance of patients with high value of BMI. A patient with BMI of at least 18, preferably at least 25, more preferably at least 30, most preferably at least 35 or more may be preferably treated by the recited methods. A thickness of patient's SWAT and/or VWAT may be at least 0.1, 0.5, 10, 15, 25, 50, 75, 100 mm or more. The patient may be preferably healthy without any life-threatening conditions such as circulatory system disease, e.g. deep vein thrombosis. The present method is not limited to the application of the treatment to major muscle. Muscles other than major muscles may be treated as well.

The applicator of magnetic treatment may be placed proximate to the patient's body. As used here, proximate to includes both contactless and in actual contact with the skin of the patient. The actual contact with the skin of the patient may be direct contact or indirect contact. Direct contact may be the applicator contacting the skin of the patient; indirect contact may be applicator contacting the patient's skin via a spacer such as clothes, a towel or a disposable sterile cover of the applicator. The contactless application may not touch the patient's skin. Within a close proximity of the patient should be interpreter in a range from 0.1 to 50 mm from the patient's skin, more preferably in a range of 0.5 to 25 mm from the patient's skin, most preferably in a range of 1 to 10 mm from the patient's skin. Alternatively the magnetic field generating device is positioned at a distance in a range of 0.2 to 49.9 mm, more preferably in a range of 0.6 to 24.9 most preferably in a range of 1.1 to 9.9 mm from the patient's skin. The muscles may be selectively treated and the magnetic flux density may be adjusted following the patient's feeling or needs. The treatment time may be shortened due to selective treatment of the correct muscles. Additionally, due to the high value of magnetic flux density, the muscle may be treated more effectively. Further, the treatment may be non-invasive or even preferably contactless due to the high value of magnetic flux density. The patient may be treated without removing clothing, reducing patient discomfort. Additionally, following the high efficiency of the muscle contraction the collagen and/or elastin fibers above the muscle structure may be remodeled, hence the visual appearance may be enhanced.

According to exemplary application a treatment may be started by turning the magnetic treatment device on. The applicator including a magnetic field generating device may be placed on the patient. A magnetic flux density may be set up as highest magnetic flux density value acceptable by the patient. The highest magnetic flux density value acceptable by the patient may be such a value sufficient to cause a muscle contraction and may not cause pain to the patient. Further a correct treatment location may be found by an operator. The correct treatment location may be found by moving at least one applicator over the target region of the patient's body. Alternatively a plurality of applicators may be moved simultaneously in order to set up the correct treatment location. The correct treatment location is the location where the induced current causes the strongest muscle contraction. The at least one applicator may be maintained by a positioning member in a static position with respect to the patient. The positioning member may be e.g. an adjustable belt. The belt may be flexible and/or the belt may include a length adjusting member such as buckle. The treatment may be started, i.e. the time-varying magnetic field may be applied to the target region for a predetermined treatment period. The at least one applicator may be removed from the patient after lasting the treatment period. The treatment may be ended.

The position of the patient may correspond to treated biological structure and/or body region. The patient may be treated in seated position. Alternatively, the patient may be treated in lying position, e.g. in supine position. Treatment in lateral recumbent position may be also applicable. Patient may be in prone position as well.

In the preferred application the magnetic field generated by the treatment device may be applied to body regions prone to cellulite and/or prone to adipose accumulation, such as thigh, saddlebag, buttock, abdomen, region of love handle, region of bra fat, armpit fat or arm. The adipose accumulation may be influenced by number and/or volume of adipose cells. A plurality of magnetic field generating devices may apply the time-varying magnetic field to different body regions or to different locations of one large body region such as abdomen or buttock.

The magnetic field generating device may be placed in a distance up to 500 mm from the skin of the patient mm. Particularly in a range of 0.01 to 150 mm, more preferably in the range of 0.1 to 100 mm, even more preferably 1 to 50 mm, most preferably in the range of 2 to 25 mm.

The magnetic treatment of the biological structure may have various applications for enhancing visual appearance of the contour of a body region. High density magnetic field reaching such values may be used for treatment of a muscle and/or adipose tissue, wherein the adipose tissue reduction may be achieved by reduction of number and/or volume of adipose cells. Adipose tissue reduction may be also known as fat disruption, reduction or removal, skin tightening body sculpting or sculpting, connective tissue improvement or adipose tissue reduction in general.

Alternatively adipose tissue may be reduced and the muscle may gain strength. These effects may be known as contouring or circumferential reduction. Circumferential reduction refers to shape modification of body parts such as thigh or abdomen.

The adipose tissue reduction may be associated with increasing volume of the muscle. This effect may be known as core strengthening.

The adipose tissue may be reduced with improving the muscle in volume and strength. These effects may be known as cellulite treatment, body shaping, body contouring, body sculpting, core shaping, muscle forming, muscle shaping, skin laxity reduction or improving aesthetic and/or visual appearance in general.

The muscle may gain strength without adipose tissue reduction. The effect may be known as muscle strengthening, muscle toning or muscle firming.

The muscle may increase a volume. The effect may be known as muscle volumization or muscle tightening.

The muscle may be further improved in strength and in volume. Such effect may be known as muscle remodeling or stimulation, deep tissue remodeling or stimulation. This effect may be used e.g. for butt lifting.

Alternatively breast enhancement, wherein the appearance enhancement effect may be achieved by elevation or shape modification may be caused. Further lip enhancement, wherein the lip appearance enhancement may be achieved by obtaining fuller and firmer appearance. The body region may be reduced in overall size.

The muscle may be treated by a time-varying magnetic field applied by the aforementioned device.

The magnetic field may treat peripheral nerves in the treated body region. Alternatively, peripheral motor neurons affecting hundreds of muscle fibers may be selectively targeted. The muscle contraction of the whole muscle group innervated by the specific nerve or nerve plexus may be caused as well.

Due to high magnetic flux density of the generated magnetic field supramaximal muscle contractions may occur. Supramaximal contractions cannot be voluntarily achieved. The muscle may change as it naturally adapts to a muscle stress caused by the supramaximal contractions. Hence the muscle strength and/or volume may increase. The muscle strength and/or volume increase may be achieved by muscle fiber hypertrophy and/or muscle fiber hyperplasia. A muscle tension may also increase. These structural changes may be long-lasting compared to regular exercising.

Varying magnetic flux density and repetition rate resulting in the muscle contractions during the treatment may be beneficial for muscle relaxation between the muscle contractions. The treatment duty cycle may be higher than 10%, which means interrupted regime with the ratio up to 1 active to 9 passive time units. The ratio may possibly change during the therapy. In the preferred application the treatment duty cycle may be at least 15, 20, 25, 40, 50, 75, 85 or 90%.

Hence effects such muscle volumization, toning, strengthening and/or remodeling may be caused.

In the methods described, the magnetic field generating device may or may not include a magnetic core. The magnetic field generating device may be cooled by fluid, e.g. by air, water or oil. Total power consumption of the magnetic treatment device may be below 1.3 kW. A power of the magnetic treatment device may be at least 150, 250 or 500 W to generate a magnetic flux density sufficient to induce at least muscle contraction. Energy conversion efficiency may be at least 10, 25, 50, 80% or more. The energy conversion efficiency may be enabled by the above recited construction such as by using insulated wire, components layout and/or by the cooling system. A magnetic treatment device as described in the U.S. patent application Ser. No. 14/789,156 or U.S. patent application Ser. No. 14/789,658 incorporated herein by reference, may be used.

The applicator for magnetic treatment may be placed proximate to the patient's body. The magnetic flux density may be applied into the target biological structure. Electric current may be induced and treat the neuromuscular plate and/or the nerve innervating the at least one muscle fiber. The treatment may cause at least a muscle contraction.

Furthermore, the present invention discloses the advanced approaches in aesthetic applications, e.g. for cellulite treatment and/or body shaping. Combined methods of treatment by electromagnetic field and treatment by magnetic field are used. The electromagnetic field may include treatment by radiofrequency, infrared or optical waves. The magnetic treatment may be provided by permanent magnets, electromagnetic devices generating a static magnetic field or time-varying magnetic devices. In the preferred application the treatment by a pulsed magnetic field and radiofrequency treatment may be combined. However the application is not limited by the recited combination so the combined method may include magnetic treatment and any treatment by electromagnetic field, e.g. light treatment, IR treatment or treatment by radiofrequency waves, e.g. microwaves, short waves or long waves. The magnetic treatment may also be provided with one or more auxiliary treatments, for example a thermal treatment, e.g. heating and/or cooling.

A device described in U.S. patent application Ser. No. 14/278,756 incorporated herein by reference may be used for application of the present methods. The device may exclude the balun transformer, or the balun transformer may be included in transmatch. The possible methods of treatment by combined methods are described below.

Magnetic treatment in combination with radiofrequency treatment may be applied by two independent treatment devices, e.g. one device for treating the biological structure by radiofrequency waves and second device for treating the biological structure by magnetic field. Both devices may have a separate applicator for treating the biological structure, or one applicator may be used by at least two devices, i.e. the applicator may be modular for a plurality of devices.

The device may include at least one HF frequency generator for providing energy for radiofrequency treatment and for providing energy for magnetic treatment. In an alternative embodiment, the device may include at least one HF frequency generator for providing energy for radiofrequency treatment and at least one other independent frequency generator for providing energy for magnetic treatment. The device may include plurality of applicators for providing separate radiofrequency or magnetic treatments to the patient.

In alternative embodiment the applicator may provide a combination of radiofrequency and magnetic treatment. In one embodiment, the applicator may include at least one radiofrequency electrode for providing radiofrequency treatment and at least one magnetic field generating device, e.g. a magnetic field generating device, for providing magnetic treatment. In another embodiment, the applicator may include at least one electrode for providing radiofrequency treatment and at least one magnetic field generating device providing magnetic treatment, wherein the at least one RF source provides energy for both at least one electrode and at least one magnetic field generating device.

In still another embodiment the at least one RF source may provide the energy for the at least one magnetic field generating device providing magnetic treatment wherein the at least one magnetic field generating device may be used as the at least one electrode. The essence is the far different treatment frequencies which are used for RF treatment and magnetic treatment. The magnetic field generating device in the high frequency field is similar to the electrode. This enables the magnetic field generating device to be the electrode for radiofrequency treatment. In the preferred embodiment a flat magnetic field generating device may be used as the electrode.

The essential principle for this device is a fact that the energy delivery element, e.g. a magnetic field generating device such as a flat coil which may be preferably circular shaped, may administer the same function as an electrode if it is provided by the high-frequency signal. Hence the coil may be used to generate a radiofrequency treatment. The reason is that the frequency spectra of low-frequency signal used for generating the magnetic field is far different from frequency spectra of high-frequency signal used for generating the electromagnetic field. The signals from at least one or more preferably two generators may be provided successively, with some overlay or simultaneously due to difference of the frequency spectra. The frequency spectra of high-frequency signal used for generating the electromagnetic field may be in the range of ones of kHz to hundreds of GHz, more preferably in the range of 500 kHz to 3 GHz, most preferably above 1 MHz around 3.4 or 6.7 or 13.56 or 40.68 or 27.12 MHz or 434 MHz or 915 MHz or 2.45 GHz. The frequency spectra of low-frequency signal used for generating the magnetic field impulses may be in the range of 1 to 100 kHz, more preferably in the range of 1.25 to 10 kHz, even more preferably in the range of 2 to 5 kHz, most preferably in the range of 3 to 4 kHz. The low-frequency signal is used for generating impulses of time-varying magnetic field. The repetition rate of the pulses may reach up to 700 Hz, more preferably up to 500 Hz, most preferably in the range of 1 to 300 Hz. The magnetic flux density of the magnet treatment is at least 0.1 T, more preferably at least 0.5 T, even more preferably at least 1 T, even more preferably at least 1.5 T, most preferably at least 2 T, or up to 7 T on the surface of the energy delivery element. The energy delivery element may be integrated within an applicator, such as patient support for maintaining the patient in sufficiently sitting or recumbent position, e.g. a chair or a bed. The energy delivery element may be moveable within the patient support. Alternatively the applicator may be moveable, e.g. it may be attached to an articulated arm or it may be preferably hand-held.

The treatment duty cycle of 1:50 should be interpreted in the sense that one complete burst lasting a time T consists of 50 time periods T1 and the active treatment (e.g. train of pulses) of the time-varying magnetic field is applied to the patient for one time period T1, i.e., pulses of the time-varying magnetic field are not applied for 49 time periods T1. The burst may be applied repetitively. In an exemplary application the magnetic field may be applied with a repetition rate 50 Hz and with a treatment duty cycle 1:50 for 10 seconds, i.e. ten pulses of the magnetic field may be applied in a train lasting 0.2 s and no magnetic field pulse is applied for 9.8 s.

The magnetic flux density applied to active sportsmen may be higher compared to magnetic flux density applied to a patient without regular exercising.

A derivative of the magnetic flux density is defined by Equation 6.

$$\frac{dB}{dt}. \qquad \text{Eq. 6}$$

where: dB is magnetic flux density derivative [T]; dt is time derivative [s].

The maximal value of the magnetic flux density derivative may be up to 5 MT/s, preferably in the ranges of 0.3 to 800 kT/s, 0.5 to 400 kT/s, 1 to 300 kT/s, 1.5 to 250 kT/s, 2 to 200 kT/s, 2.5 to 150 kT/s, 4 to 150 kT/s, 5 to 150 kT/s. In exemplary applications the maximal value of the magnetic flux density derivative may be at least 0.3, 0.5, 1, 2.5, 3.2, 5, 8, 10, 17, 30 or 60 kT/s. The value of magnetic flux density derivative may correspond to induced current within the tissue.

The magnetic flux density derivative may be determined within entire period of the magnetic signal and/or in any segment of the magnetic signal.

Alternatively the treatment device may include no deep muscle diathermy device for heating the target biological structure. The treatment preferably may include no electrode which may enable heating the biological structure in contact mode.

Cellulite is an effect of skin change resulting in orange peel appearance. The cause of the cellulite is orientation of collagen fibers in so called "fibrous" septae. The fibrous septae contract and harden over time creating a dimple effect. Additionally, blood and lymphatic vessels lack circulation due to the contraction and hardening of the septae. The lymph flow may be blocked resulting in swelling. Another cause of cellulite may be adipose cells protruding to dermis. Cellulite may be treated by the recited methods.

One application of time-varying magnetic field for enhancing the visual appearance of body region may be treatment of a muscle by magnetic flux density for reducing the cellulite. The magnetic flux density may be delivered through the skin to the neuromuscular plate and/or nerve innervating at least one muscle fiber. The electric current may be induced in the target biological structure causing at least muscle contraction. The at least muscle contraction may cause the movement of the skin and all the biological structures subtending epidermis. Additionally, the at least muscle contraction may improve blood circulation by itself, or via the movement of the muscle in the vicinity including fibrous septae. Additionally, blood and/or lymph circulation may be improved in the layers subtending epidermis since the muscle contraction may move the fibrous septae. Also local and/or adipose tissue metabolism may be improved. The muscle contraction may move the skin above the treated muscle. A displacement of the skin may be in the range of 0.1 to 150 mm, more preferably in the range of 0.5 mm 100 mm, even more in the range of 1 to 75 mm, most preferably in the range of 2 to 50 mm. The skin displacement may last in the range of 0.01 to 30 seconds, more preferably in the range of 0.1 to 15 seconds, even more preferably in the range of 0.2 to 7.5 seconds, most preferably in the range of 0.5 to 5 seconds.

The lymph flow may be improved by at least muscle contraction which may provide effect similar to manual massage. The improved lymph flow may improve local metabolism and/or immune system. The improved lymph flow may contribute to purer lymph due to faster delivery of the lymph to the lymph nodes where the lymph may be cleared.

The present method may provide a massage effect via the treatment which may be caused by the at least muscle contraction. Therefore the massage effect may be achieved by contactless methods instead of manual massage techniques or soft tissue techniques. The massage effect may improve lymph circulation.

In another aspect, improvement of functionality and/or the appearance of the muscle may be achieved with results similar to body exercise. The results may be achieved by application of high magnetic flux density to the body region and inducing at least muscle contraction. Higher values of magnetic flux density applied may result in a stronger muscle contraction. The patient may feel firmer and tighter.

With the present method muscle contractions induced by the applied magnetic flux density may help to tone the muscle providing a more attractive appearance. As the muscle structure is treated by time-varying magnetic field the entire limb may be moved due to the high power of the magnetic treatment. Nevertheless, the method is not limited to the applications to the limbs and the method is able to treat any muscle, e.g. gluteus maximus or any muscle/deep muscle to induce body contouring and/or body shaping effect and fat burn. Additionally, shortened and/or flabby muscles may be stretched. The physical fitness of the patient may be improved as well.

The magnetic field may treat various body regions, e.g. thigh, buttock, hip, abdomen, armpit region or arm. The muscles may be shaped to enhance visual appearance of the treated body region. The body part may obtain enhanced visual appearance of its contour.

A plurality of applicators may be used for treatment of big patient and/or for treatment of pair muscles, e.g. buttock. Alternatively a plurality of applicators may be used for treatment of large treatment regions such as abdomen. Two applicators may be preferably used. Each applicator includes at least one magnetic field generating device. One applicator may be used for muscle toning.

A plurality of applicators may be placed in such position that centers of the magnetic field generating devices are in a distance in a range of 2 to 80 cm, preferably in a range of 5 to 60 cm, more preferably in a range of 10 to 50 cm, most preferably in a range of 15 to 40 cm or up to 100 cm.

A plurality of the magnetic field generating device may be used for treatment of cooperating muscles in order to enhance a visual appearance of the body region and/or to increase coordination of a movement of the body part such as a limb or an abdomen of the patient.

One exemplary cooperating muscle set may be an agonist-antagonist pair of an arm of the patient. M. biceps brachii is responsible for forearm flexion. Oppositely, m. triceps brachii is responsible for extension of the forearm. Alternatively cooperating muscles responsible for flexion/extension may be represented by hamstrings, i.e. m. biceps femoris, and m. quadriceps femoris; or m. tibialis anterior and m. triceps surae.

Alternative exemplary cooperating muscles may be left and right m. obliquus externus abdominus; or mm. pectorales and m. latissimus dorsi.

The magnetic field may treat at least one muscle of lower limb, particularly the parts which are prone to cellulite such as thighs or saddlebags. The time-varying magnetic field may induce at least muscle contraction in different muscle and/or muscle group. Following the position and/or orientation of the magnetic field generating device the anterior, posterior and/or medial compartment of the thigh may be treated. The anterior compartment includes sartorius muscle, rectus femoris muscle, vastus lateralis muscle, vastus intermedius muscle, vastus medialis muscle. Posterior compartment includes biceps femoris muscle, semitendinosus muscle and semimembranosus muscle. Medial compartment includes pectineus muscle, external obturator muscle, gracilis muscle, adductor longus muscle, adductor brevis muscle and adductor magnus muscle.

The treatment may cause circumferential reduction of thigh. Further the muscle may obtain enhanced visual appearance, thigh may be well-shaped. Thigh contour may be enhanced as well.

The at least one surrounding body region may be treated as well, e.g. buttock.

The applicator may be placed within proximity of the patient's treated area. The applicator may be fixed to the patient. Alternatively the correct position may be provided by a mechanic arm and/or adjustable applicator. The applicator may be made of adhesive and/or high friction material at least on contact surface with the patient.

The magnetic field may be generated with low repetition rate of such as 1 Hz for a predetermined period of time, e.g. 30 seconds, sufficient for setting the applicator to a correct position where the treatment is most effective. During the period the magnetic flux density may be adjusted following the patient's needs to induce muscle contraction sufficiently strong and comfortable for the patient.

The treatment may start a treatment protocol. The treatment protocol may include a set of predetermined treatment sequences consisted of predetermined repetition rates applied for a predetermined time periods. The sequences may be repeated and/or adjusted following the patient's need. The sequence may include a repetition rate in the range of 1 to 100 Hz, preferably in the range of 2 to 90 Hz, more preferably in the range of 5 to 50 Hz, most preferably in the range of 10 to 45 Hz. The sequences may last at least 30, 45, 60, 90, 120 or up to 300 seconds.

A treatment may include at least 500 magnetic pulses per one treatment, or at least 1000 magnetic pulses per one treatment are applicable as well. Alternatively the treatment may include at least 2000, preferably at least 5000, more preferably at least 10000, even more preferably at least 20000 pulses, most preferably at least 50000 pulses per one treatment. The treatment may include up to 200000 pulses per one treatment.

Alternatively the treatment may include the only the treatment protocol without applying the magnetic field of low repetition rate. The correct position of the applicator and/or adjusting the magnetic flux density may be adjusted during the first sequence of the treatment protocol.

In one application, the treatment may induce the same effect as muscle exercising of buttock. During the treatment of buttock the magnetic field may be targeted to treat of muscles shaping the buttock, e.g. tensor fasciae latae muscle or at least one of gluteal muscles: maximus, medius or minimus. In one preferred application all three gluteal muscles may be treated. Further other muscles may be treated, e.g. abdominal muscles, spinal muscles and/or thoracic muscles. By the complex treatment and muscle contraction in the body region the treated muscles may be strengthened, toned, the cellulite may be reduced and dimples may be removed. Buttock and even the patient's figure may be enhanced in visual shape appearance and may become more attractive. Buttock become well-shaped, round, firm, well-trained, toned, smoother, tight and lifted.

The complex treatment may reduce hips, make perfect round and lifted buttock, increasing the self-confidence of the patient The treatment may be more efficient than standard workout in fitness since the fitness machines strengthen only the isolated muscles. The results may be achieved in very short-time periods with minimal time of treatment. Without being limited, it is believed that the exercising of the gluteus medius may reduce the volume of the buttock; exercising of the gluteus maximus may shape and/or lift the buttock; exercising of the gluteus minimus may lift the buttock.

In the preferred application the magnetic treatment may be combined with other treatment methods using different approaches, e.g. auxiliary treatments. The combined treatment may be applied to the surroundings tissues around buttock to reduce the cellulite around the buttock and enhance the shape of the enhanced appearance of the buttock. The surrounding tissues may be represented by e.g. abdomen, love handles, thigh or saddlebags.

Combined treatment may be applied simultaneously, with overlap or separately by one or multiple treatment devices. Combined treatment may refer to application of the treatment method to the same or different body region. Combined treatment may lead to the same or different treatment effect. The example of combined treatment provided separately may be application of magnetic field to the patient followed by the application of any of auxiliary treatment methods to the patient and vice versa. The period between the applications of the combined treatment may be immediately after the first treatment up to several months. The treatment by magnetic field according to this application may follow or precede the thermal therapy of the same or different body region and to reach same or different treatment effect.

More preferably the combined therapy is applied to the same body region in order to improve the treatment effect, even more preferably the treatment effect is adipose tissue reduction and/or muscle strength and/or muscle volume increase.

The magnetic field may treat at least one muscle responsible for silhouette of the body. The time-varying magnetic field may induce at least muscle contraction in different muscle and/or muscle group responsible for silhouette in the region of abdomen, love handles and/or bra fat. Following the position and/or orientation of the magnetic field generating device rectus abdominis muscle may be treated. Alternatively latissimus dorsi muscle, abdominal internal oblique muscle, abdominal external oblique muscle, transverse abdominal muscle and/or pyramidalis muscle may be treated by the time-varying magnetic field.

The treatment may cause circumferential reduction in the region of belly, hips and/or love handles. Alternatively the treatment may tighten at least one of these body parts. Further the muscles may obtain enhanced visual appearance, belly may be well-shaped. Repetitive application may even reach in a six-pack look. The at least one surrounding body region may be treated as well, e.g. buttock.

The magnetic field may treat at least one muscle of upper limb, particularly the parts which may be prone to cellulite such as arm. The time-varying magnetic field may induce at least muscle contraction. Following the position and/or orientation of the magnetic field generating device the at least muscle contraction may occur in biceps brachii muscle, brachialis muscle, coracobrachialis muscle and/or triceps brachii muscle.

The treatment may cause circumferential reduction of the arm. Further the muscle may obtain enhanced visual appearance, arm may be well-shaped. Arm contour may be enhanced as well.

The at least muscle contraction may be more efficient for adipose tissue metabolism as the value of magnetic flux density increases since the muscle contraction may be stronger. The higher magnetic flux density may treat the higher number of muscle fibers contraction and the more adipose tissue may be reduced. Therefore the visual appearance of regions prone to cellulite may be enhanced.

Treatment by time-varying magnetic field may induce lipolysis. Adipose tissue may be reduced by decreasing the number and/or volume of adipose cells. Promoted adipose cell metabolism may increase as the value of magnetic flux density increases. The treatment may release free fatty acids (FFA) from at least one adipose cell. The increased concentration of FFA may influence a homeostasis of the adipose cell. A disruption of the homeostasis may cause a dysfunction of the adipose cell. The dysfunction may be followed by stress for endoplasmic reticulum (ER stress). ER stress may cause additional lipolysis and/or apoptosis of the at least one adipose cell.

Furthermore, ER stress may cause increase of intracellular calcium ions (Ca2+) which may promote an apoptotic process and may continue into controlled cell death of the adipose cell. The apoptosis may be induced by Ca-dependent effectors, e.g. calpain or caspase-12. Endogenous ligands or pharmacological agents, such as vitamin D, may induce prolonged cytosolic calcium increase. Vitamin D may influence release of Ca2+ from endoplasmic reticulum. Hence the effect of treatment may be enhanced by application of vitamin D and/or Ca2+ prior, during and/or after the treatment. The most significant effect may be achieved by application of both, Ca2+ and vitamin D, prior the treatment to provide all factors influencing adipose cell apoptosis.

Alternatively, increased level of Ca2+ may induce autophagy within adipose cell as well. Autophagy is self-eating process of cellular organelles to produce energy and it may proceed into cell death. Autophagy may be induced by ER stress or it may be induced via Ca2+ signaling.

Figure 9:
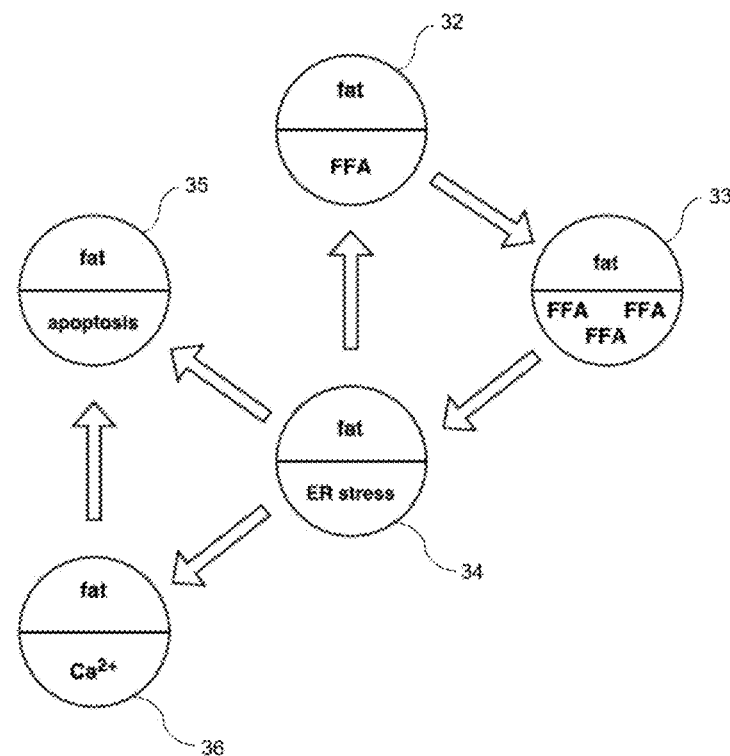
FIG. 9 is a diagram of a biological effect.

FIG. 9 illustrates pathways which may induce apoptosis of the at least one adipose cell. FFA may accumulate in the at least one adipose cell (32). The magnetic field may induce lipolysis (33), i.e. a release of FFA from adipose tissue. Accumulated FFA may reach a threshold when adipose cell is unable to utilize FFA. A dysfunction of the adipose cell may occur. The adipose cell may react on the dysfunction by ER stress (34). ER stress may induce lipolysis hence additional release of FFA may occur (32). ER stress may cause apoptosis of the adipose cell (35). Furthermore, the ER stress may release Ca2+(36) which may contribute the apoptosis (35).

The effect of the treatment by magnetic field for adipose tissue reduction may be influenced by various biological processes and/or pathways as recited above. The processes and/or pathways may be synergic hence the adipose tissue reduction may be accelerated and/or more efficient.

The method may cause the circumferential reduction i.e. a reduction of the size of the treated body region. The method may be mostly indicated for the regions with cellulite, particularly for thigh, buttock, saddlebag, love handle, armpit, abdomen, hip and/or arm. However, the indication is not limited to the mentioned regions and the method may be used for treatment of any other body region.

Furthermore, the method may change BMI index of the patient. In a preferred application the BMI of the patient may be reduced. Alternatively, the BMI of the patient may increase.

According to one application the time-varying magnetic field may be applied in various pulse sequences called protocol. The protocol may include a plurality of sections including trains and bursts. The section may include specific train duration, the burst duration or the section duration. Sections may vary in treatment parameters such as a repetition rate; a number of impulses in a train; a burst duration or a modulation of the time-varying magnetic field, i.e. changing the treatment parameters in time, alternatively the sections may be repeated or alternated. An amplitude modulation of the time-varying magnetic field may be used, i.e. a modulation in magnetic flux density. The modulation in magnetic flux density may be interpreted as changing the amplitude of the magnetic pulses in order to generate an envelope. Different envelopes are differently perceived by the patient. The treatment results may differ following the protocol. The protocol may include at least two bursts or sections which differs from each other in magnetic flux density, repetition rate or impulse duration.

The train includes a plurality of subsequent magnetic pulses, i.e. at least two magnetic pulses. Each magnetic pulse may include one biphasic impulse of the time-varying magnetic field lasting an impulse duration followed by no magnetic field lasting a first time period. Burst includes one train and a time with no magnetic field generated, or the train may be followed by a static magnetic field or a time-varying magnetic field insufficient to cause a muscle contraction. The burst may cause at least one contraction of a muscle followed by no contraction of the muscle, i.e. relaxation of the muscle may follow after the contraction of the muscle.

The train may last at least 4, 8, 25, 100, 200, 250, 300, 500, 750 ms or 1, 2, 4, 5, 7.5, 10 12.5, 15 or more seconds. The train may be in order of tens of seconds as well. The burst may last in a range of 10 ms to 100 seconds, e.g. 50, 100, 250, 500 ms or 1, 2, 5, 8, 15, 20, 30 or more seconds. An exemplary treatment may include at least 2, 5, 10, 25, 50, 100, 250 or 500 bursts. Alternatively the treatment may include a number of bursts in a range of 15 to 25000, preferably in a range of 40 to 10000, more preferably in a range of 75 to 2500, even more preferably in a range of 150 to 1500, most preferably in a range of 300 to 750 or up 100000. A time between two subsequent trains may be at least 5, 10, 50, 100, 200, 500, 750 ms. Alternatively the time between two subsequent trains may last in order of ones or tens of seconds such as 1, 2, 2.5, 5, 7.5, 10, 15, 20 seconds or more.

The protocol may include a plurality of sections. The sections may be generated sequentially. The sections may include different treatment parameters such as a repetition rate; a number of impulses in a train; a burst duration or a modulation of the time-varying magnetic field, i.e. changing the treatment parameters in time. An amplitude modulation of the time-varying magnetic field may be used, i.e. a modulation in magnetic flux density. The modulation in magnetic flux density may be interpreted as changing the amplitude of the magnetic pulses in order to generate an envelope.

The train is a group of subsequent impulses delivered to the patient. The burst includes one train and time of no magnetic field generation. The section may include a plurality of trains and/or bursts. The impulses in one train may preferably differ in magnetic flux density in order to establish a train shape. The train shape is herein after as an envelope. The section includes may include a plurality of identical trains, envelope included.

The repetition rate in the subsequent bursts may incrementally increase/decrease with an increment of at least 1, 2, 5 Hz or more. Alternatively the magnetic flux density may vary in the subsequent bursts, such as incrementally increase/decrease with an increment of at least 1, 2, 5% or more of the previous burst.

The section may include specific train duration, the burst duration or the section duration. The magnetic flux density may be modulated in amplitude to enable treatment of various envelopes. Different envelopes are differently perceived by the patient.

Trapeziodal envelope is perceived by the patient as the most comfortable. Trapeziodal envelope respects natural course of muscle contraction, i.e. the muscle contraction may be time-varying. Strength of natural muscle contraction increases, holds at the highest strength and decreases. Similarly the trapeziodal envelope corresponds with natural muscle contraction, i.e. the strength of the muscle contraction may correspond with the magnetic flux density. The magnetic flux density increases, holds and decreases.

Figure 13:
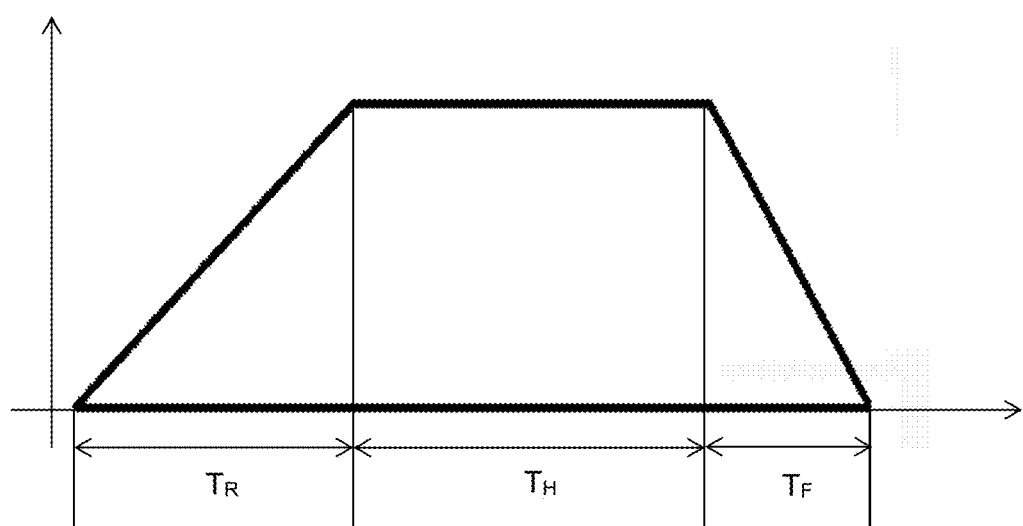
FIG. 13 illustrates an exemplary trapezoidal envelope.

FIG. 13 illustrates an exemplary trapezoidal envelope. Vertical axis may represent magnetic flux density. Horizontal axis may represent time. Trapezoidal envelope is a train of pulses, where $T_R$ is time with increasing magnetic flux density called increasing transient time, i.e. the amplitude of the magnetic flux density may increase. $T_H$ is time with maximal magnetic flux density, i.e. the amplitude of the magnetic flux density may be constant. $T_F$ is time with decreasing magnetic flux density, i.e. the amplitude of the magnetic flux density may decrease. A sum of $T_R$, $T_H$ and $T_F$ may be trapezoidal envelope duration.

The trapezoidal envelope may decrease energy consumption. The biological effect caused by trapezoidal envelope may equal to biological effect caused by a rectangular envelope. Due to lower energy consumption the trapezoidal shape may enable improved cooling of the magnetic field generating device. Further the resistive losses may be reduced due to lower temperature of the magnetic field generating device.

Different repetition rate may cause different type of muscle contraction. Each type of muscle contraction may consume different energy.

Figure 14:
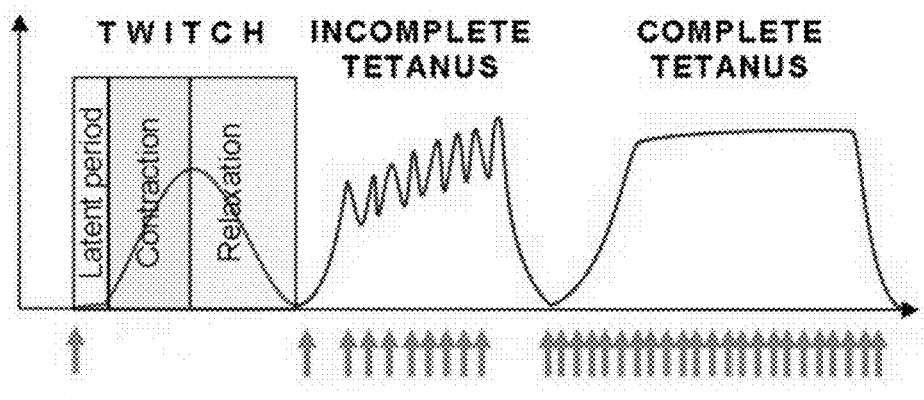
FIG. 14 illustrates types of muscle contraction.

FIG. 14 illustrates different types of muscle contraction. The muscle contraction may differ in energy consumption. Vertical axis may represent a strength of the muscle contraction. Horizontal axis may represent time. Arrows may represent magnetic pulses applied to the muscle of the patient.

Low repetition rate of the time-varying magnetic field pulses, e.g. 1, 2, 5 or up to 15 Hz, may cause a twitch. Low repetition rate may be sufficiently low to enable the treated muscle to fully relax. The energy consumption of the treated muscle may be low due to low repetition rate.

Intermediate repetition rate of the time-varying magnetic field pulses, e.g. 15, 20, 25 or up to 29 Hz, may cause incomplete tetanus muscle contraction. Incomplete tetanus may be defined by a repetition rate in a range of 10 to 30 Hz. The muscle may not fully relax. The muscle may be partially relaxed. The muscle contraction strength may increase with constant magnetic flux density applied.

Higher repetition rate of the time-varying magnetic field pulses, e.g. 30, 35, 40 Hz or higher up to 90 Hz, may cause complete tetanus muscle contraction. The complete tetanus muscle contraction may cause the strongest supramaximal muscle contraction. The supramaximal muscle contraction may be stronger than volitional muscle contraction. The energy consumption may be higher. The strengthening effect may be improved. Further, it is believed that at repetition rates of at least 30 Hz the adipose cells may be reduced in volume and/or in number.

Even higher repetition rate of the time-varying magnetic field pulses over 90 Hz may suppress and/or block pain excitement transmission at different levels or neural system and/or pain receptors. The repetition rate may be preferably at least 100 Hz, more preferably at least 120 Hz, most preferably at least 140 Hz. The application of time-varying magnetic field to the muscle of the patient may cause pain relief effect.

High repetition rate of the time-varying magnetic field pulses over 120 Hz may relieve a tonus of the muscle. The repetition rate may be preferably at least 150 Hz, more preferably at least 180 Hz, most preferably at least 200 Hz. The application of the time-varying magnetic field to the muscle of the patient may cause myorelaxation effect.

A quality of the muscle contraction caused by the time-varying magnetic field may be characterized by parameters such as a contractile force of the muscle contraction, a muscle-tendon length, a relative shortening of the muscle or a shortening velocity of the muscle.

The contractile force of the muscle contraction may reach a contractile force of at least 0.1 N/cm$^2$ or up to 250 N/cm$^2$. The contractile force may be in a range of 0.5 to 200 N/cm$^2$, more preferably in the range of 1 to 150 N/cm$^2$, most preferably in the range of 2 to 100 N/cm$^2$.

The muscle-tendon length may reach up to 65% of a rest muscle-tendon length. The muscle-tendon length may be preferably in a range of 1 to 60% of the rest muscle-tendon length, more preferably in a range of 3 to 55% of the rest muscle-tendon length, most preferably in a range of 5 to 50% of the rest muscle-tendon length.

The muscle may be shortened during the muscle contraction up to 60% of a rest muscle length. The muscle shortening may be in a range of 0.1 to 50% of the rest muscle length, more preferably in the range of 0.5 to 40% of the rest muscle length, most preferably in the range of 1 to 25% of the resting muscle length.

The muscle may shorten at a velocity of up to 10 cm/s. The muscle shortening velocity may be preferably in a range of 0.1 to 7.5 cm/s, more preferably in the range of 0.2 to 5 cm/s, most preferably in the range of 0.5 to 3 cm/s.

According to one application, a time-varying magnetic field may be applied to the patient in order to cause a muscle shaping effect by muscle contraction. The muscle may obtain increased tonus and/or volume. Strength of the muscle may increase as well.

The application may be intended for muscle treatment. The treatment by repetition rate up to 45 Hz may provide significant treatment results in muscle shredding effect. The muscle shaping protocol may include three sections of different repetition rates and time durations.

First section may include a repetition rate in a range of 10 to 30 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 250 to 1000 ms. After the magnetic flux density reaches the maximal value the magnetic flux density may be maintained at the maximal acceptable value for a time in a range of 0.75 to 2.5 seconds. Then the magnetic flux density may decrease to zero for a time in a range of 0.5 to 1.5 seconds. Afterward the relaxation period may follow for a time in a range of 1 to 5 seconds, i.e. no time-varying magnetic field may be applied to the patient. The total time duration of the burst may be in a range of 2.5 to 10 seconds. The section duration may be 30 to 150 seconds.

First section may be used for preparing the muscle for the following section. The section may heat up the muscle. Further the blood circulation may be improved to provide enough energy and/or oxygen to the treated muscle.

Second section may include a repetition rate in a range of 20 to 40 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 250 to 1000 ms. After the magnetic flux density reaches the maximal value the magnetic flux density may be maintained at the maximal acceptable value for a time in a range of 1 to 3 seconds. Then the magnetic flux density may decrease to zero for a time in a range of 0.5 to 1.5 seconds. Afterward the relaxation period may follow for a time in a range of 1 to 7 seconds, i.e. no magnetic field may be applied to the patient. The total time duration of the burst may be in a range of 2.75 to 12.5 seconds. The section duration may be in a range of 50 to 250 seconds.

The second section includes higher repetition rate than the first section. The higher repetition rate may enable stronger muscle contraction of the treated muscle. The supramaximal muscle contraction may cause improved muscle shaping effect. Further the time duration of maximal magnetic flux density application is longer with respect to the first section. The longer and/or the stronger the muscle contraction the improved muscle shaping effect may be caused. On the other hand the longer and/or the stronger the muscle contraction the more lactate may be formed. The longer relaxation period may be required during the second section compared to first section, i.e. the time-varying magnetic field is not applied to the patient.

Third section may include a repetition rate in a range of 2 to 6 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 0.5 to 1.5 seconds. After the magnetic flux density reaches the maximal value the magnetic flux density may be maintained at the maximal acceptable value for a time on a range of 0.5 to 1.5 seconds. Then the magnetic flux density may decrease to zero for a time in range 2.5 to 7.5 seconds. Afterward the period of no applying the magnetic field to the patient may follow for a time in a range of 3 to 12 seconds. The total time duration may be in a range 6 to 22 seconds. The section duration may be in a range of 30 to 110 seconds.

The third section may be used for muscle relaxation. Relaxation section is important to enable long lasting treatment without exhausting the treated muscle. The relaxation section may prevent a lactate accumulation and muscle pain after the treatment. The relaxation section may cause massage effect. The relaxing section may include the lower repetition rate and the longest relaxation period. Further the relaxation section may extend the treatment time and increase the treatment results.

The treatment may include a plurality of sections. The sections may be repeatedly applied to the patient for a time in a range of 10 to 240 minutes, more preferably in a range of 15 to 120 minutes, most preferably in a range of 30 to 60 minutes at maximal magnetic flux density at maximal acceptable value by the patient. According to exemplary application the sections may be applied to the patient in a range of three to ten times within one treatment.

According to another application the time-varying magnetic field may be applied to the patient in order to cause muscle shaping effect by muscle contraction and a reduction of adipose cells. The muscle may obtain increased tonus and/or volume. Strength of the muscle may increase as well. The adipose cells may be reduced in number and/or volume.

The application may be intended for adipose cells reduction, intramuscular fat decrease and for the muscle treatment. The combined protocol may include three sections of different repetition rates and time durations.

The application may begin with a repetition rate suitable for causing strong muscle contractions in order to heat up the treated muscles in very short time duration in order to burn glycogen.

First section may include a repetition rate in a range of 20 to 40 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 250 to 1000 ms. After the magnetic flux density reaches the maximal value the magnetic flux density may be maintained at the maximal acceptable value for 0.5 to 2 seconds. Then the magnetic flux density may decrease to zero for a time in a range of 0.75 to 4 seconds. Afterward the relaxation period may follow for a time in a range of 1 to 5 seconds, i.e. no time-varying magnetic field may be applied to the patient. The total time duration of the burst may be in a range of 2.5 to 12 seconds. The section duration may be in a range of 40 to 200 seconds.

First section may be used for strong muscle contraction of the treated muscle. The supramaximal muscle contraction may cause improved muscle shaping effect. Further short time duration of maximal magnetic flux density application may provide improved blood perfusion of the muscle. The section duration may be sufficiently long to shred the treated muscle.

Second section may include a repetition rate of 30 to 60 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range 0.25 to 1000 ms. After the magnetic flux density reaches the maximal value the magnetic flux density may be maintained at the maximal acceptable value for a time in a range of 2 to 5 seconds. Then the magnetic flux density may decrease to zero for a time in a range of 0.5 to 2 seconds. Afterward the relaxation period may follow for a time in a range of 2 to 10 seconds, i.e. no magnetic field may be applied to the patient. The total time duration of the burst may be in a range of 5 to 15 seconds. The section duration may be in a range of 35 to 150 seconds.

The second section includes higher repetition rate than the first section. It is believed that the repetition rate up to 30 Hz may result in muscle forming. The repetition rate over 30 Hz may result in adipose cells reduction due to increased energy consumption of the treated muscle to sustain the supramaximal muscle contraction. The increased energy consumption may result in a metabolism of adipose cells. The adipose cells may be reduced by number and/or volume. Time duration of maximal magnetic flux density application is longer with respect to the first section. The longer and/or the stronger the muscle contraction the more adipose cells may be reduced. On the other hand the longer and/or the stronger the muscle contraction the more lactate may be formed. The longer relaxation period may be required during the second section compared to first section, i.e. the time-varying magnetic field is not applied to the patient.

Third section may include a repetition rate in a range of 2 to 8 Hz. The maximal magnetic flux density may be maintained at maximal acceptable value which may be perceived by the patient. Trains may be modulated in magnetic flux density to a trapezoidal envelope. The trapezoidal envelope may include increasing transient time duration of a time in a range of 0.25 to 1.5 seconds. After the magnetic flux density reaches the maximal value the magnetic flux density may be maintained at the maximal acceptable value for a time in a range of 0.25 to 2.5 seconds. Then the magnetic flux density may decrease to zero for a time in a range of 2 to 8 seconds. Afterward the period of no applying the magnetic field to the patient may follow for a time in a range of 3 to 10 seconds. The total time duration of the burst may be in a range of 5 to 20 seconds. The section duration may be in a range of 50 to 250 seconds.

The third section may be used for muscle relaxation. Relaxation section may enable long lasting treatment without exhausting the treated muscle. The relaxation section may prevent a lactate accumulation and muscle pain after the treatment. Further the relaxation section includes applying the time-varying magnetic field to the muscle of the patient with repetition rate in a range of 2 to 8 Hz. The relaxation may be active relaxation. The muscle may be relaxed and the metabolism may not be immediately stopped. The relaxation section may cause massage effect. The relaxing section may include the lower repetition rate and the longest relaxation period. Further the relaxation section may extend the treatment time and increase the treatment results.

The treatment may include a plurality of sections. The sections may be repeatedly applied to the patient for a time in a range of 10 to 240 minutes, more preferably in a range of 15 to 120 minutes, most preferably in a range of 30 to 60 minutes at maximal magnetic flux density at maximal acceptable value by the patient. According to exemplary application the sections may be applied to the patient six times within one treatment.

The maximal magnetic flux density of the train may be maintained at maximal acceptable value during the treatment for at least 10 minutes, more preferably around 30 minutes. On the other hand the maximal magnetic flux density of the train may be maintained below maximal acceptable value during the treatment longer than 30 minutes, more preferably up to 240 minutes. It may be recommended to maintain the maximal magnetic flux density of the train in a range of 80 to 95% of the maximal acceptable value by the patient in order to prevent exhaustion of the treated muscle. The longer the treatment the improved treatment effect may be caused.

The glycogen storage may decrease in short time duration due to supramaximal muscle contractions. The first section may be used for causing the muscle shredding effect and also for promoting energy consumption in order to start the adipose cell metabolism. The second section is believed to activate adipose cells metabolism in order to reduce the adipose cells in number and/or volume. The first and the second sections may demand high energy consumption of the treated muscle.

The time-varying magnetic field may be applied to the patient by one applicator. A plurality of applicators may also be used. In an exemplary embodiment two applicators may be used for treating large body regions such as abdomen. Alternatively two applicators may be used for treating lateral muscles such as muscles of buttock or thigh.

The magnetic field may be applied to the patient's in a sequence for muscle shaping. The muscle shaping effect may be preferably used for tightening thigh of the patient, increasing volume of a buttock, lifting the buttock and/or shredding abdominal muscles of the patient. The applicator including the magnetic field generating device may contact the patient in a body region on transversal circumference of the patient's body between rib-cage and popliteal fossa. Alternatively the applicator may be placed above another muscle to be shredded, toned and/or volumized.

Shaping a buttock may be caused by application the time-varying magnetic field to the muscles of buttock or surrounding muscles, e.g. tensor fasciae latae muscle or at least one of gluteal muscles: maximus, medius or minimus. In one preferred application all three gluteal muscles may be treated. By the complex treatment and supramaximal muscle contraction of buttock the muscles are strengthened, toned, the cellulite may be reduced and dimples may be removed. Buttock and even the patient's figure may be enhanced in visual shape appearance and become more attractive. Buttock become well-shaped, round, firm, well-trained, toned, smoother, tight and lifted. The complex treatment may reduce hips, make perfect round and lifted buttock, increasing the self-confidence of the patient. Without being limited, it is believed that the exercising of the gluteus medius may reduce the volume of the buttock; exercising of the gluteus maximus may shape and/or lift the buttock; exercising of the gluteus minimus may lift the buttock. Furthermore, the gluteal muscles may grow as well.

The gluteal muscles are inervated by n. gluteus inferior and n. gluteus superior. Further m. piriformis is innervated by n. plexus sacralis. The magnetic field generating device may by placed within proximity of the patient over medial part of m. piriformis. All muscles of patient's buttocks may be treated in such a position of the magnetic field generating device.

Figure 15:
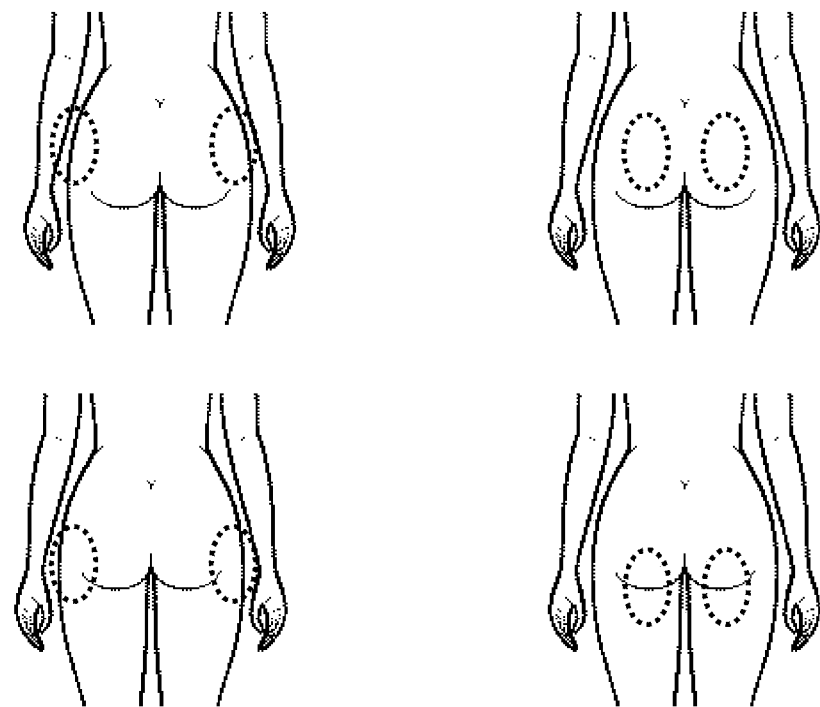
FIG. 15 illustrate exemplary applications for buttock treatment.

In an exemplary application the magnetic field may be applied to the buttock. The applicators may be placed in four regions of the buttock. The buttock may be divided into four regions. FIG. 15 illustrates exemplary regions for placing the applicator. The magnetic field generating devices are represented by dotted ovals on the patient's body. Each region may treat specific muscles in order to enable tailor made application following the patient's need. The applicator may be placed to the region. In a preferred application the applicator including the magnetic field generating device may be placed on the patient between gluteal fold and iliac crest. The applicator may be attached to the patient by a length adjustable positioning member such as belt. The buttock may become firm, toned and/or round shaped.

Further abdominal muscles may be treated, e.g. rectus abdominis muscle, external oblique muscle, internal oblique muscle or transversus abdominis muscle. Rectus abdominis muscle is innervated by nn. intercostale and n. subcostalis. Exemplary placing of the magnetic field generating device may be over abdominal area down from the costae towards the pelvis. External and internal oblique muscle and transversus abdominis muscle are innervated by nn. intercostales, n. subcostalis, n. iliohypogastricus, n. ilioinguinalis, n.genitofemoralis. The treatment may improve abdominal tone, strengthen abdominal muscle and/or increase abdominal firmness.

Figure 16:
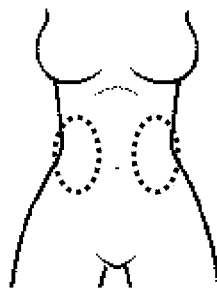
FIG. 16 illustrates an exemplary application for abdomen treatment.

At least one applicator including at least one magnetic field may be placed in contact with the patient between rib-cage and pelvis of the patient. Alternatively the applicator may be placed in a body region between sternum and anterior superior iliac spine. The applicator may be laterally shifted. Exemplary placement of the magnetic field generating device may be between costae and crista iliaca superior and/or pubic bone. An optimal placement of the magnetic field generating device may be determined by moving the magnetic field generating device towards m. rectus abdomis in order to cause the strongest muscle contraction. The muscles of abdomen become toned, shredded and/or well-shaped. The strength of the treated muscles increases as well. The volume of the gluteal muscle may increase as well. FIG. 16 illustrates exemplary placing of the applicators.

In an exemplary application the magnetic field may be applied to the abdomen of the patient. The applicator may be placed preferably caudally from the lowest ribs of the patient in a distance up to 10 cm from the center of the magnetic field generating device. The location down of the ribs may be well accepted by the patient. The applicator may not touch the ribs of the patient. Discomfort caused by the pressure applied to the ribs by the applicator may be reduced. Alternatively the magnetic field generating devices may be shifted in lateral direction.

In a preferred application two applicators may be placed on the patient and fixed by a positioning member, e.g. belt. The two applicators may be placed laterally on the patient. In an alternative application a plurality of the magnetic field generating devices may be within one applicator covering the abdominal area. The magnetic field generating devices may be moveable within the applicator.

The application of the time-varying magnetic field to the abdominal region may increase an apoptotic index for at least 5% with respect to an apoptotic index prior to treatment. The apoptotic index may be increased by the treatment of the abdominal region in a range of 50 to 400%, preferably in a range of 60 to 250%, more preferably in a range of 75 to 175%, most preferably in a range of 90 to 150%, or up to 600%. Further repeating the treatment method may decrease a fat layer thickness for at least 0.1%, preferably in a range of 0.5 to 60%, more preferably in a range of 1 to 50%, even more preferably in a range of 2 to 40%, most preferably in a range of 3 to 30% or up to 75% in the abdominal region. Further the abdominal muscles may increase a cross-section thickness for at least 0.1%, preferably in a range of 0.5 to 50%, more preferably 1 to 35%, even more preferably in a range of 2 to 30%, most preferably in a range of 3 to 25% or up to 75%. Furthermore, diastasis of abdominal muscles such as rectus abdominis may be reduced up to 50%, preferably in a range of 1 to 30%, more preferably 2 to 35%, most preferably in a range of 3 to 30%. Moreover the repetitive treatment may cause a circumferential reduction of abdominal region and/or waist. The circumferential reduction may be at least 0.5 cm, preferably at least 1 cm, more preferably at least 2 cm, even more preferably at least 3 cm, most preferably at least 5 cm or up to 25 cm. Alternatively the circumferential reduction may be at least 1%, preferably at least 2%, more preferably at least 4%, even more preferably at least 8%, most preferably around 10% or up to 15% of the circumferential length prior the first treatment.

Further the muscles of thigh may be treated, e.g. tensor fascia latae muscle, vastus lateralis muscle or iliotibial muscle. The thigh may obtain lifted appearance and/or the contour may be improved. The saddlebacks may be reduced as well. The treatment may cause thigh strengthening, toning and/or firming.

One exemplary application of the time-varying magnetic field for causing the muscle contraction may be placing the magnetic field generating device over m. quadriceps femoris innervated by n. femoralis. The magnetic field generating device may be placed within proximal end of the m. quadriceps femoris. The magnetic field generating device may be placed in distal direction to popliteal fossa.

Alternative exemplary application of thigh treatment may be application of time-varying magnetic field to m. biceps femoris, m. semimembranosus and/or semitendinosus (so called hamstrings) innervated by n. ischiadicus and n. tibialis. The magnetic field generating device may be placed within close proximity of gluteal sulcus, the so called gluteal fold. The magnetic field generating device may be placed in distal direction.

In an alternative application, muscles of calf may be treated by the time-varying magnetic field, .e.g m. triceps surae innervated by n. tibialis. One exemplary placement of the magnetic field generating device may be close to popliteal fossa. Alternatively the magnetic field generating device may be placed in distal direction.

In an alternative application, an arm of the patient may be treated by the time-varying magnetic field. The treatment may tone, firm and/or strengthen the muscles of arm. Flexors of the arm, e.g. m. biceps brachialis or m. coracobrachialis innervated by n. musculocutaneus, may be treated by the magnetic field generated by the magnetic field generated device placed on anterior side of the arm in a proximal direction from m. deltoideus. Extensors of the arm, e.g. m. triceps brachii or m. anconeus innervated by n. radialis, may be treated by a magnetic field generating device placed on the posterior side of the arm in a proximal direction from m. deltoideus. The magnetic field generating device may be placed at a distal end of the muscle.

In an alternative application, muscles of a forearm of the patient may be treated by the time-varying magnetic field. The muscles of the forearm are innervated by n. radialis, n. medialis and/or n. ulnaris. The magnetic field generating device may be placed proximally from the elbow. The magnetic field generating device may be placed at a distal end of the muscles.

Alternatively muscles in region of bra fat may be treated by the time-varying magnetic field, e.g. muscles latissimus dorsi, infraspinatus, supraspinatus, trapezius, rhomboid major/minor, teres major and/or minor, serratus anterior, pectoralis major and/or minor. The magnetic field may be applied to a dorsal body region between crista iliaca superior and scapula included. Alternatively the magnetic field may be applied to a ventral body region between clavicle, sternum, rib VI and crista tuberculi majoris humeri. An armpit fat may be reduced as well.

In an alternative application, pectoral muscles innervated by nn. Pectorals laterales or mediales may be treated. An exemplary application may be placing the magnetic field generating device to subclavicular area in order to treat mm. pectorales minors. Alternatively placing the magnetic field generating device to parasternal area may treat mm. pectorales majors. The magnetic field generating device may be placed proximal to the sternum of the patient.

Alternatively, neck muscles may also treated by applying the time-varying magnetic field to the suprascapular region. The applicator may be also placed in a cranial direction above clavicle. The treatment may cause submental tightening and/or platysma tightening. Neck rejuvenation may be caused as well.

Alternatively, head muscles such as facial muscles may be treated by time-varying magnetic field. One exemplary application may be treatment of m. buccalis, orbicularis oris or oculi etc. The treatment may cause facial rejuvenation.

The treatment is more efficient than standard workout in fitness since the machines strengthen only the isolated muscles and/or muscles groups. The results may be achieved in very short-time periods with minimal time of treatment.

In the preferred application the magnet treatment may be combined with other treatment methods using different approaches, e.g. auxiliary treatments. The combined treatment may be applied to the surroundings tissues around buttock to reduce the cellulite around the buttock and enhance the shape of the enhanced appearance of the buttock. The surrounding tissues may be represented by e.g. abdomen, love handle, thigh or saddle bag.

According to another application the time-varying magnetic field may be applied to the patient in order to cause muscle shaping effect by muscle contraction and a reduction of adipose cells. The muscle may obtain increased tonus and/or volume. Strength of the muscle may increase as well.

The treatment may be used for improvement of a region of pelvic floor and/or surrounding tissues such as female genital tissue including vulva and vagina. The muscle in proximity of vagina may be toned or tightened. The vagina may be tightened as well. Further the sexual arousal may be improved due to the tightened muscles. Similar effect may be caused in male population. The muscles of pelvic floor may be strengthened and erectile function may be improved.

The combined protocol may include three sections of different repetition rates and time durations.

First section may include a repetition rate in a range of 90 to 150 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 1 to 5 seconds. After the magnetic flux density reaches the maximal value the magnetic flux density may be maintained at the maximal acceptable value for a time in a range of 1 to 5 seconds. Then the magnetic flux density may decrease to zero for a time in a range of 1 to 5 seconds. Afterward the relaxation period may follow for a time in a range of 1 to 5 seconds, i.e. no time-varying magnetic field may be applied to the patient. The total time duration of the burst may be in a range of 4 to 20 seconds. The section duration may be in a range of 10 to 50 seconds.

First section may be used for preparing the muscle for the following section. The section may heat up the muscles. Further the blood circulation may be improved to provide enough energy and/or oxygen to the treated muscle. The repetition rate in the range of 90 to 150 Hz modulated in magnetic flux density may be well-accepted by the patient. It may be comfortable for the patient due to pain relieving effect of repetition rates over 80 Hz. Further the muscle may be contracted as complete tetanic muscle contraction.

Second section may include repetition rates in a range of 10 to 45 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 1 to 5 seconds. After the magnetic flux density reaches the maximal value the magnetic flux density may be maintained at the maximal acceptable value for a time in a range of 1 to 5 seconds. Then the magnetic flux density may decrease to zero for a time in a range of 1 to 5 seconds. Afterward the relaxation period may follow for a time in a range of 1 to 5 seconds, i.e. no magnetic field may be applied to the patient. The total time duration of the burst may be in a range of 4 to 20 seconds. The section duration may be in a range of 60 to 300 seconds. The repetition rates may vary after one cycle of the section, e.g. first cycle may include the repetition rate in a range of 15 to 25 Hz, second cycle may include the repetition rate in a range of 20 to 30 Hz and third cycle may include the repetition rate in a range of 25 to 40 Hz.

The second section includes lower repetition rate than the first section. The lower repetition rate may enable stronger muscle contraction of the treated muscle. The supramaximal muscle contraction may cause improved muscle shaping effect. Further the time duration of the second section is longer with respect to the first section. Further the different repetition rates may cause different muscle contraction. Thy muscle contraction may vary from incomplete to complete tetanus muscle contraction. The longer relaxation period may be required during the second section compared to first section, i.e. the time-varying magnetic field is not applied to the patient.

Third section may include a repetition rate up to 2 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 1 to 5 seconds. After the magnetic flux density reaches the maximal value the magnetic flux density may be maintained at the maximal acceptable value for a time in a range of 1 to 5 seconds. Then the magnetic flux density may decrease to zero for a time in a range of 1 to 5 seconds. Afterward the period of no applying the magnetic field to the patient may follow for a time in a range of 1 to 5 seconds. The total time duration of the burst may be in a range of 4 to 20 seconds. The section duration may be in a range of 15 to 200 seconds.

The third section may be used for muscle relaxation. Relaxation section is important to enable long lasting treatment without exhausting the treated muscle. The relaxation section may prevent a lactate accumulation and muscle pain after the treatment. The relaxation section may cause massage effect. The relaxing section may include the lower repetition rate and the longest relaxation period. The repetition rate up to 2 Hz causes effect similar to manual massage. The twitch may provide high quality relaxation to the treated muscle. Further the relaxation section may extend the treatment time and increase the treatment results.

The treatment may include a plurality of sections. The sections may be repeatedly applied to the patient for a time in a range of 10 to 240 minutes, more preferably in a range of 15 to 120 minutes, most preferably in a range of 30 to 60 minutes at maximal magnetic flux density at maximal acceptable value by the patient. According to exemplary application the sections may be applied to the patient three to ten times within one treatment.

First section may include a repetition rate in a range of 80 to 180 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 250 to 1000 ms. After the magnetic flux density reaches the maximal value the magnetic flux density may be maintained at the maximal acceptable value for 0.5 to 2 seconds. Then the magnetic flux density may decrease to zero for a time in a range of 0.75 to 4 seconds. Alternatively the envelope may be rectangular for a time period in a range of 1.5 to 7 seconds, i.e. with no modulation. Afterward the relaxation period may follow for a time in a range of 1 to 5 seconds, i.e. no time-varying magnetic field may be applied to the patient. The total time duration of the burst may be in a range of 2.5 to 12 seconds. The section duration may be in a range of 40 to 200 seconds.

First section may be used for temporary pain relief effect. The temporary pain relief effect may enable applying higher magnetic flux density during the following sections. The rectangular envelopes may cause effect similar to muscle blood pump.

Second section may include a repetition rate of 30 to 60 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range 0.25 to 1000 ms. After the magnetic flux density reaches the maximal value the magnetic flux density may be maintained at the maximal acceptable value for a time in a range of 2 to 5 seconds. Then the magnetic flux density may decrease to zero for a time in a range of 0.5 to 2 seconds. Afterward the relaxation period may follow for a time in a range of 2 to 10 seconds, i.e. no magnetic field may be applied to the patient. The total time duration of the burst may be in a range of 5 to 15 seconds. The section duration may be in a range of 35 to 150 seconds.

The second section includes lower repetition rate than the first section. It is believed that the repetition rate up to 30 Hz may result in muscle forming. The repetition rate over 30 Hz may result in adipose cells reduction due to increased energy consumption of the treated muscle to sustain the supramaximal muscle contraction. The increased energy consumption may result in a metabolism of adipose cells. The adipose cells may be reduced by number and/or volume. Time duration of maximal magnetic flux density application is longer with respect to the first section. The longer and/or the stronger the muscle contraction the more adipose cells may be reduced. On the other hand the longer and/or the stronger the muscle contraction the more lactate may be formed. The longer relaxation period may be required during the second section compared to first section, i.e. the time-varying magnetic field is not applied to the patient.

Third section may include a repetition rate in a range of 150 to 250 Hz. The maximal magnetic flux density may be maintained at 25, 50 or 75% of the maximal acceptable value which may be perceived by the patient. Trains may be not be modulated. The rectangular envelope may be applied to the patient for a time period in a range of 5 to 10 seconds. Afterward the period of no applying the magnetic field to the patient may follow for a time in a range of 3 to 10 seconds. The total time duration of the burst may be in a range of 8 to 20 seconds. The section duration may be in a range of 50 to 250 seconds.

The third section may be used for muscle relaxation. Relaxation section may enable long lasting treatment without exhausting the treated muscle. The high repetition rate may cause high quality muscle relaxation effect for the treated muscle. Further the relaxation section may extend the treatment time and increase the treatment results.

A group of the second and the third section may be repeated for three times to 15 times.

Fourth section may include a repetition rate in a range of 2 to 10 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 0.5 to 1.5 seconds. After the magnetic flux density reaches the maximal value the magnetic flux density may be maintained at the maximal acceptable value for a time on a range of 0.5 to 1.5 seconds. Then the magnetic flux density may decrease to zero for a time in range 2.5 to 7.5 seconds. Afterward the period of no applying the magnetic field to the patient may follow for a time in a range of 3 to 12 seconds. Alternatively the magnetic field may be applied to the muscle as a train of pulses of repetition rate in a range 1 to 5 Hz for a period in a range of 10 to 30 seconds. The total time duration may be in a range 6 to 30 seconds. The section duration may be in a range of 30 to 110 seconds.

The fourth section may be used for muscle relaxation. Relaxation section is important to enable long lasting treatment without exhausting the treated muscle. The relaxation section may prevent a lactate accumulation and muscle pain after the treatment. The relaxation section may cause massage effect. The relaxing section may include the lower repetition rate and the longest relaxation period. Further the relaxation section may extend the treatment time and increase the treatment results.

The treatment may include a plurality of sections. The sections may be repeatedly applied to the patient for a time in a range of 10 to 240 minutes, more preferably in a range of 15 to 120 minutes, most preferably in a range of 30 to 60 minutes at maximal magnetic flux density at maximal acceptable value by the patient. According to exemplary application the sections may be applied to the patient in a range of three to ten times within one treatment.

First section may include a repetition rate in a range of 80 to 150 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 250 to 1000 ms. After the magnetic flux density reaches the maximal value the magnetic flux density may be maintained at the maximal acceptable value for 0.5 to 2 seconds. Then the magnetic flux density may decrease to zero for a time in a range of 0.75 to 4 seconds. Alternatively the envelope may be rectangular for a time period in a range of 1.5 to 7 seconds, i.e. with no modulation. Afterward the relaxation period may follow for a time in a range of 1 to 5 seconds, i.e. no time-varying magnetic field may be applied to the patient. The total time duration of the burst may be in a range of 2.5 to 12 seconds. The section duration may be in a range of 40 to 200 seconds.

The first section may be used for temporary pain relief effect. The temporary pain relief effect may enable applying higher magnetic flux density during the following sections. The rectangular envelopes may cause effect similar to muscle blood pump.

Second section may include a repetition rate in a range of 2 to 10 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 0.5 to 1.5 seconds. After the magnetic flux density reaches the maximal value the magnetic flux density may be maintained at the maximal acceptable value for a time on a range of 0.5 to 1.5 seconds. Then the magnetic flux density may decrease to zero for a time in range 2.5 to 7.5 seconds. Afterward the period of no applying the magnetic field to the patient may follow for a time in a range of 3 to 12 seconds. Alternatively the magnetic field may be applied to the muscle as a train of pulses of repetition rate in a range 1 to 5 Hz for a period in a range of 10 to 30 seconds. The total time duration may be in a range 6 to 30 seconds. The section duration may be in a range of 30 to 110 seconds.

The second section may be used for muscle relaxation. The relaxation section may cause massage effect. The relaxing section may include the lower repetition rate and the longest relaxation period.

Third section may include a repetition rate of 30 to 60 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range 0.25 to 1000 ms. After the magnetic flux density reaches the maximal value the magnetic flux density may be maintained at the maximal acceptable value for a time in a range of 2 to 5 seconds. Then the magnetic flux density may decrease to zero for a time in a range of 0.5 to 2 seconds. Afterward the relaxation period may follow for a time in a range of 2 to 10 seconds, i.e. no magnetic field may be applied to the patient. The total time duration of the burst may be in a range of 5 to 15 seconds. The section duration may be in a range of 35 to 150 seconds.

The third section includes higher repetition rate than the second section. It is believed that the repetition rate up to 30 Hz may result in muscle forming. The repetition rate over 30 Hz may result in adipose cells reduction due to increased energy consumption of the treated muscle to sustain the supramaximal muscle contraction. The increased energy consumption may result in a metabolism of adipose cells. The adipose cells may be reduced by number and/or volume. Time duration of maximal magnetic flux density application is longer with respect to the first section. The longer and/or the stronger the muscle contraction the more adipose cells may be reduced. On the other hand the longer and/or the stronger the muscle contraction the more lactate may be formed. The longer relaxation period may be required during the second section compared to first section, i.e. the time-varying magnetic field is not applied to the patient.

Fourth section may include a repetition rate in a range of 20 to 40 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 250 to 1000 ms. After the magnetic flux density reaches the maximal value the magnetic flux density may be maintained at the maximal acceptable value for 0.5 to 2 seconds. Then the magnetic flux density may decrease to zero for a time in a range of 0.75 to 4 seconds. Afterward the relaxation period may follow for a time in a range of 1 to 5 seconds, i.e. no time-varying magnetic field may be applied to the patient. The total time duration of the burst may be in a range of 2.5 to 12 seconds. The section duration may be in a range of 40 to 200 seconds.

The fourth section may be used for strong muscle contraction of the treated muscle. The supramaximal muscle contraction may cause improved muscle shaping effect. Further short time duration of maximal magnetic flux density application may provide improved blood perfusion of the muscle. The section duration may be sufficiently long to shred the treated muscle.

A group of the third and the fourth section may be repeated for three to 15 times.

Fifth section may include a repetition rate in a range of 80 to 150 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 250 to 1000 ms. After the magnetic flux density reaches the maximal value the magnetic flux density may be maintained at the maximal acceptable value for 0.5 to 2 seconds. Then the magnetic flux density may decrease to zero for a time in a range of 0.75 to 4 seconds. Alternatively the envelope may be rectangular for a time period in a range of 1.5 to 7 seconds, i.e. with no modulation. Afterward the relaxation period may follow for a time in a range of 1 to 5 seconds, i.e. no time-varying magnetic field may be applied to the patient. The total time duration of the burst may be in a range of 2.5 to 12 seconds. The section duration may be in a range of 40 to 200 seconds.

The fifth section may be used for muscle regeneration after the treatment. The section may heat up the muscle. Further the blood circulation may be improved to provide enough energy and/or oxygen to the treated muscle.

Sixth section may include a repetition rate in a range of 80 to 150 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 250 to 1000 ms. After the magnetic flux density reaches the maximal value the magnetic flux density may be maintained at the maximal acceptable value for 0.5 to 2 seconds. Then the magnetic flux density may decrease to zero for a time in a range of 0.75 to 4 seconds. Alternatively the envelope may be rectangular for a time period in a range of 1.5 to 7 seconds, i.e. with no modulation. Afterward the relaxation period may follow for a time in a range of 1 to 5 seconds, i.e. no time-varying magnetic field may be applied to the patient. The total time duration of the burst may be in a range of 2.5 to 12 seconds. The section duration may be in a range of 40 to 200 seconds.

The sixth section including the repetition rate over 80 Hz may relieve a muscle tonus and/or relax the muscle. Further the section may improve local perfusion and/or metabolism. The short rectangular envelopes may cause effect similar to muscle blood pump. The increasing magnetic flux density may increase efficiency of the muscle blood pump.

The treatment may include a plurality of sections. The sections may be repeatedly applied to the patient for a time in a range of 10 to 240 minutes, more preferably in a range of 15 to 120 minutes, most preferably in a range of 30 to 60 minutes at maximal magnetic flux density at maximal acceptable value by the patient. According to exemplary application the sections may be applied to the patient in a range of three to ten times within one treatment.

According to another application the time-varying magnetic field may be applied to the patient in order to cause muscle shaping effect by muscle contraction and a reduction of adipose cells. The muscle may obtain increased tonus and/or volume. Strength of the muscle may increase as well. The adipose cells may be reduced in number and/or volume.

The protocol may include a plurality of repetition rate of different biological effect. The protocol may combine repetition rate in a range of 25 to 75 Hz and repetition rates over 80 Hz. The repetition rates in the range of 25 to 75 Hz may cause a muscle contraction. The muscle contraction may be used for muscle strengthening. On the other hand, repetition rates over 80 Hz, such as 100, 120 and higher may be used for causing pain relief and/or myorelaxation effect.

The combined protocol may include three sections of different repetition rates and time durations.

According to another application the protocol may include a plurality sections.

In general the protocol may include a plurality of section. The protocol may be used for muscle strengthening, toning.

First section may include a repetition rate in a range of 80 to 150 Hz. The magnetic flux density may be maintained at least at 25%, more preferably 50%, even more preferably 75% or more of the maximal acceptable value which may be perceived by the patient. Trains may not be modulated, i.e. the envelope may be rectangular. The train duration may be in a range of 1 to 1000 ms, more preferably in a range of 5 to 500 ms, even more preferably in a range of 10 to 100 ms, most preferably in a range of 15 to 45 ms. Afterward the relaxation period may follow for a time period in a range of 2 to 2500 ms, more preferably in a range of 10 to 1200 ms, even more preferably in a range of 20 to 250 ms, most preferably in a range of 35 to 155 ms, i.e. no time-varying magnetic field may be applied to the patient. The total time duration of the burst may be in a range of 3 to 3500 ms, more preferably in a range of 15 to 1700 ms, even more preferably in a range of 30 to 350 ms, most preferably in a range of 50 to 200 ms. The section duration may be in a range of 3 to 10 seconds or up to 30 seconds. The section may be preferably repeated at least twice, more preferably 5 times or up to ten times. The magnetic flux density may preferably increase in the following sections.

The first section including repetition rate over 80 Hz may relieve a muscle tonus and/or relax the muscle. Further the section may improve local perfusion and/or metabolism. The short rectangular envelopes may cause effect similar to muscle blood pump. The increasing magnetic flux density may increase efficiency of the muscle blood pump. The first section may prepare the treated muscle for treatment by the protocol.

Second section may include a repetition rate in a range of 10 to 30 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 0.5 to 2 seconds. After the magnetic flux density reaches the maximal value the magnetic flux density may be maintained at the maximal acceptable value for a time a range of 0.5 to 2 seconds. Then the magnetic flux density may decrease to zero for a time a range of 0.5 to 2 seconds. Afterward the relaxation period may follow for a time a range of 1 to 5 seconds, i.e. no magnetic field may be applied to the patient. The total time duration of the burst may be in a range of 2.5 to 10 seconds. The section duration may be in a range of 30 to 120 seconds. The section may be preferably repeated at least twice, more preferably at least 5 times or up to 10 times. The repetition rate may increase within following sections such as 25, 30, 40 or 45 Hz.

The second section includes lower repetition rate than the first section. Further the second section may include higher treatment duty cycle than the first section. The lower repetition rate, higher treatment duty cycle and/or the section duration may enable stronger muscle contraction of the treated muscle. The supramaximal muscle contraction may cause improved muscle strengthening and/or toning effect. Further the time duration of maximal magnetic flux density application is longer with respect to the first section. The longer and/or the stronger the muscle contraction the improved muscle shaping effect may be caused. On the other hand the longer and/or the stronger the muscle contraction the more lactate may be formed. The longer relaxation period may be required during the second section compared to first section, i.e. the time-varying magnetic field is not applied to the patient. The section may maintain the treatment duty cycle at least 10%, more preferably at least 25%, most preferably at least 50% in order to enabled appropriate muscle relaxation.

Third section may include a repetition rate up to 2 Hz. The maximal magnetic flux density may be maintained at maximal acceptable value which may be perceived by the patient. The time duration of the third section may be in a range of 30 to 120 seconds.

The third section may be used for muscle relaxation. The relaxation section may prevent a lactate accumulation and muscle pain after the treatment. The relaxation section may cause massage effect. The relaxing section may include the lower repetition rate. Further the relaxation section may extend the treatment time and increase the treatment results.

A plurality of second sections and third section may be repeated in order to establish the complete treatment protocol. The total protocol duration may be 30 minutes.

The treatment may include a plurality of sections. The sections may be repeatedly applied to the patient for a time in a range of 10 to 240 minutes, more preferably in a range of 15 to 120 minutes, most preferably in a range of 30 to 60 minutes at maximal magnetic flux density at maximal acceptable value by the patient. According to exemplary application the sections may be applied to the patient six times within one treatment.

The protocol may shorten the time duration of the treatment. The number of the patients treated may increase.

According to another application the time-varying magnetic field may be applied to the muscle of the patient include preferably a repetition rate over 80 Hz to provide pain relief effect.

A treatment protocol may include four sections. The section may be repeated within one treatment.

First section may include a repetition rate in a range of 80 to 150 Hz. The magnetic flux density may be maintained at least at 25%, more preferably 50%, even more preferably 75% or more of the maximal acceptable value which may be perceived by the patient. Trains may not be modulated, i.e. the envelope may be rectangular. The train duration may be in a range of 15 to 45 ms. Afterward the relaxation period may follow for a time period in a range of 35 to 155 ms, i.e. no time-varying magnetic field may be applied to the patient. The total time duration of the burst may be in a range of 50 to 200 ms. The section duration may be in a range of 3 to 10 seconds. The section may be preferably repeated at least twice, more preferably 5 times or up to ten times. The magnetic flux density may preferably increase in the following sections.

The first section including repetition rate in a range of 80 to 150 Hz may relieve a muscle tonus and/or relax the muscle. The repetition rate in the range of 80 to 150 Hz may cause a pain relief effect. Further the section may improve local perfusion and/or metabolism. The short rectangular envelopes may cause effect similar to muscle blood pump. The increasing magnetic flux density may increase efficiency of the muscle blood pump. The first section may prepare the treated muscle for treatment by the protocol.

Second section may include a repetition rate in a range of 10 to 30 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 0.5 to 2 seconds. After the magnetic flux density reaches the maximal value the magnetic flux density may be maintained at the maximal acceptable value for a time in a range of 0.5 to 2 seconds. Then the magnetic flux density may decrease to zero for a time in a range of 0.5 to 2 seconds. Afterward the relaxation period may follow for a time in a range of 2 to 10 seconds, i.e. no magnetic field may be applied to the patient. The total time duration of the burst may be in a range of 3 to 15 seconds. The section duration may be in a range of 30 to 150 seconds.

The second section may be repeated with the repetition rate in a range of 15 to 45 Hz. The increased repetition rate may increase the effect of muscle contraction. The muscle may be strengthened. The local perfusion may increase as well. The different repetition rate may improve the treatment results.

The second section includes lower repetition rate than the first section. Further the second section may include higher treatment duty cycle than the first section. The lower repetition rate, higher treatment duty cycle and/or the section duration may enable stronger muscle contraction of the treated muscle. The supramaximal muscle contraction may cause improved muscle strengthening and/or toning effect. The relaxation period in a range of 1 to 5 seconds may sufficiently relax the treated muscle.

Third section may include a repetition rate in a range of 30 to 60 Hz. The maximal magnetic flux density may be maintained in a range of 40 to 100%, more preferably in a range of 60 to 90%, most preferably around 80% of the maximal acceptable value which may be perceived by the patient for a time period in a range of 0.1 to 2 seconds. Relaxation period in the range of 0.1 to 2 seconds may follow, i.e. no magnetic field may be applied to the patient. The total time duration of the burst may be in a range of 0.2 to 4 seconds. The section duration may be in a range of 0.5 to 30 seconds.

The third section includes higher repetition rate than the first section. Further the third section may include higher treatment duty cycle than the second section. The higher repetition rate and/or higher treatment duty cycle may enable stronger muscle contraction of the treated muscle. The section duration may not exhaust the treated muscle. The supramaximal muscle contraction may cause improved muscle strengthening and/or toning effect. The magnetic flux density decreasing for a time period in a range of 1.5 to 4.5 seconds may enable to relieve the muscle tonus continually. The relaxation period in a range of 2 to 8 seconds may sufficiently relax the treated muscle.

A benefit of such the protocol may be suppressing the pain threshold in order to enable treat the muscle by higher magnetic flux density. The muscle may gain higher strength due to applied higher magnetic flux density.

Further benefit of the protocol may be short time duration of the protocol. The protocol may enable to combine different protocols due to treatment time reduction.

Further the present methods may be used for treatment of disease of urogenital and/or digestive tract, e.g. improvement of circulation and/or trophic problems, faecal incontinence, urinal incontinence (stress or urge), neuromuscular dysfunction of bladder, mixed incontinence, sexual dysfunction, priapism, erectile dysfunction, orgasmic disorder, fertility issues, chronic pelvic pain syndrome, pain in pelvic area, hyperplasia of prostate, prostatitis, prostatodynia syndrome, dysmenorrhea, vulvodynia, pain and other conditions associated with menstrual cycle, menopausal and/or postmenopausal disorders, cystitis (such as interstitial), inflammatory disease of uterus or cervix uteri, parametris, peritonitis, vaginitis, vulvitis, endometriosis, genital prolapse, hemorrhoids, peripheral paresis or pelvic floor issues in general. The present methods may be used for muscle strengthening, muscle relaxation, regeneration after childbirth (such as pelvic floor prolapse), vaginal tightening or scar treating. Alternatively the treatment may improve postoperative tissue healing such as scars or wounds.

According to another application the time-varying magnetic field may be applied to the muscle of the patient include preferably a repetition rate over 80 Hz to provide pain relief effect.

First section may include a repetition rate in a range of 80 to 150 Hz. The magnetic flux density may be maintained at least at 25%, more preferably 50%, even more preferably 75% or more of the maximal acceptable value which may be perceived by the patient. Trains may not be modulated, i.e. the envelope may be rectangular. The train duration may be in a range of 1 to 1000 ms, more preferably in a range of 5 to 500 ms, even more preferably in a range of 10 to 100 ms, most preferably in a range of 15 to 45 ms. Afterward the relaxation period may follow for a time period in a range of 2 to 2500 ms, more preferably in a range of 10 to 1200 ms, even more preferably in a range of 20 to 250 ms, most preferably in a range of 35 to 155 ms, i.e. no time-varying magnetic field may be applied to the patient. The total time duration of the burst may be in a range of 3 to 3500 ms, more preferably in a range of 15 to 1700 ms, even more preferably in a range of 30 to 350 ms, most preferably in a range of 50 to 200 ms. The section duration may be in a range of 3 to 10 seconds or up to 30 seconds. The section may be preferably repeated at least twice, more preferably 5 times or up to ten times. The magnetic flux density may preferably increase in the following sections.

The first section including repetition rate over 80 Hz may relieve a muscle tonus and/or relax the muscle. Further the section may improve local perfusion and/or metabolism. The short rectangular envelopes may cause effect similar to muscle blood pump. The increasing magnetic flux density may increase efficiency of the muscle blood pump. The first section may prepare the treated muscle for treatment by the protocol.

Second section may include a repetition rate in a range of 150 to 250 Hz. The maximal magnetic flux density may be maintained at 25, 50 or 75% of the maximal acceptable value which may be perceived by the patient. Trains may be not be modulated. The rectangular envelope may be applied to the patient for a time period in a range of 5 to 10 seconds. Afterward the period of no applying the magnetic field to the patient may follow for a time in a range of 3 to 10 seconds. The total time duration of the burst may be in a range of 8 to 20 seconds. The section duration may be in a range of 50 to 250 seconds.

The second section may be used for muscle relaxation. Relaxation section may enable long lasting treatment without exhausting the treated muscle. The high repetition rate may cause high quality muscle relaxation effect for the treated muscle. Further the relieved tonus may cause pain relief effect.

Third section may include a repetition rate in a range of 2 to 10 Hz. The maximal magnetic flux density may be maintained at maximal acceptable value which may be perceived by the patient. Trains may be modulated in magnetic flux density to a trapezoidal envelope. The trapezoidal envelope may include increasing transient time duration in a range of 0.5 to 1.5 seconds. After the magnetic flux density reaches the maximal value the magnetic flux density may be maintained at the maximal acceptable value for a time on a range of 0.5 to 1.5 seconds. Then the magnetic flux density may decrease to zero for a time in range 2.5 to 7.5 seconds. Afterward the period of no applying the magnetic field to the patient may follow for a time in a range of 3 to 12 seconds. Alternatively the magnetic field may be applied to the muscle as a train of single pulses of repetition rate in a range 1 to 5 Hz for a period in a range of 10 to 30 seconds. The total time duration may be in a range 6 to 30 seconds. The section duration may be in a range of 30 to 110 seconds.

The third section may be used for muscle relaxation. The relaxation section may prevent a lactate accumulation and muscle pain after the treatment. The relaxation section may cause massage effect and/or improve local blood circulation.

Fourth section may include a repetition rate in a range of 150 to 250 Hz. The maximal magnetic flux density may be maintained at 25, 50 or 75% of the maximal acceptable value which may be perceived by the patient. Trains may be not be modulated. The rectangular envelope may be applied to the patient for a time period in a range of 5 to 10 seconds. Afterward the period of no applying the magnetic field to the patient may follow for a time in a range of 3 to 10 seconds. The total time duration of the burst may be in a range of 8 to 20 seconds. The section duration may be in a range of 50 to 250 seconds.

The fourth section may be used for muscle relaxation. The high repetition rate may cause high quality muscle relaxation effect for the treated muscle. Further the relieved tonus may cause pain relief effect.

Fifth section may include a repetition rate in a range of 80 to 150 Hz. The magnetic flux density may be maintained at least at 25%, more preferably 50%, even more preferably 75% or more of the maximal acceptable value which may be perceived by the patient. Trains may not be modulated, i.e. the envelope may be rectangular. The train duration may be in a range of 1 to 1000 ms, more preferably in a range of 5 to 500 ms, even more preferably in a range of 10 to 100 ms, most preferably in a range of 15 to 45 ms. Afterward the relaxation period may follow for a time period in a range of 2 to 2500 ms, more preferably in a range of 10 to 1200 ms, even more preferably in a range of 20 to 250 ms, most preferably in a range of 35 to 155 ms, i.e. no time-varying magnetic field may be applied to the patient. The total time duration of the burst may be in a range of 3 to 3500 ms, more preferably in a range of 15 to 1700 ms, even more preferably in a range of 30 to 350 ms, most preferably in a range of 50 to 200 ms. The section duration may be in a range of 3 to 10 seconds or up to 30 seconds. The section may be preferably repeated at least twice, more preferably 5 times or up to ten times. The magnetic flux density may preferably increase in the following sections.

The fifth section including repetition rate over 80 Hz may relieve a muscle tonus and/or relax the muscle. Further the section may improve local perfusion and/or metabolism. The short rectangular envelopes may cause effect similar to muscle blood pump. The increasing magnetic flux density may increase efficiency of the muscle blood pump.

The continual application of the magnetic field to the muscle of the patient may be up to 10 seconds, more preferably up to 5 seconds. It should be interpreted in the sense that a train of subsequent magnetic pulses applied to the muscle of the patient may be up to 10 seconds. In a preferred application a treatment duty cycle may be used.

The magnetic treatment may be combined with one or more auxiliary treatments, e.g. treatment by optical waves.

Combined applications of optical waves and magnetic field may be used. The optical treatment may include treatment by optical waves. The magnet treatment may be provided by permanent magnets, electromagnetic devices generating a static magnetic field or preferably by magnetic devices generating time-varying magnetic field. In the preferred application the method may combine treatment by a pulsed magnetic field and optical treatment. The application is not limited by the recited combination so the combined method may include magnetic treatment and any treatment by electromagnetic field such as radiofrequency waves, e.g. microwaves, short waves or long waves.

The basic parts of the optical irradiation system to apply the methods of the present invention include a hardware panel and an optical waves generating device or multiple optical waves generating devices.

The optical waves generating device may be arranged in a pattern such as an array or a matrix. The optical waves generating devices may be attached to each other or alternatively be individually mounted on dedicated supports. A scanning system may also be one of the options.

An optical treatment device may include at least one energy source and/or connection to the energy source, a hardware panel for controlling the optical treatment device and an optical waves generating device. Non limiting examples of optical waves generating device that may be used include coherent or non-coherent optical waves generating devices, light emitting diodes, lasers, laser diodes, different types of lamps and filtered lamps or combinations thereof. The treatment device may include at least one optical waves generating device, more preferably a plurality of optical waves generating devices of wavelength from ultraviolet, visible and infrared spectrum ranges. The wavelength may be in the range of 190 to 13000 nm, preferably in the range of 290 to 3000 nm, more preferably in the range of 400 to 1500 nm, even more preferably in the range of 550 to 1450 nm, particularly wavelengths about 915, 1064, 1208 and 1715 nm may be used.

Optical waves may be monochromatic or polychromatic. Optical waves may be applied in pulses with pulse duration in the range of 0.1 µs to 10000 ms, more preferably in the range of 1 µs to 5000 ms, even more preferably in the range of 2 µs to 2500 ms, most preferably in the range of 5 µs to 1000 ms.

Energy flux provided by light may be in the range of 0.005 to 500 $W/cm^2$, more preferably in the range of 0.01 to 150 $W/cm^2$ and most preferably in the range of 0.1 to 120 $W/cm^2$.

The plurality of optical waves generating devices may generate the optical waves simultaneously at the same time. The plurality of generated optical waves may interfere. Alternatively the plurality of optical waves generating devices may generate a plurality of independent optical waves in different time, preferably in sequences. The plurality of optical waves generating devices may be arranged in a predefined pattern within an applicator, e.g. in an array or a matrix.

The optical waves generating device may be preferably external (e.g. hand-held), alternatively the optical treatment applicator may be integral part of the optical treatment device (e.g. chair/bed implemented). Additionally, optical delivery element, such as optical waveguides, light tubes or optical gel, may be used.

The at least one magnetic field generating device and the at least one optical waves generating device may be mutually oriented in one common plane. Alternatively the at least one magnetic field generating device and the at least one optical waves generating device may be in two planes which may be parallel, perpendicular or mutually tilted. The planes may rotate.

The at least one magnetic field generating device and at least one optical waves generating device may include a common focus spot, i.e. the time-varying magnetic field and the optical waves may be applied to the common area. The focus spot size may be in the range of 0.001 $cm^2$ to 600 $cm^2$, more preferably in the range of 0.005 $cm^2$ to 300 $cm^2$, most preferably in the range of 0.01 $cm^2$ to 100 $cm^2$.

According to one exemplary embodiment the at least one magnetic field generating device may be surrounded by the at least one optical waves generating device. The at least one optical waves generating device may be tilted with respect to the magnetic field generated device or vice versa. The focus spot may be established by applying the magnetic field and optical waves simultaneously and/or separately.

The magnetic field generating device and the optical waves generating device may have common center with respect to the applicator and/or to the patient. Alternatively the distance between the center of magnetic field generating device and the center of optical waves generating device may be in a range of 0.01 to 500 mm, more preferably in a range of in the range of 0.1 to 250 mm, even more preferably in the range of 1 to 100 mm, most preferably in a range of 5 to 50 mm.

An area of all optical waves generating devices may be in the range of 4 to 7900 $cm^2$, preferably in the range of 9 to 1950 $cm^2$, more preferably in the range of 15 to 975 $cm^2$, most preferably in the range of 45 to 450 $cm^2$.

The area of the magnetic field generating device and the area of optical waves generating device may differ. The area of the optical waves generating device may in a range of 2 to 2000% of the area of the magnetic field generating device, more preferably in the range of 5 to 1000%, even more preferably in the range of 10 to 500% of the area of the magnetic field generating device, most preferably in the range of 25 to 250% of the area of the magnetic field generating device.

According to one exemplary embodiment the magnetic treatment and optical treatment may be provided by at least two separate devices, i.e. at least one device for administering the magnetic treatment and at least one device for administering the optical treatment. The optical treatment may be applied to target biological structure prior, after or with some overlay with magnetic treatment. Alternatively optical treatment may be applied simultaneously with magnetic treatment. The time sequences of the treatments are described below.

Figure 17:
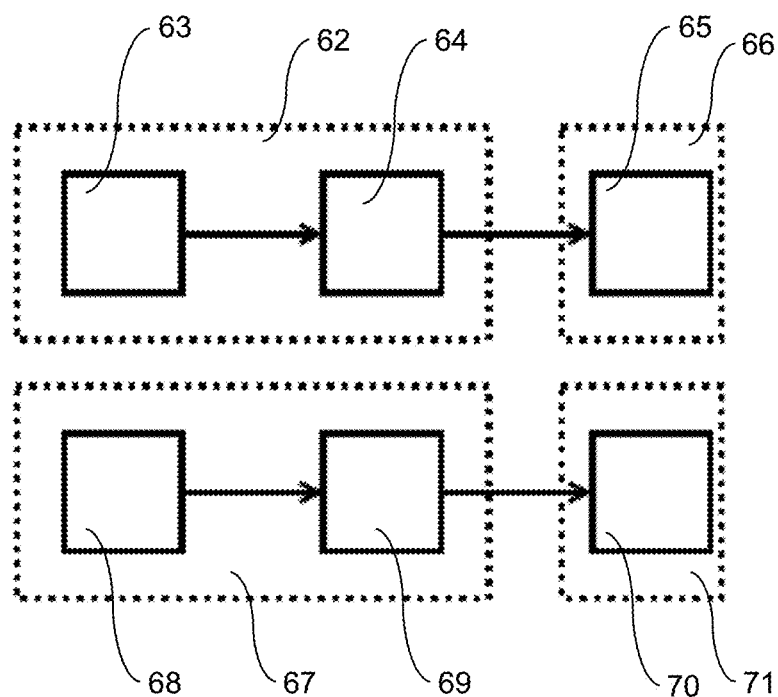
FIG. 17 illustrates a combined treatment administered by two separate devices.

FIG. 17 illustrates an exemplary embodiment providing combined treatment by magnetic field and optical treatment. The optical treatment may be replaced by any auxiliary treatment methods. The optical treatment may be administered by optical treatment device 62 (dotted line) including a connection to an energy source 63 and a hardware panel 64 for controlling the optical treatment. The hardware panel 64 may be connected with optical waves generating device 65 within an optical treatment applicator 66 (dotted line). The magnetic treatment may be administered by magnetic treatment device 67 (dotted line) including a connection to an energy source 68 and a hardware panel 69 for controlling the treatment by magnetic field. The hardware panel 69 may be connected with magnetic field generating device 70 within a magnetic treatment applicator 71 (dotted line).

In an alternative embodiment the at least one optical waves generating device may be in the treatment device. The optical waves may be delivered to the applicator and/or to the target biological structure by a waveguide.

Figure 18A:
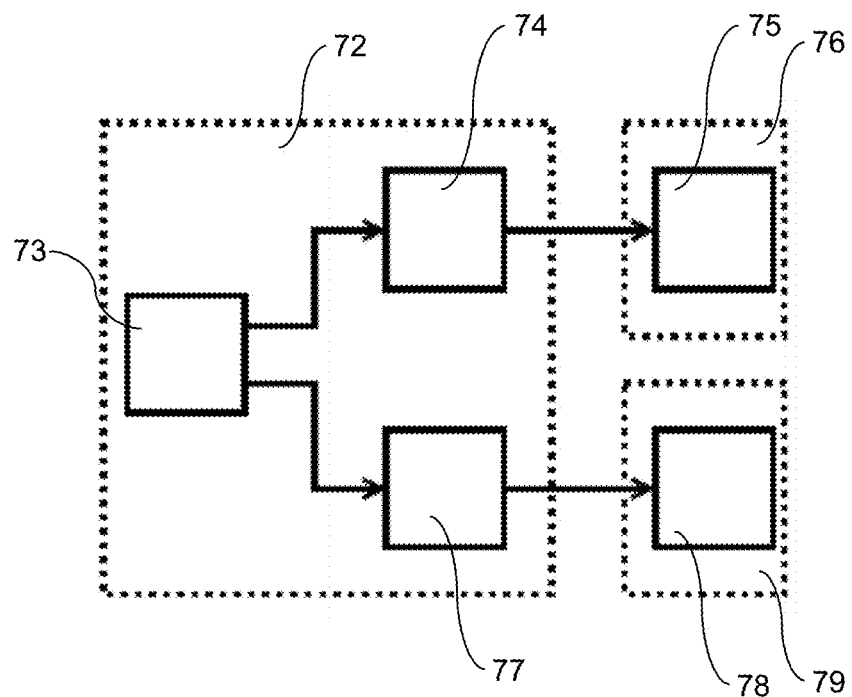
FIGS. 18a and 18b illustrate a combined treatment administered by one device including a plurality of applicators comprising magnetic field generating device or optical waves generating device.
Figure 18B:
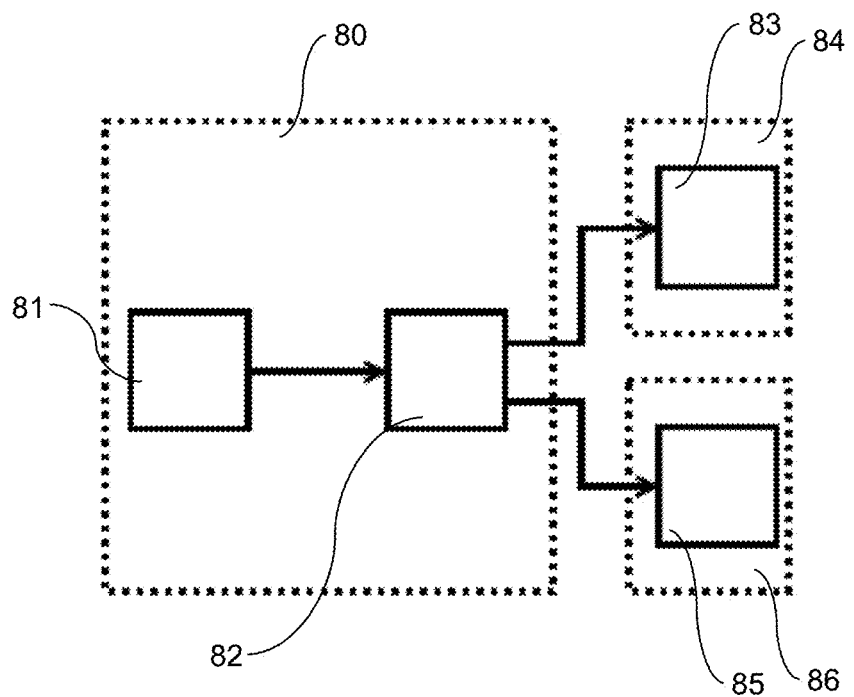
Figure 19A:
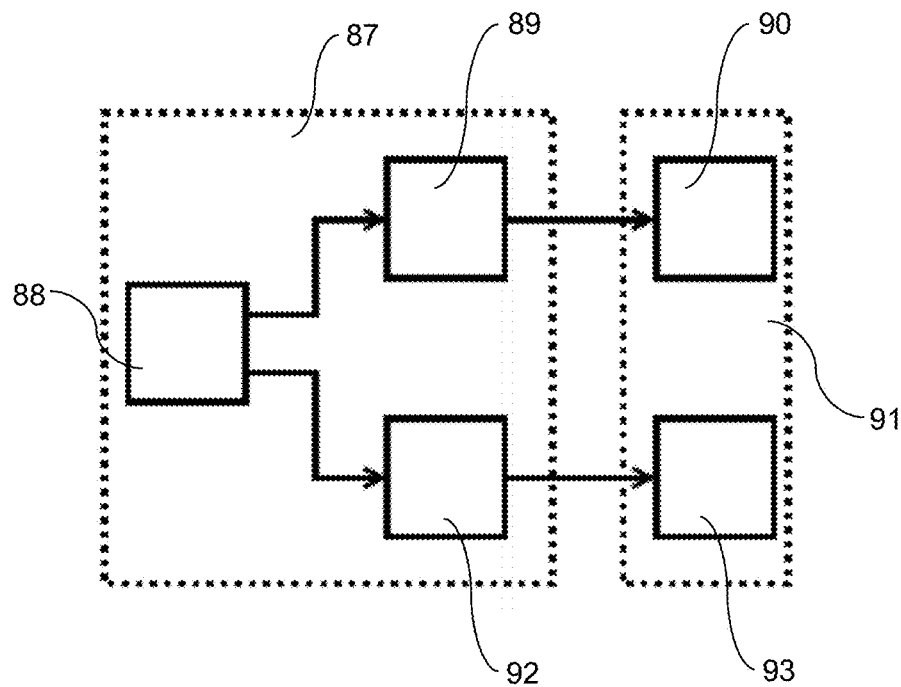
FIGS. 19a and 19b illustrate a combined treatment by one device including one applicator comprising at least one magnetic field generating device and at least one optical waves generating device.
Figure 19B:
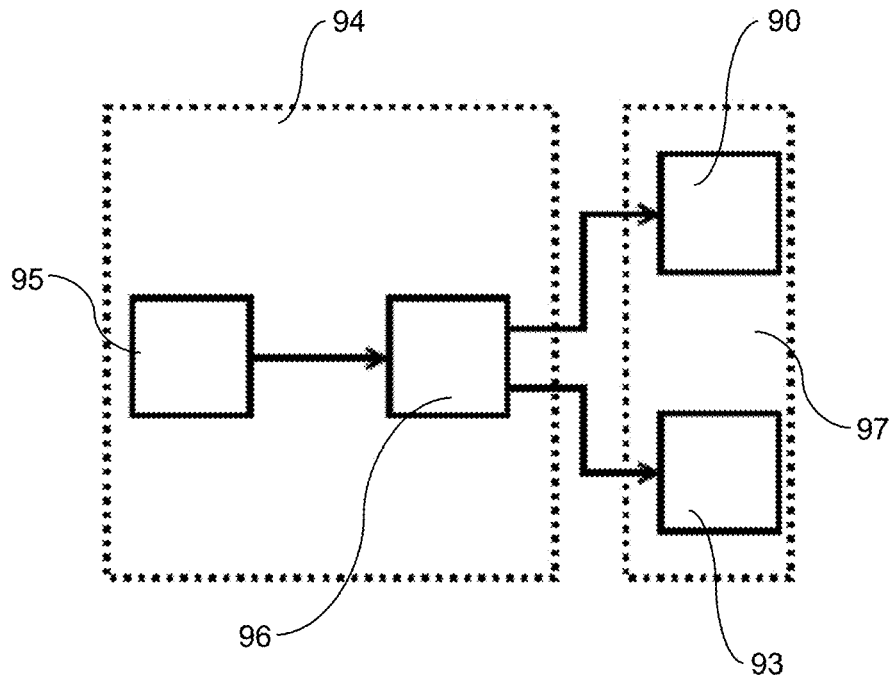

According to another embodiment the magnetic treatment and optical treatment may be provided by one device. The optical treatment may be replaced by any auxiliary treatment methods. The combined treatment provided by one device may be administered by at least one applicator. FIGS. 18*a* and 18*b* illustrate exemplary embodiments providing the combined treatment by two applicators providing different types of treatment, i.e. magnetic and optical treatment, to the patient. FIGS. 19*a* and 19*b* illustrate exemplary embodiments providing the combined treatment by one applicator providing magnetic and/or optical treatment to the patient.

FIG. 18*a* illustrates one exemplary embodiment of combined treatment device providing magnetic and/or optical treatment by at least two applicators. The combined treatment device 72 (dotted line) may include a connection to an energy source 73 providing energy for a magnetic treatment and for an optical treatment. The optical treatment may be controlled by a hardware panel for optical treatment 74 which may control an optical waves generating device 75 within an optical treatment applicator 76 (dotted line). The magnetic treatment may be controlled by a hardware panel for magnetic treatment 77 which controls a magnetic field generating device 78 within a magnetic treatment applicator 79 (dotted line).

In an alternative embodiment the at least one optical waves generating device may be in the combined treatment device. The optical waves may be delivered to the applicator and/or to the target biological structure by a waveguide.

FIG. 18*b* illustrates another exemplary embodiment of the combined treatment device providing magnetic and/or optical treatment by at least two applicators. The combined treatment device 80 (dotted line) may include a connection to an energy source 81 providing energy for the magnetic treatment and/or for the optical treatment. Optical and/or magnetic treatment may be controlled by a hardware panel 82. The hardware panel 82 may control an optical waves generating device 83 within an optical treatment applicator 84 (dotted line). Further the hardware panel 82 may control a magnetic field generating device 85 within a magnetic treatment applicator 86 (dotted line).

In an alternative embodiment the at least one optical waves generating device may be in the treatment device. The optical waves may be delivered to the applicator and/or to the target biological structure by a waveguide. Alternatively the optical treatment may be replaced by any auxiliary treatment methods.

FIG. 19*a* illustrates still another exemplary embodiment of the combined treatment device providing magnetic and/or optical treatment by at least one applicator. The combined treatment device 87 (dotted line) may include a connection to an energy source 88 providing energy for the magnetic treatment and/or for the optical treatment. The optical treatment may be controlled by a hardware panel for optical treatment 89 which may control an optical waves generating device 90 within an applicator 91 (dotted line). The magnetic treatment may be controlled by a hardware panel for magnetic treatment 92 which may control a magnetic field generating device 93 within the applicator 91 (dotted line). The applicator may provide combined treatment.

In an alternative embodiment the at least one optical waves generating device may be in the treatment device. The optical waves may be delivered to the applicator and/or to the target biological structure by a waveguide.

FIG. 19*b* illustrates still another exemplary embodiment of the combined treatment device providing magnetic and/or optical treatment by at least one applicator. The combined treatment device 94 (dotted line) may include a connection to an energy source 95 providing energy for the magnetic treatment and/or for the optical treatment. Optical and/or magnetic treatment may be controlled by a hardware panel 96. The hardware panel 96 may control an optical waves generating device 90 and magnetic field generating device 93 and/or a switching device operating the magnetic field generating device within an applicator 97 (dotted line).

In an alternative embodiment the at least one optical waves generating device may be in the treatment device. The optical waves may be delivered to the applicator and/or to the target biological structure by a waveguide.

Figure 20A:
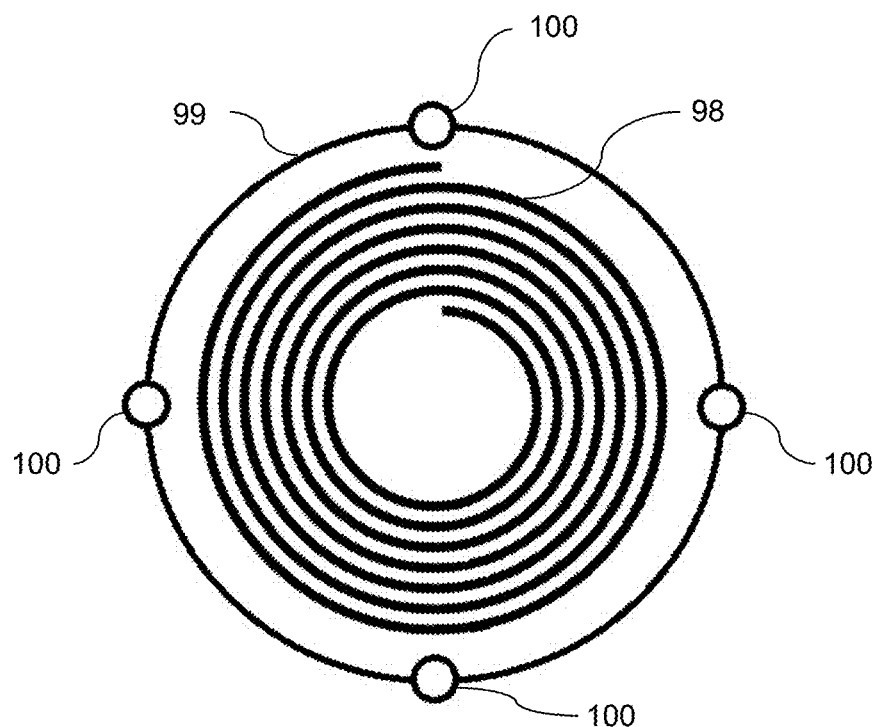
FIGS. 20a and 20b illustrate a combined treatment with optical waves generating device powered by magnetic field generated by magnetic field generating device.
Figure 20B:
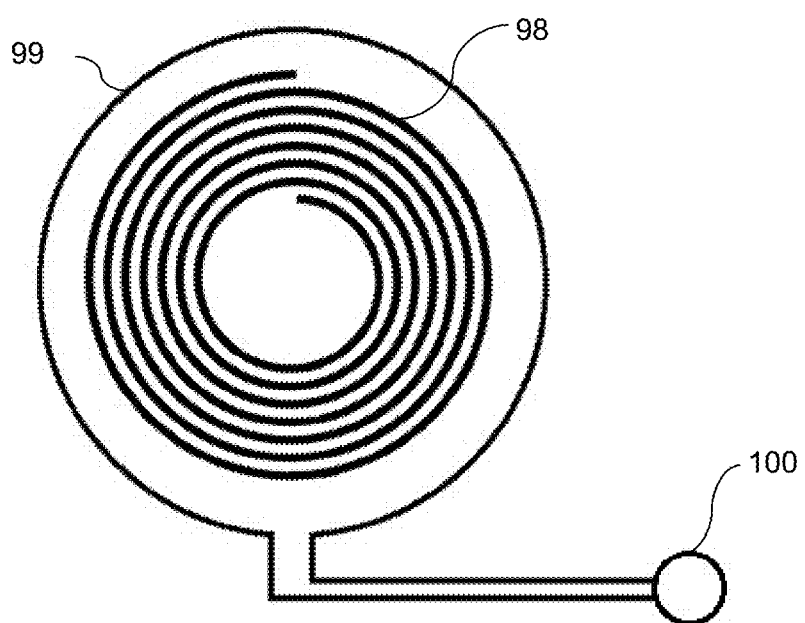

According to still another exemplary embodiment the magnetic field generating device may be used as an energy source for providing energy to at least another part of the treatment device, e.g. an optical waves generating device such as light-emitting diode (LED). FIGS. 20*a* and 20*b* illustrate exemplary embodiments of the magnetic field generating device which may be used as power supply. The magnetic field generating device 98 may be surrounded by a conductor loop 99. The time-varying magnetic field generated by magnetic field generating device 98 may induce eddy currents in the conductor loop 99 within proximity of the magnetic field generating device 98. The induced current in the conductor loop 99 may be used for providing energy to another powered part of the treatment device, particularly in the applicator, or another treatment device, such as at least one optical waves generating device. FIG. 20*a* illustrates an exemplary embodiment of magnetic field generating device 98 surrounded by a conductor loop 99. The conductor loop 99 may be connected to a plurality of optical waves generating devices 100. FIG. 20*b* illustrates another exemplary embodiment of the magnetic field generating device 98 surrounded by the conductor loop 99. The conductor loop 99 may provide the energy to the optical waves generating device 100. The optical waves generating device may be distanced from the conductor loop and may be external to the applicator including the magnetic field generating device 98 and the conductor loop 99.

Alternatively the combined method using the magnetic field for and any of auxiliary treatment methods may be applied to the patient by one applicator, e.g. the magnetic field generating device and different energy source (cooling, mechanical, optical and/or RF waves) may be in one applicator. The magnetic field may be generated by a treatment device separate from another treatment device which provides the auxiliary treatment method, e.g. cooling, optical waves, RF waves or mechanical waves. The first applicator may include the magnetic field generating device and second applicator including the auxiliary treatment may be attached to the first applicator or vice versa. Alternatively the first applicator including the magnetic field generating device and the second applicator including the auxiliary treatment may be attached to the common mechanical holder such as platform.

Biocompatibility issues or hot spot generation may be overcome by transmitting electromagnetic energy into the target biological structure without physical contact with the patient. Contactless application of magnetic and/or optical treatment may provide sufficient passive cooling of the biological structure by circulating air.

In some indications, it may be advantageous to treat deeper adipose tissue by magnetic field simultaneously with the treatment of more superficial layers of the skin by optical waves.

An air gap or bolus with high air permeability may be placed between the skin and the applicator. The bolus may be preferably transparent to the optical waves. This arrangement may use the human thermoregulatory system for cooling and may avoid the need of artificial cooling of the skin. Optionally, the skin may be cooled via a stream of chilled or ambient temperature air. The human thermoregulatory system may enable perspiration and other body fluids to evaporate and may cool the surrounding skin. Sweat accumulation and/or hot spot creation may be avoided. Use of cooling fluids or gels may not be necessary but may be optionally used. Cost of the treatment may be reduced and patient comfort may be improved. The applicator may be in direct or indirect contact with patient's skin. A bolus may be used for providing indirect contact of the applicator with the target biological structure. A bolus may be filled with a material, preferably a fluid, influencing the propagation of the electromagnetic waves and/or homogenizing the temperature distribution of the patient's skin. Alternatively the bolus may deliver the electromagnetic waves to the target biological structure, e.g. a waveguide.

Cooling may be provided by positioning an air moving device proximate to the skin. The air moving device may be attached to or implemented into the applicator. Air moving device may be any kind of fan, ventilator or blower. The blower may include an air tube connected to air source for moving air through the air tube to the patient's skin. The air source may alternatively be cooled to provide cooled air. Alternatively, air suction may be also used as an active cooling method.

Alternatively the treatment may be provided by moving at least one applicator. The movement of the applicator may be manual or automatic. The automatic movement may be random or the movement may follow a predetermined pattern, e.g. an array, a matrix or predefined trajectory designed for the selected treated part of the body. The predefined movement may be adjusted following the patient's needs. The movement of the applicator may be provided by an arm, which may be preferably articulated.

Constant movement of the applicator over a larger area may not be needed. The applicator may remain in a stationary position relative to the patient for several seconds or longer, e.g. for at least 10, 30, 60, 120 or 240 seconds, or longer. The at least one applicator may be of such dimension which may allow to the treated biological structure to be within physiological conditions, e.g. the biological structure may not be overheated over critical temperature causing irreversible changes in the biological structure.

One or more applicators may move in the vicinity of the patient's body. The movement may be provided in various speed and/or acceleration. The applicator may be moved in at least one direction, e.g. longitudinal, vertical, transversal or different axis and/or by rotational movement around any direction. Plurality of applicators may move in synchronized, randomized and/or independent manner. At least one applicator of the plurality of applicator may be static.

The homogeneity of treatment may be provided by the movement of the applicator. In one exemplary embodiment the applicator may move over and/or in different angle to the patient by rotational movement. In another exemplary embodiment the applicator may move in the vicinity of patient's skin. In still another exemplary embodiment the applicator may move to focus the treatment.

The applicator may include at least one sensor for detecting the temperature of the skin. The sensor may be preferably contactless. Alternatively the sensor may measure the temperature in contact manner. Alternatively, the skin impedance may be determined as well.

The sensor may be connected with at least hardware panel for controlling the optical treatment to adjust the power flux density applied to the biological structure to maintain the temperature of the target biological structure within treatment range. The temperature sensor also prevents the patient from any thermic damage.

Figure 21:
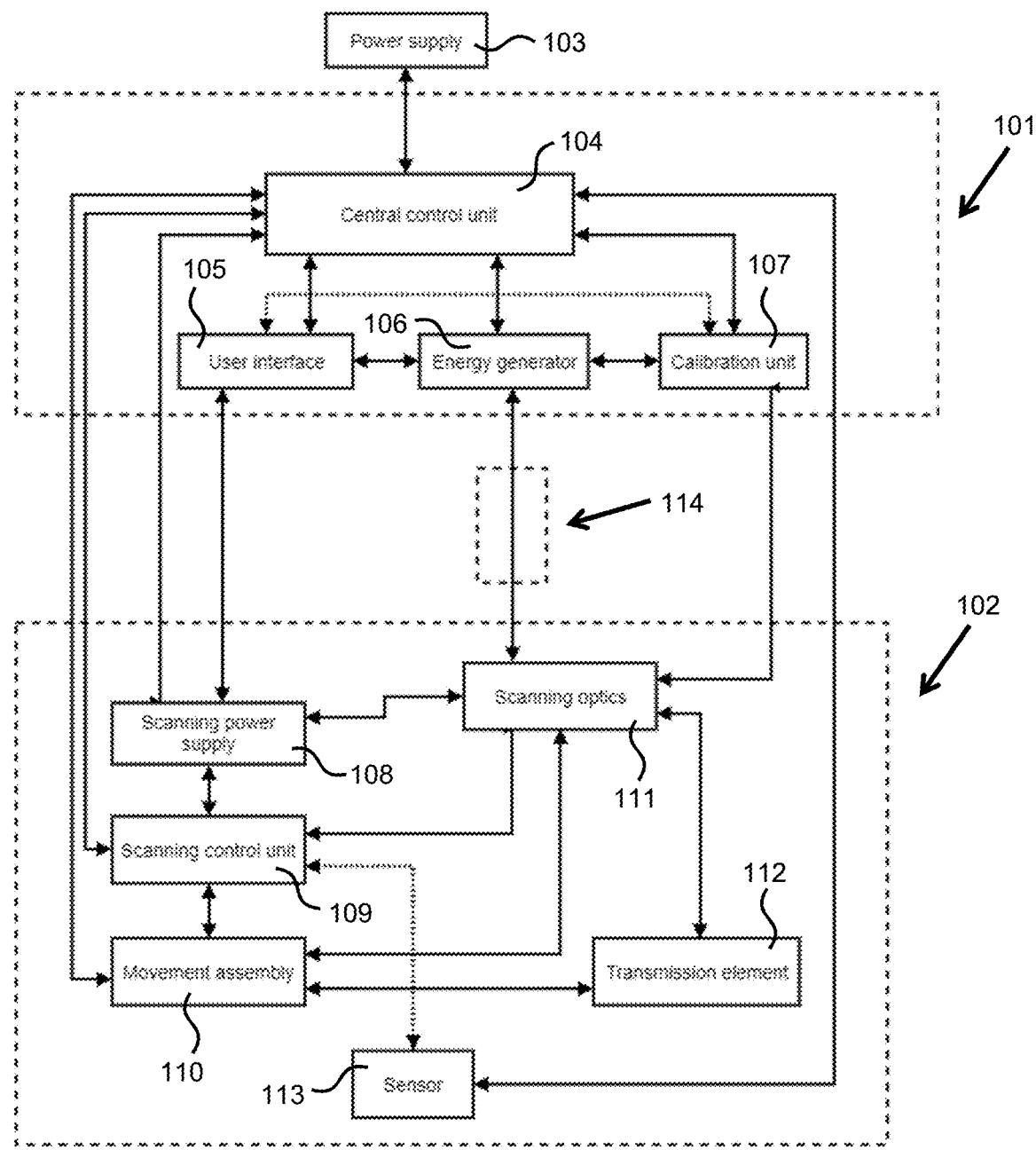
FIG. 21 illustrates a diagram of an exemplary device.

Referring now to FIG. 21, in one embodiment the device includes base 101, handheld applicator 114 and/or a scanning unit 102. Handheld applicator 114 may be used for delivery of the optical waves from the base 101 to the scanning device 102. Base 101 may include central control unit 104, user interface 105, optical waves generating device 106 and/or calibration unit 107.

The central control unit 104 may change the treatment parameters and/or control other parts of the device coupled to it. The method of operation may include the central control unit 104 communicating with user interface 105, optical waves generating device 106, power supply 102 and/or calibration unit 107. The central control unit 104 may also communicate with a scanning power supply 108, scanning optics 111, scanning control unit 109, movement assembly 110 and/or transmission element 112 located in the scanning unit 102. The scanning unit 102 may further include a magnetic field generating device. The magnetic field generating device may communicate with the base 101.

Optical waves generating device 106 may comprise for example, a light emitting diode, a laser emitting diode, a flashlamp, a tungsten lamp, an incandescent lamp, a mercury arc or any other light or optical waves generating device known in the art. Optical waves generating device 106 may generate coherent, incoherent, depolarized and/or polarized optical waves. Coherent monochromatic optical waves may include any type of laser, for example, a chemical laser, a dye laser, a free-electron laser, a gas dynamic laser, a gas laser (for example an argon laser or carbon dioxide laser), an ion laser, a metal-vapor laser (for example a gold vapor laser and/or a copper vapor laser), a quantum well laser, a diode laser (for example comprising GaAs, AlGaSbAs, InGaAsP/InPm InGaAs) and/or a solid state laser (for example a ruby laser, a Nd:YAG laser, a NdCr:YAG laser, an Er:YAG laser, a Nd:YLF laser, a Nd:YVO4 laser, a Nd:YCOB laser, a Nd:Glass laser, a Ti:sapphire laser, a Tm:YAG laser, a Ho:YAG laser or an Er,Cr:YSGG laser). Methods of operation may include optical waves generating device 106 communicating with user interface 105, calibration unit 107 and/or central control unit 104. Optical waves generating device 106 may also communicate with scanning optics 111, typically by providing the generated optical waves (for example light).

In an alternative embodiment the scanning unit may enable detachable communication with handheld applicator applying magnetic field.

The magnetic field generating device and the optical waves generating device may move simultaneously. The simultaneous operation of the magnetic field generating device and the optical waves generating device may generate a common energy spot, i.e. an optical spot and a magnetic spot.

User interface 105 may include an LCD panel or other suitable electronic display. User interface 105 may be located on the base 101, handheld applicator 114 and/or scanning unit 102. User interface 105 may communicate with optical waves generating device 106, central control unit 104 and/or calibration unit 107. User interface 105 may also communicate with scanning optics 111 and scanning power supply 108 located in the scanning unit 102.

Calibration unit 107 may be controlled by central control unit 104. Calibration unit 107 may check stability of the output and/or wavelength of the optical waves generating device 106. In case of instability, calibration unit 107 may provide one or more human perceptible signals to the operator. The calibration unit 107 may also provide information to the central control unit 106 which may adjust or correct one or more parameters of the optical waves generating device 106. Calibration unit 107 may check input or output parameters of the optical waves in the scanning optics 111, located in the scanning unit 102. Methods of operation may include the calibration unit 107 communicating with user interface 105 and/or central calibration unit 104.

Calibration unit 107, optical waves generating device 106 and/or user interface 105 may be positioned in or on base 101, handheld applicator 114 or scanning unit 102.

Embodiments of devices of the present invention may include one or more scanning units 102 which may include scanning power supply 108, scanning control unit 109, movement assembly 110, scanning optics 111, sensor 113 and/or transmission element 112. In some embodiment, scanning unit 102 may provide movement of the optical spot by changing one or more characteristics of the optical beam, including but not limited to the direction or intensity of optical beam. A method of treatment may include control of the scanning unit 102 through central control unit 104 by the user interface 105. The scanning unit 102 may in some embodiments be positioned on an adjustable arm. The scanning unit may be tilted to any angle with respect to the tissue. During some embodiments of treatments using the system of the present invention, the scanning unit may remain in a set position and the optical spot may be moved by the optics inside the scanning unit. In some embodiments, the scanning unit may move continuously or discontinuously over the body and provide treatment by one or more treatment patterns.

The scanning power supply 108 may provide electrical power to components of the present invention, including but not limited to scanning optics 111, scanning control unit 109, movement assembly 110 and/or transmission element 112. The scanning power supply 108 may be coupled to power supply 103. Alternatively, electrical power may be supplied from the power supply 103 directly to some or all mentioned parts by the scanning power supply 108.

The scanning optics 111 may include one or more collimators, optical waves deflecting elements (e.g. deflecting mirrors), focusing/defocusing elements (e.g. lenses) and/or filters to eliminate certain wavelengths of the optical waves. The scanning optics 111 may be controlled according to operator's needs through user interface 105. The scanning optics 111 may be controlled by central control unit 104 and/or scanning control unit 109. Both central control unit 104 and scanning control unit 109 may control one or more parameters of the scanning optics, particularly of one or more deflecting elements. Parameters controlled may comprise the speed of movement of one deflecting element, which may be in the range of 0.01 mm/s to 500 mm/s, more preferably in the range of 0.05 mm/s to 200 mm/s, most preferably in the range of 0.1 mm/s to 150 mm/s.

Scanning control unit 109 may control one or more treatment parameters. The scanning control unit 109 may communicate with central control unit 104, scanning power supply 108, movement assembly 110 and/or scanning optics 111. The scanning control unit 109 may be controlled through central control unit 104 according to the operator's needs selected on the user interface 105, or the scanning unit 102 may include another user interface. In one embodiment, one or more functions of the scanning control unit 109 may be assumed and/or overridden by central control unit 104.

Movement assembly 110 may cause movement of one or more optical spots on treated tissue. The movement assembly 110 may communicate with scanning optics 111 and cause movement of one or more optical waves deflecting elements, which may be parts of the scanning optics 111. The movement assembly 110 may be controlled by central control unit 104 and/or scanning control unit 109. The movement assembly 110 may also communicate with transmission element 112. The movement assembly 110 may comprise one or more motors and/or actuators. The movement assembly 110 may provide angular and/or linear movement to the optical waves deflecting elements of the scanning optics 111. In some embodiment, the movement assembly 110 may provide movement to the transmission element 112.

The optical waves may leave the scanning unit 102 through the transmission element 112. Transmission element 112 may be one or more elements made from translucent material e.g. from glass or crystal with specific optical properties, liquid solution including specific active substance modifying optic parameters and/or soft tissue reaction to the delivered optical waves such as diamond, sapphire or transparent plastic. Transmission element may be connected to the movement assembly 110, which may control focusing, defocusing, vertical or curvilinear movement or tilting of the transmission element 112. Vertical movement of the transmission element 112 may be used for change of optical spot size. Horizontal movement of the transmission element 112 provided by movement assembly 110 may be used for change of optical beam delivered to tissue. When the transmission element includes more elements made from translucent material, horizontal movement may be represented by movement of separate element into the pathway to provide different characteristic to the optical waves provided to tissue (e.g. focus, power output). Alternatively a wave guide may be used, e.g. a light guide. Disclosed configuration may be used for application of more than one optical beam to the tissue. Another configuration may include scanning unit including more than one transmission elements 112 covered by coverings controlled by movement assembly 110.

The scanning unit 102 and/or handheld applicator 114 may include one or more sensors 113, e.g. ultrasound sensor, gyroscope, Hall sensor, thermographic camera and/or IR temperature sensor.

Figure 22A:
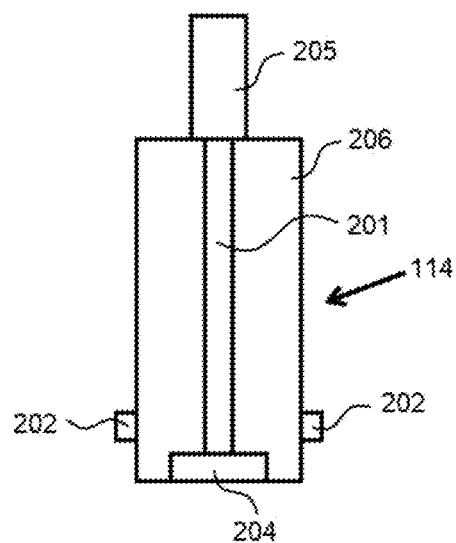
FIGS. 22a and 22b illustrate exemplary handheld applicators.

FIG. 22a shows handheld applicator 114 containing body 206, optical waveguide 201, sensor 202 and/or translucent element 204. Flexible optical waveguide 205 may connect the handheld applicator 114 with the case 101. Optical waveguide 201 may be encased by the body 206 and may provide optical path where the optical path leaves the handheld applicator through the translucent element 204. Translucent element 204 may be similar to transmission element 112 of the scanning unit 102.

Figure 22B:
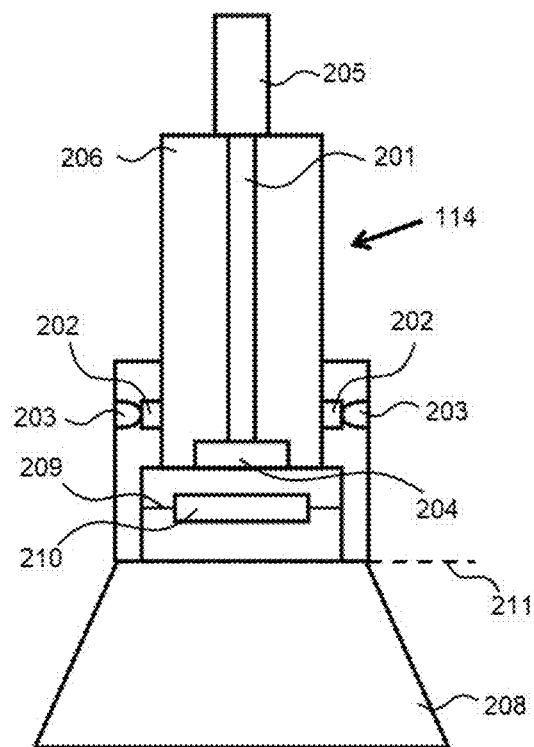

FIG. 22b shows handheld applicator 114 coupled to zooming assembly including lens 210, focusing mechanism 209, spacer 208 and emitters 203. The handheld applicator 114 may provide change of optical spot size according to movement of the lens 210. Lens 210 may be moved by focusing mechanism 209, which may be screwing mechanism. The zooming assembly may include spacer 208, which may have length (i.e. from the tissue to the lowest lens position marked as 211) in range of 0.05 cm to 50 cm, more preferably in the range of 0.1 cm to 35 cm, most preferably in the range of 0.15 to 10 cm.

The handheld applicator may include sensors 202 gathering information from surroundings and/or emitters 203. Emitters 203 (e.g. magnet), located on scanning unit 102, may provide information to sensor 202 (e.g. Hall sensor). Based on the emitted and recognized information, the central control unit may identify particular types of handheld applicator of scanning unit. The recognition may by alternatively provided by RFID, data communication and other known methods. The central control unit may enable treatment parameters according to recognized handheld applicator and scanning unit. Also, the central control unit 104 may limit treatment parameters according to recognized zooming assembly and/or scanning unit 102. Sensors 202 together with emitter 203 may also ensure correct attachment of the handheld applicator 114 with scanning unit 102 and/or zooming assembly. Method of operation may therefore include any human perceptible signal and/or cease of treatment (represented e.g. by shutting of the optical waves generating device) when the attachment is not correct.

Figure 23A:
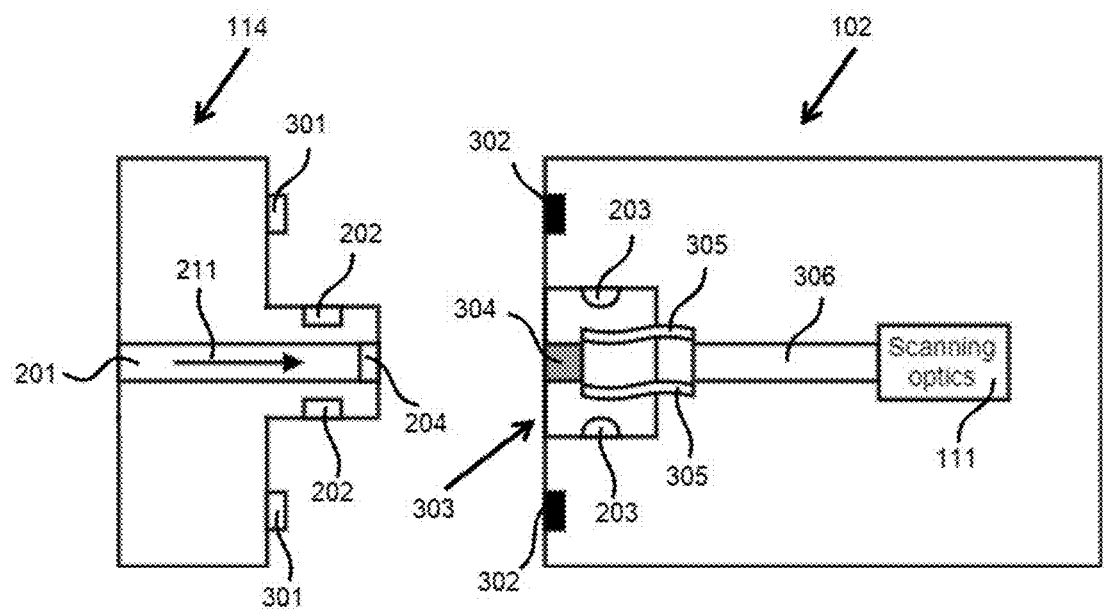
FIG. 23a illustrates a handheld applicator disconnected from a scanning unit.

Handheld applicator 114 may be connected to the scanning unit 102 via attaching mechanism. FIG. 23*a* shows separated handheld applicator 114 from scanning unit 102. Handheld applicator 114 includes optical waveguide 201 guiding the optical waves (represented by arrow 212) encased in the handheld applicator's body 202. Furthermore it contains at least one pin 301. In shown exemplary embodiment, the handheld applicator includes two pins 301. Shown part of the scanning unit 102 includes recesses 302 ready for insertion of pins 301, connector 303, sealing element 304, at least one movement elements 305 (e.g. spring), scanning optical waveguide 306 and scanning optics 111. Movement element 305 (e.g. spring) may be placed in dust-proof cylinder.

Figure 23B:
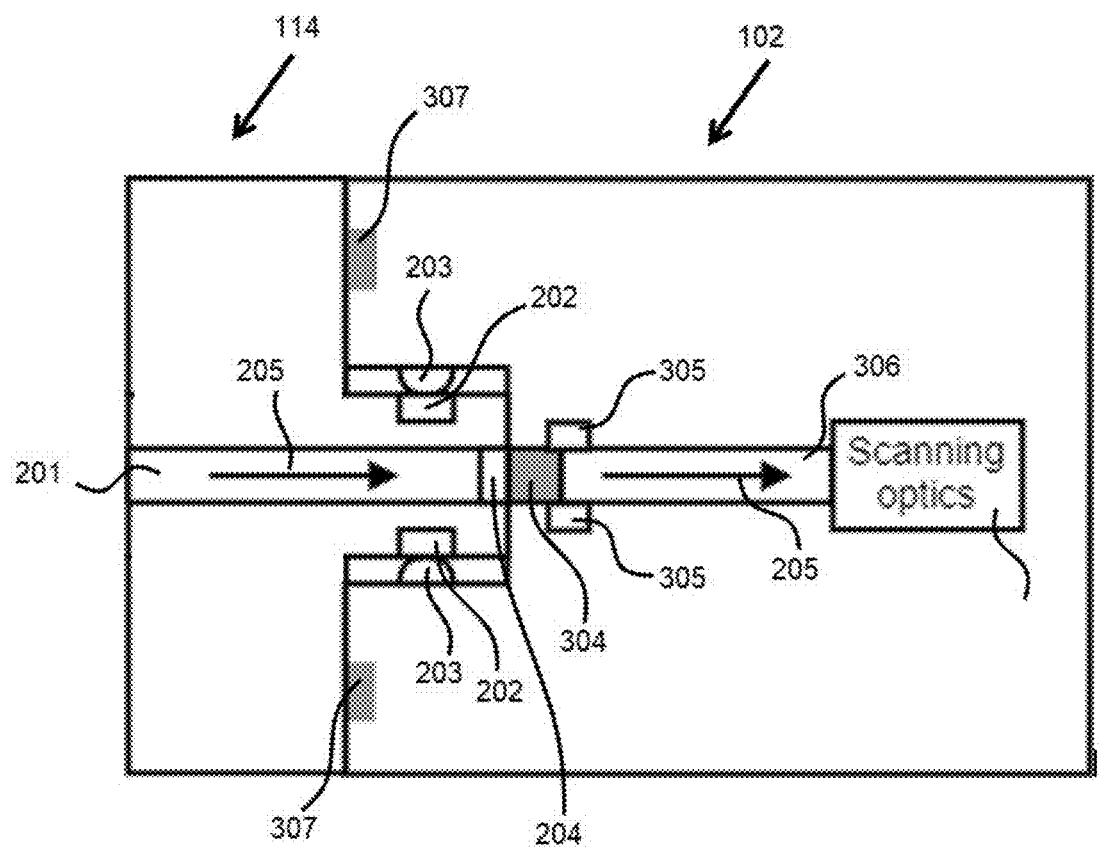
FIG. 23b illustrates a handheld applicator connected to a scanning unit.

FIG. 23*b* shows connection of the handheld applicator 114 to the scanning unit 102 by connector 303. The sealing element 304 may be moved inside the scanning unit 102 adjacent and/or to direct contact with scanning optical waveguide 306. As a result, the sealing element 304 is the part of the newly created optical wave path including optical waveguide 201, translucent element 204, sealing element 304 and scanning optical waveguide 306. The optical waves 205 may be transmitted through the newly created wave path of the scanning optics. The movement of the sealing element is provided by moving element 305 (shown as compressed springs). Alternatively, the movement elements 305 may move the sealing element 304 aside from the optical waveguide.

The handheld applicator is secured in the inserted position by the insertion of the pins 301 to the recesses 302 creating locked pins 307. In exemplary embodiment, handheld applicator 114 may be rotated during the insertion into the scanning unit 102 until the pins 301 meet the recesses 302. During the release, rotating of the handheld applicator on the opposing side may loose the locked pins 307 and the movement elements 305 may provide assisted release of the handheld applicator 114 from the scanning unit 102. Alternatively the handheld applicator 114 may be secured to scanning unit 102 by mechanism using magnetic forces, electromagnet, friction, latching or other know ways.

The sealing element 304 may be e.g. glass, diamond, sapphire or plastic tightly positioned in the connector 303 in the dust-proof cylinder. It may provide dust-proof barrier to the scanning unit 102. Because it may not be removed during the connection between the handheld applicator 114 and scanning unit 102, it may prevent transfer of any contamination and/or dust into the scanning unit 102.

The device and method may provide correct distance control. Correct distance control may ensure the predetermined distance between the treated tissue and scanning unit 102 and/or handheld applicator 114. In an exemplary embodiment the distance may be measured by sound reflection e.g. by ultrasound transmitter and detector placed on and scanning unit 102 and/or handheld applicator 114. Measured distance may be provided to the central control unit 104 which may change one or more treatment parameters according to measured distance. Ultrasound detector may also measure temperature of the treated tissue and the central control unit 104 may change one or more treatment parameters according to the measured temperature.

Temperature of the treated tissue may be measured by thermographic camera and/or IR temperature sensor. Measured temperature may be communicated to the central control unit 104, which may then change one or more treatment parameters according to measured temperature of the treated tissue. Sensor measuring temperature may measure temperature as difference between the beginning of the treatment and the current time of the treatment. The sensor may also cooperate with calibration unit 107 and provide values of real temperature of the treated tissue.

The magnetic treatment and treatment by optical waves may include but is not limited to skin (including epidermis, dermis, hypodermis and/or basement membrane), subcutaneous and/or visceral adipose tissue, blood vessels, gingiva, tooth enamel, dentin, connective tissue, hair follicles, hair papillae, pigmented lesion, muscle, cartilage, tendons, ligaments and/or sebaceous glands. Effects of treatments according to present invention include but are not limited to topical stimulation of the biological tissue, healing, increased metabolism, analgesic reaction, bactericide, temporary increase of blood circulation muscle relaxation, fat elimination, thermal damage (e.g. ablation or coagulation), necrosis, apoptosis, pigment damage, collagen damage, neocollagenesis, elastin damage, neoelastogenesis or damage of connective tissue.

Ablative laser skin resurfacing may cause thermal damage to the epidermis and/or dermis. On the other hand, non-ablative laser skin resurfacing may avoid thermal damage in the epidermis.

In one exemplary application the combined treatment may be used for treatment including but not limited to Achilles tendonitis, ankle distortion, anterior tibial syndrome, arthritis of the hand, arthrosis, bursitits, carpal tunnel syndrome, cervical pain, dorsalgia, epicondylitis, facial nerve paralysis, herpes labialis, hip joint arthrosis, impingement syndrome/frozen shoulder, knee arthrosis, knee distortion, lumbosacral pain, muscle relaxation, nerve repair, onychomycosis, Osgood-Schlatter syndrome, pain relief, painful shoulders, patellar tendinopathy, plantar fasciitis/heel spur, tarsal tunnel syndrome, tendinopathy and/or tendovaginitis. Other applications may include treatment of open wound.

Further applications of the combined treatment may be used for aesthetic and cosmetic methods e.g. reducing the volume and/or number of adipose cells, sagging skin reduction, hyperhidrosis, cellulite treatment, elastin remodeling, elimination of stratum corneum, collagen remodeling, acne treatment, skin rejuvenation, body contouring, skin tightening, wrinkle removal, stretch mark removal, tattoo removal, treatment of rhinitis or circumferential reduction. Embodiments of the present invention may be also used to treat vulvar laxity and/or hemorrhoids. Some embodiments are also capable of at least partial removal of rosacea, dermatitis, eczema, café au lait spots, aphthous stomatitis, halitosis, birthmarks, port-wine stains, pigment stains, skin tumors, scar treatment and/or scar elimination, calcium deposits, herpes simplex, ulcers or other skin diseases classified by the WHO. Some embodiment of the present invention may also be used for general surgery, dentistry, stomatology or body modification e.g. scarification.

Treated parts of a human body may in some embodiments include, but are not limited to, the face, neck, nose, mouth, arm, hand, torso, back, love handle, abdomen, limb, leg, head, buttock, foot and/or thigh.

The commonly targeted skin chromophores are hemoglobin, melanin, carbon or tattoo ink. Alternatively water may absorb the optical waves. Each chromophore has unique absorption spectrum. The wavelength of the optical wave should match one of the absorption peaks of the targeted chromophore. The lasers or laser diodes work usually in pulse regime in these applications. The optical energy absorbed by the chromophore is converted to thermal energy thereby destroying the targeted cells. Selection of the best adapted wavelength, power and pulse duration allows achieving optimal effect on targeted biological structure with minimal effect on surrounding tissue.

The application of optical treatment may be improved by application of exogenous chromophores to the target biological structure. The exogenous chromophores may be applied in form of topical lotion, or may be delivered to the target biological structure by micro-invasive or invasive way such as injected.

According to the parameters of the optical waves used, different layers of the skin and different biological structures may be selectively treated. Various wavelengths, powers, pulse durations and repetition rates of electromagnetic radiation are applicable to provide the advantage of vast variability of penetration and absorption parameters. The operator may also adjust the optimum treatment time for each wavelength and the time sequences of treatments by different wavelengths, while some of them may overlap in time. In this way, a tailor-made solution for each patient and each indication is available. The treatment may be highly selective to reduce or avoid damage of the surrounding tissues.

Combinations of a plurality of optical waves generating devices allow performing the treatment of plurality of target biological structures at the same time and/or treating the same target tissue simultaneously by different means, which optimizes the doses of radiation applied. This diversification may also eliminate the risk of overheating, as the optical treatment with parameters leading to no or negligible thermic effect may be used. As a result, the risk of heat damage may be considerably reduced.

If the patient has more imperfections to be treated situated in the same body areas, it is also possible to treat them simultaneously by different types of electromagnetic waves. Each of the electromagnetic waves may be adjusted to optimum parameters for the target biological structure imperfection treatment. Thus the time of patient and of the operator is reduced, reducing the treatment cost.

The optical waves thermal effect may lead to temperature increase in the dermal and the sub dermal tissues also affects the triple-helix structure of collagen fibers contained in such tissues. This may result in remodeling and rejuvenation of collagen, increase of skin density and dermal thickening based on neocollagenesis. Skin tightening may also be achieved. In one aspect, the present methods selectively treat deep human tissue containing low volume of water, such as adipose tissue. Optical energy is provided to the skin by optical waves generating device. Remodeling and reducing the volume and/or number of adipocytes or skin tightening in the targeted areas may change the overall appearance of the body. Therefore it may be used for body contouring, body shaping and cellulite treatment.

Optical energy may be provided to the skin by at least one optical waves generating device in pulse or continuous mode. Optical energy is provided through the skin to the underlying dermal and/or subdermal tissue, without contacting the skin. The radiant energy may be converted inside the target tissue to heat. The radiant energy enables treating of the adipose tissue and/or collagen tissue, accelerating apoptosis and/or cell lysis (e.g. adipose cell), based on amount of energy transmitted to target biological structure. At the same time the triple helix structure of collagen fibers may result in remodeling and/or rejuvenation of collagen, increase of skin density and dermal thickening based on neocollagenesis. In an alternative embodiment the radiant energy enables treating of target tissue resulting e.g. in neocollagenesis without adipose tissue reduction. Target tissue may be remodeled and/or reduced and body contouring and/or skin tightening effect may occur.

Cooling may also be used to modify and to optimally adjust the depth of optical radiation penetration. Light penetration may be enhanced if cooling is used before phototherapy. The effects of heating in terms of light penetration are the opposite.

In one aspect of the invention, cells may produce heat shock proteins in response to rapid changes of thermic conditions by applied alternation of cooling and treating by optical waves. It has been shown that heat shock proteins stimulate reparation processes in the cells. The principles of cryolipolysis are also involved because adipocytes are more susceptible to cooling than other skin cells. By alternating the steps of cooling and treating, the apoptosis and/or cell lysis (e.g. of adipose cells) may be considerably improved.

Optical treatment may treat the same or different skin layers as the magnetic treatment. As mentioned above, optical treatment may also be used for multiple rejuvenation and appearance enhancing applications. Another important indication is drug-free and addiction-free pain relief in many conditions.

Non-limiting examples of optical therapies that may be preferably used in combination with the treatment by magnetic field according to the present invention are: low level light therapy (LLLT), photodynamic therapy (PDT), high power laser therapy (HPLT) or intense pulsed light (IPL). However, the scope of the invention is not limited only to these particular optical irradiation methods. Other electromagnetic waves may be used, e.g. a radiofrequency treatment.

Low-level light therapy may be one of the methods of non-invasive rejuvenation with no or a very small thermal effect. LLLT may be effective throughout the visible, infrared and near ultraviolet spectrum ranges. The term low level may refer the fact that the levels of energy or power densities may be low compared to other forms of light treatment such as by lasers, which may be applicable for cutting, thermal coagulation or thermal damage, such as ablation. Treatment energies in LLLT may be limited to 0.1-20 or a few $J/cm^2$ and/or by a power of 1 mW to 500 mW per optical waves generating device. The depth of penetration of the low level light radiation may depend on parameters of the optical waves generating device such as wavelength, operating mode, which may be pulse or continuous, the power output, the probe design and the treatment technique. The depth of penetration where the light still may have therapeutic effects should match the depth of the desired zone to be treated. The penetration depth may be lower than in HPTL, up to several tens of mm approximately. Due to the low levels of absorbed energy, the treated and surrounding biological structures may not be heated and may not be damaged. Although many wavelengths may be used, it may be advantageous to use at least one beam in the visible spectrum so that the area of application on the patient's body may be easily determined by the operator.

LLLT may use either coherent optical waves generating devices such as lasers or laser diodes or non-coherent light sources including incandescent lamps, gas filled lamps, filtered lamps optimized for a particular wavelength, light-emitting diodes, etc. A combination of any types of optical waves generating devices may be also used, as well as a plurality of optical waves generating devices of the same type.

The photons emitted by the low level optical waves generating devices used in LLLT therapy may be absorbed by endogenous mitochondrial chromophores in skin. Consequently, many processes may be activated, e.g. electron transport, increased adenosine triphosphate (ATP) production, enhanced blood micro-circulation, collagen production increase, dermal matrix remodeling etc. LLLT may thus successfully treat a multitude of conditions that may require stimulation of healing, acute/chronic pain relief or restoration of function. It has been proved that LLLT may have beneficial effects on wrinkles, scars including acne scars, stimulating the scalp in hair treatment, healing of burns, skin tightening, anti-oedematous effects, regeneration after sport etc. Inflammatory skin diseases such as psoriasis or acne may also be treated by the proposed treatment. In pigmentation disorders such as vitiligo, LLLT may increase pigmentation by stimulating melanocyte proliferation.

LLLT may influence also reduction of number and/or volume of adipose cells. It is believed that the incident optical waves may produce transient pores in adipose cells, allowing lipids to leak out into the interstitial space of adipose tissue. If the parameters are appropriate, the pores may close upon cessation of the energy application and the cell membrane may return to contiguity. The adipose cells may not be destroyed, but temporary opening within the cell's membrane induced by the optical waves may provide a pathway for lipid to exit the cell and in the end also the patient's body. It may lead to the reduction of number and/or volume of adipose cells. This adipose cell number and/or volume reduction may restore proper adipose cells function thereby acting as an anti-diabetes mechanism.

It may be advantageous to combine LLLT and magnetic treatment for safe and efficient target biological structure treatment.

While in LLLT the light may be absorbed by endogenous cellular chromophores, PDT may be based on introduction of exogenous photosensitizers into the cells which may be then irradiated with wavelengths of visible or near infra-red light. Photosensitizer drugs may become activated by one or several types of optical waves. The optimal type of optical waves may depend on the target biological structure and the absorption peak of the particular chromophore drug used. PDT optical waves generating devices may include laser, intense pulsed light, light-emitting diodes or many visible lights including natural sunlight, etc.

Unlike LLLT HPLT may cause thermic effects on the skin. HPLT lasers having an output of 500 mW or greater may be used for this treatment, with energy densities greater than 10 $J/cm^2$. High power may allow extremely high penetration of the optical waves, in order of ten centimeters or even more, ensuring that the right dose actually reaches the target biological structure localized deep in the tissue. Laser may be precisely adjusted due to its monochromacy and coherency. Therefore its propagation and targeted biological structure may be finely pre-defined. Research shows that biological structures treated by HPLT may be irradiated to increase production of adenosine triphosphate (ATP). Similarly to LLLT, the biological responses to increased ATP production may include reduction of inflammation, reducing scars, increased cell metabolism, improved vascular activity, and accelerated healing. It may improve regeneration after sport. Significant improvements of many post-traumatic pathologies or osteoarthritis have been noted, as well as temporary relief of stiffness and muscle spasms. It may be important to note that HPLT also may provide the patients with drug-free and addiction-free acute and/or chronic mediation of pain, by decreasing inflammation and/or swelling and by increasing the release of endorphins and enkephalins. Moreover, if pulse regime is applied, the wavelength-specific photomechanical wave generated in the tissue may stimulate free nerve endings, thus blocking pain pathways in the nervous systems and bringing immediate pain relief.

High power lasers, laser diodes or intense pulse light sources (IPL) may be also used for treating pigmented targets in the skin by selective photothermolysis. Such high power lasers reaching sufficient power density to vaporize illuminated cells may be gas lasers such as CO2 or excimer laser, solid-state lasers such as rubin, Nd:YAG or Er:YAG laser, semiconductor lasers, dye lasers such as Rhodamin 6G laser etc.

The indications may include e.g. vascular lesions, varicose veins, acne, pigmented lesions and mole marks or tattoos.

Similar principles may also be used for removal of excessive body hair. Light pulses may target the hair follicle causing the hair to fall out and minimizing further growth. Alternatively, light may be delivered to target biological structure continuously.

IPL may be used also for some other skin treatments with therapeutic or rejuvenating effects, sharing some similarities with high power laser treatment. In both cases, optical waves may be used to destroy the target by treating. But unlike lasers using a single wavelength of light which may typically match only one chromophore, and only one condition, IPL may use a broad spectrum of wavelengths. When used with filters, it may be adapted to treat various conditions. This may be achieved when the IPL operator selects the appropriate filter that may match a specific chromophore. Such filter may be represented by an optical material filtering e.g. 480 nm, 530 nm, 560 nm, 640 nm or 690 nm.

The optical energy flux density of the IPL treatment may be in the range of 1 and 50 $J/cm^2$, preferably in the range of 2 to 40 $J/cm^2$, more preferably at least 5 $J/cm^2$, or up to 100 $J/cm^2$. The optical waves may be applied continually or in pulses. Pulse width may be time duration that the target is exposed to the optical waves. Pulse width may be measured in miliseconds. Pulse width may be shorter than thermal relaxation time of the target, i.e. the pulse width may be long enough to allow heating of the target but also short enough that the target may be able to cool so that there may be no heat buildup in surrounding skin and tissue. The pulse width may be in the range of 1 to 300 ms, preferably in the range of 5 to 50 ms, most preferably up to 30 ms.

According to one application a combined treatment by optical waves and magnetic field may be used for treatment of pelvic floor area disorders, e.g. gynaecologic and/or urologic issues such as incontinence, or menorrhagia. One exemplary application may be inserting the optical wave generating device into the body cavity, e.g. a vagina. The optical treatment may selectively raise a temperature in the vagina to provide tightening effect. A suitable probe may be used for inserting the optical waves generating device. The target biological structure may be tightened due to increased temperature and/or improved collagenesis. Alternatively the optical wave generating device may be external to the body cavity and the optical waves may be delivered to target tissue by optical delivery element.

An exemplary application of combined treatment by optical waves and magnetic treatment may be application to enhancing appearance of genitalia, e.g. external female genitalia such as labia minora, labia majora and/or clitoris. Furthermore collagenesis may be improved in vagina hence it may be smoother and/or firmer. Therefore the combined treatment may enhance physical pleasure during coitus.

Optimal wavelength of the optical waves may be in the range of 400 to 600 nm, particularly around 500 nm. Energy density may be up to 25 $J/cm^2$, more preferably up to 10 $J/cm^2$, most preferably in the range of 1 to 8 $J/cm^2$. Treatment may be administered in continual or preferably in pulsed mode.

The magnetic treatment may be targeted to the area of pelvic floor to treat pelvic floor muscles. The repetition rate of the magnetic pulses may be in the range of 1 to 150 Hz, preferably up to 100 Hz, more preferably in the range of 5 to 70 Hz, e.g. at least 30 Hz. Alternatively the optical treatment may provide biostimulation effect to promote neocollagenesis. The tightening effect may be also promoted by at least muscle contraction. Hence the treatment of incontinence may be provided by different energy types. The collagenesis may be improved by application of magnetic treatment improving local metabolism by improved blood flow and/or at least muscle contraction.

According to one application a combined treatment by optical waves and magnetic field may be used for treating a pain. The pain relieving effect may be combined and significantly improved due to different applied energies and different approaches of relieving the pain. The pain relief is drug-free and may last up to several hours after the treatment. The pain relieving may be applied for treatment of chronic and/or acute pain. Alternatively, the pain relieving effect caused by magnetic and/or optical treatment may be used for improving acceptability of optical treatment provided by high power density optical radiation, e.g. high power laser or IPL. The repetition rate of magnetic pulses is at least 100 Hz, more preferably at least 140 Hz.

According to one application a combined treatment by optical waves and magnetic field may be used for myorelaxation effect. High efficient relaxation may be caused by combined influence optical and magnetic treatment on the biological structure. The target biological structure may be relaxed by optical treatment, e.g. by increased temperature of the target biological structure, and by magnetic treatment using repetition rate of the magnetic pulses of at least 100 Hz, preferably at least 150 Hz or at least 180 Hz.

According to one application a combined treatment by optical waves and magnetic field may be used for adipose cells reduction. The adipose cells may be heated by the optical treatment above 37.5° C., more preferably above 40° C., most preferably in the range of 40 and 50° C., or up to 60° C. The temperature increase may induce apoptosis and/or necrosis of the adipose cells. The apoptosis of the adipose cells may be preferred effect due to reduced risk of inflammation and/or panniculitis occurrence. The temperature increase may also liquefy the adipose tissue. The magnetic treatment may contribute the optical treatment by inducing the at least muscle contraction which may improve the local blood and/or lymph circulation and/or local metabolism. Hence the death adipose cells may be removed faster from the human body. The apoptosis of the adipose cells may be also contributed by the influence of the magnetic treatment to metabolism of Ca ions as was described before. The optical waves may be in visible or in IR spectrum such as near-IR spectrum, e.g. in the range of 600 to 2000 nm in a plurality of applicable bands e.g. in the range of 635 to 680 nm, particularly 658 nm; or in the range of 780 to 980 nm, particularly 800 nm or 940 nm; or in the range of 1050 to 1100 nm, particularly 1060 nm due to relatively high penetration through the skin. Alternatively the optical waves may be in the range of 1300 to 1450 nm, particularly 1320 and 1440 nm may be applicable. Alternatively wavelength of 2940 nm may also be used.

The optical treatment may last up to 120 minutes, preferably in the range of 1 to 60 minutes, more preferably in the range of 20 to 40 minutes. The treatment time may be dependent on BMI of the patient. The power flux density of the optical treatment may be up to 50 $W/cm^2$, preferably up to 25 $W/cm^2$, more preferably in the range of 1 to 15 $W/cm^2$, most preferably in the range of 2 to 10 $W/cm^2$ such as at least 5 $W/cm^2$. In the preferred application power modulation may be used.

The above mentioned methods may be combined and the improved treatment effect may be induced. The treatment results may be achieved in shorted time period and may be more significant.

According to one application a combined treatment by optical waves and magnetic field may be used for cellulite treatment. Optical waves may penetrate the skin and increase the temperature of adipose cells and thermally damage the adipose cells. Hence the optical treatment may be used for reducing number and/or volume of adipose cells, remodeling treated body parts, or improving the skin appearance. The target biological structure, e.g. adipose cells, may be exposed to increased temperature. The temperature may be in the range of 37.5 to 60° C., more preferably in the range of 40 to 50° C., most preferably in the range of 42 to 47° C., or up 80° C. The damaged adipose cells may be removed by blood and/or lymphatic system to be metabolized. The heat generated in the target biological structure may induce a production of growth factors and/or fibroblasts which may improve collagen neogenesis and/or new vein formation to support the newly generated collagen formations.

The adipose cells may be influenced by apoptosis and/or necrosis. Alternatively the adipose cells may be liquefied. The adipose cells metabolism may be contributed by the at least muscle contraction. Furthermore the application of optical treatment may heat the fibrous septae of the cellulite. The heated septae may be straightened by the at least muscle contraction caused by the magnetic treatment. Further the at least muscle contraction may remove the water from the cellulite tissue to reduce the cellulite. Therefore more significant results may be achieved in shorter time periods. The above mentioned methods may be combined hence the enhanced effect may be induced. Hence the results may be achieved in shorted time period and may be more significant.

Optimal wavelength should include low absorption within the skin, i.e. low absorption of water and/or melanin, and high absorption within the adipose cells. The optical waves may be in visible or in IR spectrum such as near-IR spectrum, e.g. in the range of 600 to 1500 nm in a plurality of applicable bands e.g. in the range of 635 to 680 nm, particularly 658 nm; or in the range of 780 to 980 nm, particularly 800 nm or 940 nm; or in the range of 1050 to 1100 nm, particularly 1060 nm due to relatively high penetration through the skin. Alternatively the optical waves may be in the range of 1300 to 1450 nm, particularly 1320 and 1440 nm may be applicable.

The optical treatment may last up to 120 minutes, preferably in the range of 1 to 60 minutes, more preferably in the range of 20 to 40 minutes. The treatment time may be dependent on BMI of the patient. The power flux density of the optical treatment may be up to 50 W/cm$^2$, preferably up to 25 W/cm$^2$, more preferably in the range of 1 to 15 W/cm$^2$, most preferably in the range of 2 to 10 W/cm$^2$ such as at least 5 W/cm$^2$. In the preferred application power modulation may be used.

Optionally, an active cooling may be included. However, in many cases, auto thermoregulation by sweating may be sufficient. The active cooling may be administered in continual mode or in pulsed mode to maintain the skin temperature within physiologic temperature, i.e. around or below 37° C.

According to one application a combined treatment by optical waves and magnetic field may be used for body shaping and/or improving muscle tonus. According to one application, the muscle may be treated by the optical treatment to increase the temperature of the muscle. Afterwards the heated muscle may be treated by magnetic treatment. The magnetic treatment may achieve more significant results due to increased temperature of the muscle. The muscle may be toned and/or strengthened more effectively. The toned and/or strengthened muscle may induce body shaping effect to enhance visual appearance of the treated body part. Moreover the results may be achieved without hours spent by exercising of the muscle which may achieve unpredictable results within different body parts. The effectiveness of the magnetic treatment may be enhanced by preheating of the muscle by optical treatment. Magnetic treatment may be provided at repetition rate of at least 0.1 Hz, more preferably at least 5 Hz, even more preferably at least 20 Hz, most preferably at least 50 Hz, or up to 700 Hz. The magnetic treatment may be preferably modulated.

The above mentioned methods may be combined and the improved treatment effect may be induced. The treatment results may be achieved in shorted time period and may be more significant.

According to one application a combined treatment by optical waves and magnetic field may be used for focused treating of specific muscle structures, e.g. buttock. The demand for enhancing visual appearance of the buttock has rapidly increased during last few years. The combined treatment may enhance the visual appearance of the buttock by thermal effect caused by optical treatment and/or by muscle exercising effect by focus magnetic treatment. The magnetic treatment may be selectively focus to enhancing the visual appearance of the buttock by shredding and/or toning of the buttock muscles such as gluteus maximus, medius and/or minimus.

Alternatively the combined focused treatment may be used for causing breast lifting effect by preheating effect of the Cooper's ligament and following magnetic treatment with increased effectiveness. The treatment may lift the breasts up.

The above mentioned methods may be combined and the improved treatment effect may be induced. The treatment results may be achieved in shorted time period and may be more significant.

According to one application a combined treatment by optical waves and magnetic field may be used for skin rejuvenation. The optical treatment may be applied to cause micro-damages within the skin to promote the increase production and/or regeneration of collagen fibers. It may induce the enhanced visual appearance of the skin which may look well-toned, smoother and/or firmer. The optical treatment may be contributed by magnetic treatment causing at least muscle contraction which may induce the increase local metabolism and/or blood circulation. Hence the sufficiency of nutrients may be delivered to the target biological structure to promote its regeneration and/or production process.

Optical waves providing biostimulation effect may be of wavelength in the range of about 400 nm to 1200 nm, more preferably in the range from 440 to 1100 nm most preferably in the range from 450 to 1000 nm. Optical waves providing biostimulation effect may be coherent, non-coherent, monochromatic and/or polychromatic.

The above mentioned methods may be combined hence the enhanced effect may be induced. Hence the results may be achieved in shorted time period and may be more significant.

According to one application a combined treatment by optical waves and magnetic field may be used for treating the scars and/or stretchmarks. The optical treatment may enhance the visual appearance of scars and/or stretchmarks by providing improved the growth of collagen and/or elastin fibers to provide the skin younger, firmer and/or smoother appearance. The optical treatment may induce micro-damages to collagen and/or elastin fibers to promote their regeneration and/or production. The optical treatment may be contributed by magnetic treatment causing at least muscle contraction which may induce the increase local metabolism and/or blood circulation. Hence the sufficiency of nutrients may be delivered to the target biological structure to promote its regeneration and/or production process. Furthermore the at least muscle contraction may straighten the newly produced collagen and/or elastin fibers by massaging effect.

The parameters of optical treatment may be similar as used for wrinkle treatment.

The above mentioned methods may be combined and the improved treatment effect may be induced. The treatment results may be achieved in shorted time period and may be more significant.

According to one application a combined treatment by optical waves and magnetic field may be used for treating the wrinkles. The optical treatment may remove the wrinkles by resurfacing of the skin. Different wavelength may promote the growth of collagen and/or elastin fibers to provide the skin younger, firmer and/or smoother appearance. The optical treatment may be contributed by magnetic treatment causing at least muscle contraction which may induce the increase local metabolism and/or blood circulation. Hence the sufficiency of nutrients may be delivered to the target biological structure to promote its regeneration and/or production process.

According to one application a combined treatment by optical waves and magnetic field may be used for lip visual appearance enhancing effect. The optical treatment may improve the growth of collagen and/or elastin fibers to provide younger, fuller, firmer and/or smoother appearance. The optical treatment may be contributed by magnetic treatment causing at least muscle contraction which may induce the increase local metabolism and/or blood circulation. Hence the sufficiency of nutrients may be delivered to the target biological structure to promote its regeneration and/or production process.

The above mentioned methods may be combined and the improved treatment effect may be induced. The treatment results may be achieved in shorted time period and may be more significant.

All the above mentioned methods may be used in various time sequences of optical and/or magnetic treatment. The major time sequences are described below.

Alternatively, the application of optical waves may provide disinfection effect. Such application may include application of UV light, e.g. UV-B and/or UV-C light. The wavelength of the optical waves may be in the range of 200 to 300 nm, most preferably in the range of 250 to 270 nm. The optical radiation may destroy the DNA of microorganisms such as bacteria, or virus. The nucleic acid in DNA may form a covalent bond (such as thymine dimer) preventing unzipping process during reproduction cycle. Hence the replication ability of the microorganism is disabled and the microorganism may die and the infection may be treated. The power density may be up to 300 mW/cm$^2$, preferably up to 200 mW/cm$^2$, or in the range of 1 to 50 mW/cm$^2$, more preferably in the range of 5 to 25 mW/cm$^2$. In one exemplary application the UV light may be in external flow-chamber to provide disinfected air to the treated area.

Similar application of optical waves may be used for cleaning the skin of the patient.

Another application of optical treatment may be treatment of fungal infections of nails and/or skin. Non-limiting examples of these infections may be athlete's foot, jock itch, ringworm or yeast infection. The skin and/or the nail suffering from these infections may change a color, get thicker or it may hurt. The infection may be treated by optical radiation. Additionally, a pain may be relieved by the optical treatment.

The method of treatment may include treatment of one or more treatment areas by one or more treatment patterns. Treatment of the treatment area by one or more treatment areas may be repeated more than one time. Treatment area may be defined as an area where the optical spot is moved during treatment session, together with surroundings of this area. Treatment pattern may be defined as shape of resulting surface trajectory of the optical spot on the treatment area during one treatment cycle. The method of treatment during may include following steps:

Method of treatment may include following steps: choosing of body part to be treated; mapping of the tissue problem by the sensor; proposing and modification of shape and dimensions of one or more treatment area; selection of shape and dimension of one or more treatment patterns; setting of threshold values of treatment parameters; setting of threshold ranges; choosing of treatment mode; optical waves transfer to the tissue; measuring of treatment parameters and/or specifications of the tissue problems (e.g. color, shape and/or depth); response to measurement.

Order of the steps may be changed. One or more steps may be omitted and/or multiplied.

Body part to be treated may be chosen by patient, operator and/or device. Patient and/or operator may choose the body part because of esthetic or medical reason. Device may choose the body part according to information from one or more sensors. For example, the ultrasound sensor may provide information about thickness of adipose tissue and/or camera may provide information about presence of esthetic problems (e.g. cellulite).

Mapping of the tissue problem may be provided by camera and/or ultrasound sensor. In case of camera, tissue problem may be recognized by comparing the colors in the treatment area with the color of reference tissue area. In case of ultrasound sensor, tissue problem may be recognized by comparing the parameters (e.g. amplitude, frequency, period and/or reflection angle) of reflected mechanical wave of treatment area with the parameters of reflected wave of reference tissue area. Reference tissue area may be untreated tissue area chosen by the operator and/or device. Color and/or parameters of reflected mechanical wave may be measured before and/or after the mapping. The color and/or parameters of the reference tissue may be measured during the mapping by the same sensor and/or different sensor.

Shape and dimension of the treatment area may be selected separately. Shapes may be selected from predefined set of shapes or the shape may be created by the operator and/or device. Additionally, shape may be proposed by device according to chosen body part. Shape of treatment pattern may be created according to the picture of the tissue problem captured by camera. After the selection, shape may be further modified by operator and/or patient by dividing the shape into plurality of segments (e.g. smaller surface parts and/or borderlines) and their movement to another shape. The creation of new shape, change of one or more dimensions, division of created shapes and/or movement of segments may be executed using the user interface 106. Dimensions of the treatment area may be in the range of 1×1 cm to 180×180 cm and may have area from 1 cm$^2$ to 32 400 cm$^2$, 15 000 cm$^2$, 10 000 cm$^2$ or 2500 cm$^2$. Dimensions of the treatment pattern may be in the range of 0.01 cm$^2$ to 5000 cm$^2$ or 0.1 cm$^2$ to 2000 cm$^2$ or 1 cm$^2$ to 500 cm$^2$.

Figure 24:
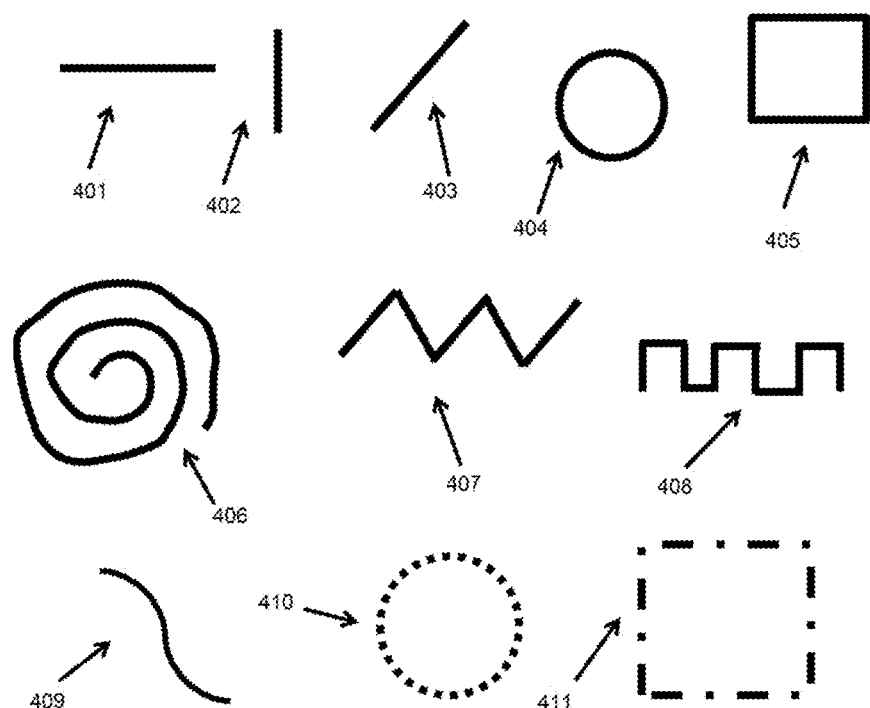
FIG. 24 illustrates examples of treatment patterns.

Examples of treatment patterns on the tissue surface shown on FIG. 24 are linear vertical 401, linear horizontal 402, linear diagonal 403, circular 404, rectangular 405, spiral 406, zigzag 407, tooth-like shape 408 and/or S-shape 409. Treatment pattern may be delivered in defined points and/or intervals, as shown on objects 410 and 411. Alternatively the treatment patterns may be created by optical inside the tissue.

Figure 25A:
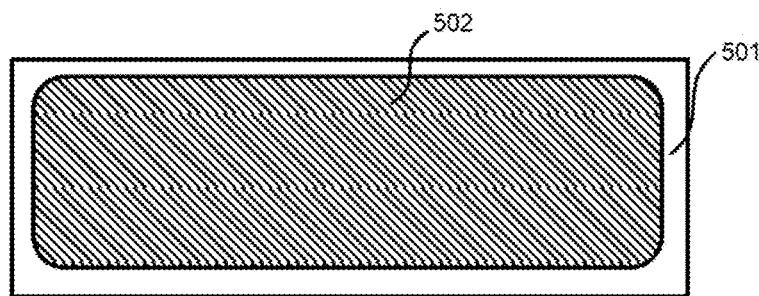
FIGS. 25a and 25b illustrate examples of a treatment area and treatment pattern.
Figure 25B:
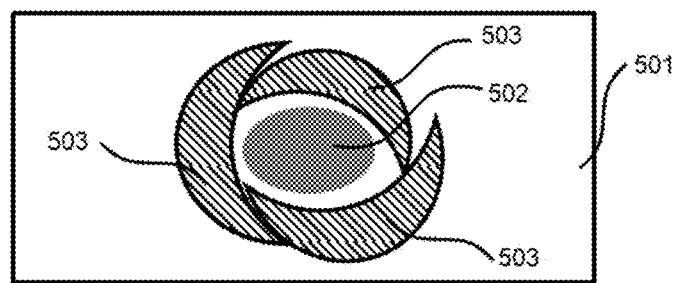

FIG. 25a shows treatment area 501 with treatment pattern 502. Treatment pattern 502 is shown to be large surface pattern, which may be allowed by absence of any substantial unevenness. FIG. 25b shows treatment area 501 with unevenness 502 and three treatment patterns 503a-c contacting each other.

Setting of threshold value may include choosing one or more threshold values of one or more treatment parameters for determining other treatment parameters. Threshold value may be temperature of the treated tissue. Alternatively, the threshold value may be distance between the tissue and scanning unit or handheld applicator, total output of the optical waves to at least part of the treated tissue area, optical flux transferred to at least part of the treatment area, scanning speed of the scanning unit 102 and/or handheld applicator 114. Method may include increasing of one or more threshold values until the patient and/or operator stop the increase. During the increase of the threshold value the central control unit 104 may adapt at least one treatment parameter to increasing threshold value. The threshold value may be set before treatment or it may be changed during treatment according to measured parameters by sensor 113 (e.g. distance and/or temperature of the treated tissue). When the one or more threshold values of treatment parameters are set, other treatment parameters may be adapted by device.

Setting of threshold ranges may include setting of ranges around the threshold value, which may be about 25%, more preferably 20%, even more preferably about 15%, most preferably 10% around the threshold value. Method may include setting of ranges of other treatment parameters, which have no set threshold value. Such range may prevent non-homogeneity of treatment.

Choosing of treatment modes is related to interchangeability of treatment provided by scanning unit 102 and manual treatment provided by handheld applicator 114. Large treatment areas without any unevenness may be treated by using scanning unit 102 while treatment areas with unevenness may be treated by handheld applicator 114. Scanning unit 102 may however be used to treatment of treatment area with unevenness because device may include adjustment of treatment parameters according to other steps of the method. It may be possible to combine use of scanning unit 102 with handheld applicator 114. For example, treatment pattern 502 on FIG. 25*a* may be provided by scanning unit 102, while treatment patterns 503 on FIG. 25*b* may be provided by handheld applicator 114. The operator may use scanning unit for treatment of large areas of the tissue while the handheld applicator may be used for treatment of the areas not affected by the scanning unit. The change of the handheld applicator to more effective scanning unit by connection of the former to the latter provides the operator versatile device for complex treatment. Both modes of treatment may be provided by one device.

Optical waves transfer to the tissue may include irradiation of the tissue by the optical waves. Also, camera may provide information about position of the optical spot on the surface of tissue.

Measuring of treatment parameters and/or specifications of the tissue problem may include measurement provided by one or more sensors 113. Treatment parameter may be measured continually or in distinct time intervals. Also, the measuring may include processing of the measurement, preferably by providing the information from the sensor 113 to central control unit 104. Sensor 113 may measure treatment parameter with set threshold value and/or threshold range. Measurement of the tissue temperature may be done by temperature sensor and measured tissue temperature may be communicated to central control unit 104. Measurement of the specification of the tissue problem may include measurement of its color, shape, depth and/or temperature on the edge of the tissue problem. Specification of tissue problem may be measured by camera and/or ultrasound sensor in similar way as the mapping of the color irregularity.

Response to measurement of treatment parameters may include continuation of treatment, providing human perceptible signal, setting of new threshold value and/or threshold range, cease of treatment, adjustment of one or more set treatment parameters to set threshold in order to be in the range. For example, when the temperature of the treated tissue is out of threshold temperature range, the central control unit 104 may cease the optical waves transfer and/or change one or more treatment parameters (e.g. optical spot size, optical spot shape, duration of the treatment, optical waves output, direction of the movement of the optical spot and/or scanning speed) in order to bring the temperature of the treated tissue back to the set threshold value and/or inside the threshold range.

In another example, the set threshold value may represent the distance of the treated tissue from scanning unit or handheld applicator. Because the presence of unevenness on the treated tissue may bring the scanning unit and/or handheld applicator closer to the treated tissue, the response may include adjust the distance in order to keep the actual distance as close as possible to the set threshold value, provide human perceptible signal, cease the treatment and/or change one or more treatment parameters (e.g. optical waves output and/or optical spot size) in order to compensate for change of distance. Change of one or more treatment parameters may lead to change of threshold value. Change of one or more treatment parameters according to distance of treated tissue from scanning unit or handheld applicator may be advantageous for treatment of less approachable curved parts of the body (e.g. flanks, legs and/or hips).

In still another example two threshold values representing the temperature of the treated tissue during the treatment and distance between the tissue and scanning unit or handheld applicator may be set. When the temperature of treated tissue and the distance are different from the set threshold values (e.g. because of the presence of unevenness or non-homogeneity of optical waves generating device), the response may include cease of operation, human perceptible signal, change of one or more treatment parameters (e.g., optical waves output, optical spot size, scanning speed, direction of the movement of the optical spot, treatment pattern, wavelength of the optical waves, frequency and/or optical flux) in order to bring the measured parameters of the treated tissue closer to the set threshold values and/or into the interval provided by threshold ranges.

Response to measured specification of the tissue problem and may include cease of treatment and or change of more treatment parameters. For example, response may include decreasing of scanning speed, change of treatment pattern and/or repeated movement of the optical spot over the tissue problem when the tissue problem retains the color during treatment. In another example when the optical spot is moved to differently colored part of tissue problem (e.g. tattoo), the wavelength of the applied optical waves may be changed e.g. in order to provide treatment to differently colored pigment and/or ink. In still another example response may include change of output of the power, optical spot size, wavelength of the optical waves and/or distance between tissue and scanning unit when at least part of the tissue problem is located deeper than anticipated during initial mapping of the tissue problem. In still another example response may include change of treatment pattern together with change of wavelength of applied optical waves. In such case, when the color of already treated tissue problem changes during and/or after the treatment, the optical spot may be repeatedly moved over the tissue problem, while the applied optical waves has different wavelength matching the different color of the tissue problem.

Response to changing and/or unchanged shape of the tissue problem may include cease of treatment and/or change of one or more treatment parameters. For example, when the shape of the tissue problems is changed, the treatment parameter and/or optical spot size may be changed in order to match newly shaped tissue problem. Also, the output power of the optical waves and/or scanning speed may be changed.

Method of treatment may further include cease of operation of the device and/or provide human perceptible signal according to the information from ultrasound sensor and/or gyroscope if error occurs. Error may be movement of the patient sensed by ultrasound sensor. The error may be a change of distance between scanning unit and tissue. The event may be change of position of the scanning unit itself sensed by gyroscope. Ultrasound sensor and/or gyroscope may then provide such information to controller. The controller may process the information and cease the operation of device and/or provide human perceptible signal (e.g. sound, change of scanning color).

Other sensor 113 may be the sensor measuring oxygenation of the blood. Oxygenation sensor which may be contact or preferably noncontact and it may be e.g. invasive Clark electrode, RGB camera, spectrophotometer, one or more CCD cameras with specific filters (e.g. 520 nm and/or 660 nm) may provide information about blood flow and healing of the tissue. The oxygenation of the tissue may also be measured by diffuse correlation spectroscopy flow-oximeter. Method may include measurement of oxygenation of the blood in blood vessels in and/or close to the treatment area. Measurement of oxygenation of the blood may be executed in blood vessels in and/or close to the treatment pattern. Oxygenation sensor may provide information to the central control unit 104. The central control unit 104 may include proportional controller which may cease the transfer of optical waves when the blood oxygen level drop below oxygenation limit having value of 98%, more preferably 96.5%, most preferably 95%. Also, the central control unit 104 may include PD and/or PID controller which may adjust one or more treatment parameters. When the blood oxygen level drops below the limit, operation may be ceased, optical waves output may decrease and/or increase, wavelength may be changed and/or optical waves generating device may be changed. Optical waves output may be decreased for decrease of temperature and/or level of tissue damage (e.g. ablation, coagulation). Change of wavelength may include change to wavelength of or close to red light, which may enhance blood oxygenation. Also, the response may include change of one or more other optical treatment parameters.

Figure 26A:
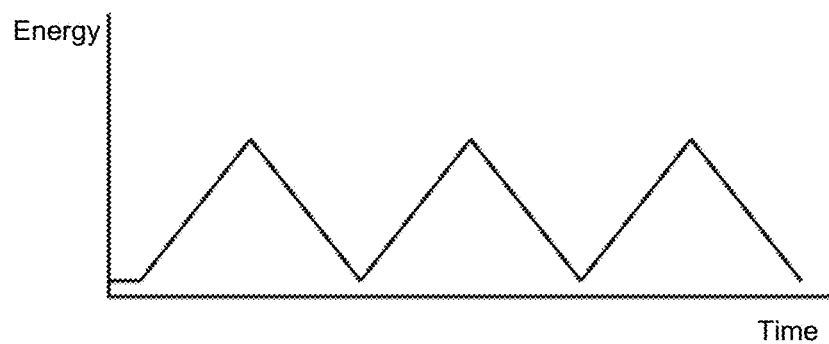
FIGS. 26a-26c illustrate examples of energy distribution.
Figure 26B:
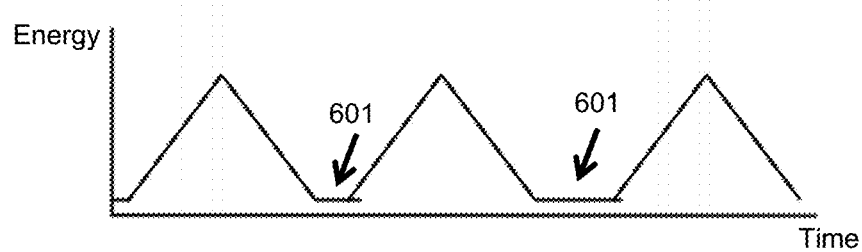
Figure 26C:
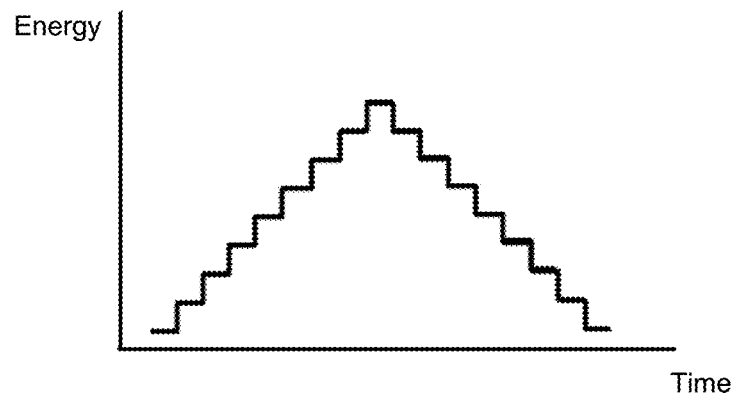

The energy distribution of the optical waves in time may have triangular shape shown on the FIGS. 26a-c. As shown on the FIG. 26a, triangle distributions may follow closely to each other. Alternatively, as shown on FIG. 26b, the triangle distributions may be separated from each other by intervals 601 of same and/or different length. Shown energy distribution is achieved by multiple steps of increase and decrease, wherein the overall steps create triangular shape, as shown on FIG. 26c.

Method of treatment may include autonomous treatment provided by the device including following steps choosing of body part to be treated; mapping of the tissue problem by the sensor; proposing and automatic modification of shape and dimensions of one or more treatment area; selection of shape and dimension of one or more treatment patterns; setting of threshold values of treatment parameters; setting of threshold ranges; choosing of treatment mode; transfer of optical waves to the tissue; measuring of treatment parameters and/or specifications of the tissue problems (e.g. color, shape and/or depth); response to measurement.

Method of treatment may include autonomous treatment. When the autonomous treatment is provided, almost all steps of the treatment may be provided by the device. Choosing of body part to be treated may be executed by operator and/or patient. All other steps including proposing and automatic modification of shape and dimensions of one or more treatment area, selection of shape and dimension of one or more treatment patterns, setting of threshold values of treatment parameters, setting of threshold ranges, transfer of optical waves to the tissue, measuring of treatment parameters and/or specifications of the tissue problems and/or response to measurement may be provided autonomously by the device, where the method may include correction and/or modification of the operation by device itself according to the measured information from the sensors.

Method of treatment may include semiautonomous treatment. When the semiautonomous treatment is provided, the device may provide autonomous treatment with possible correction and/or modification of its operation by the operator and/or patient during the treatment. The correction and/or modification of the operation may be done according to the measured information from the sensors, patient's needs and/or operator's needs.

The method of treatment may include of time-shifted optical waves (e.g. second laser). The scanning unit 102 may include crystal located in the way of the propagation of the second laser beam, which may cause time-shift of optical waves propagation. The time-shifted laser optical waves may be transmitted later than the first laser. Therefore the both lasers, particularly in pulse mode, may treat same optical spot (i.e. surface of tissue irradiated by optical spot). Such arrangement may be used for providing improved healing and/or rejuvenation to treated tissue. Similarly, using more than one optical beam may be used for removal of color irregularity, ablation of tissue and/or skin tightening. The second optical waves with different wavelength may provide healing effect.

Figure 27:
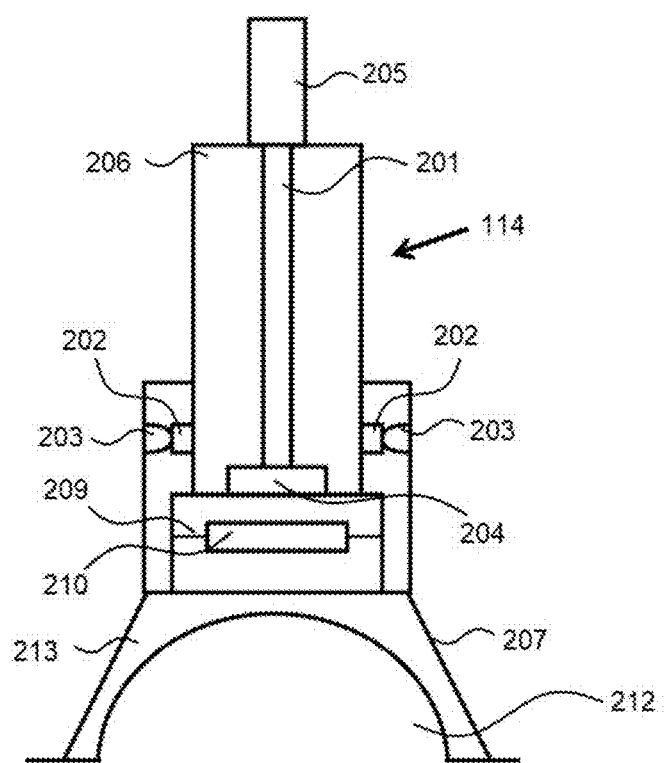
FIG. 27 illustrates an example of device using negative pressure.

Methods of treatment may also include application of a negative pressure before, during and/or after treatment by the energy. An exemplary handheld applicator capable of providing negative pressure is shown in FIG. 27, where the handheld applicator may include one or more cavities 213 formed by walls 207. The tissue 212 may be sucked into the cavity 213 by negative pressure generated by a source of negative pressure (not shown). Suitable sources of negative pressure include a vacuum pump located inside the device and/or external to the device but fluidly connected to cavity 213. Negative pressure may create a skin protrusion which may move the tissue closer to the lens 210. Negative pressure may also provide an analgesic effect. The negative pressure may be in the range of −100 Pa to −2 MPa, −3000 Pa to −400 kPa, or −4000 to −100 kPa. Deflection of the tissue caused by negative pressure may be in the range of 0.2 mm to 8 mm or 0.5 mm to 60 mm or 1 mm to 50 mm or 1.5 mm to 35 mm.

The negative pressure may be pulsed and/or continuous. Continuous pressure means that the pressure amplitude is continually maintained after reaching the desired negative pressure. Pulsed pressure means that the pressure amplitude varies, for example according to a predetermined pattern, during the therapy. Use of pulsed pressure may decrease inconvenience related to negative pressure by repeating pulses of tissue protrusions at one treated site, when the energy may be applied. The duration of one pressure pulse may be in the range of 0.1 seconds to 60 seconds, more preferably in the range of 0.1 seconds to 30 seconds, most preferably in the range of 0.1 seconds to 20 seconds wherein the pulse duration is measured between the beginnings of successive increases or decreases of negative pressure values.

Optical treatment may selectively heat the target biological structure. Optical treatment may remove and/or remodel e.g. adipose tissue. Before/after, with some overlap or simultaneously the magnetic treatment of the target biological structure may induce a muscle contraction within the target biological structure to remodel the adipose tissue by natural adipose tissue catabolism. Adipose tissue catabolism may be caused by apoptosis and/or necrosis of the adipocytes. The muscle contraction caused by induced eddy current may be equivalent to a natural muscle contraction. The adipose tissue may be reduced in natural way. Additionally, the muscle may be toned and/or shaped in a natural way. The treatment results may be significantly improved.

Preheating, precooling of the patient's soft tissue (e.g. muscle or adipose cells) by at least one treatment device may be done in temperature range from 25° C. to 60° C. or in range from 32° C. to 50° C. or in range from 36° C. to 45° C.

Heating or cooling of the soft tissue during the treatment may be provided by any treatment (e.g. RF adipose cells reduction) and may be combined with one or more any others treatment therapies (e.g. cellulite treatment, massage treatment, rejuvenation by optical waves and/or other).

The temperature of the tissue may be in the range of 30° C. to 105° C., more preferably in the range of 32° C. to 70° C., even more preferably in the range of 34° C. and 55° C., most preferably in the range of 35° C. and 44.5° C. Optionally, the temperature of the tissue may be increased in the range 40.5° C. and 43.5° C.

A cooling/heating mechanism may be used. In some embodiments air may be blown on the patient skin and/or sucked from the patient skin and/or on a protecting layer in order to control surface temperature, create a temperature gradient in the patient soft tissue, cool treatment energy sources (e.g. RF electrodes), cool the patient surface, do micro lymph drainage, remove moisture and/or make the treatment more comfortable. A cooling/heating function may be also provided by flow of a liquid, by thermal diffusion provided through solid, liquid, gel, gaseous material with good thermal conductivity and/or by thermoelectric method based on the Peltier effect.

Optical treatment may be applied before the magnetic treatment. The effect of the optical treatment may be stimulating, e.g. increasing the temperature of the target biological structure to prepare a target biological structure to be treated by magnetic treatment inducing at least muscle contraction. To enhance the efficiency of the treatment in some indications, it may be advantageous to preheat the tissue by infrared radiation prior to magnetic treatment or combined magnetic and optical treatment.

The optical waves may be applied to the treated biological structure such as a muscle or adipose cells for at least 1 minute, more preferably at least 5 minutes, even more preferably at least 15 minutes, most preferably at least 30 minutes or up to 120 minutes. The optical waves may be applied the treated biological structure in pulsed mode and/or in continually. The optical waves may raise a temperature of the treated biological structure. The optical waves may liquefy adipose cells.

Alternatively the effect caused by optical treatment may increase the temperature of the target biological structure, e.g. adipose cell or fibrous septae. It may be contributed by magnetic treatment causing at least muscle contraction. The at least muscle contraction may provide a massage effect for biological structures within proximity of the target biological structure, improve the blood and/or lymph circulation to improve local metabolism. Additionally the at least muscle contraction may reduce the number and/or volume of the adipose cells by energy used for the at least muscle contraction itself. Moreover, homogenous temperature distribution may be provided due to improved blood flow. Alternatively the at least muscle contraction may provide massage effect for promoting movement of fibrous septae.

The time-varying magnetic field may be applied to the treated biological structure with a repetition rate of at least 1 Hz, more preferably the repetition rate may be in a range of 0.1 to 700 Hz, even more preferably in the range of 0.5 to 200 Hz, or the range of 1 to 200 Hz, most preferably in the range of 1 to 80 Hz.

Simultaneous application of combined magnetic and optical treatment may reach more significant results than separate use of these treatments.

Simultaneous application of magnetic treatment and optical treatment may be administered in two modes: a first mode may generate the magnetic pulses while optical treatment is active or second mode may generate magnetic pulses while the optical treatment is not in an active treatment period, i.e. the period of magnetic treatment and optical treatment alternates.

The simultaneous application of magnetic treatment and optical treatment to the target biological structure may increase the peak magnetic component of the entire treatment resulting in improved heating of the target biological structure containing higher water volume, e.g. skin. Alternatively, the level of polarization of the optical radiation may be increased due to magnetic field, or a plane of polarization may rotate, e.g. Faraday's effect may occur. Due to increased temperature of skin, the production and/or remodeling of collagen and/or elastin fibers may be improved and the skin may be provided with a younger, smoother and enhanced appearance. The effect of overheating the muscle is reduced by the improved blood flow.

Optical treatment may also be used to attenuate the pain. Alternatively the repetition rate of the magnetic treatment may attenuate pain as well.

The optical waves may be generated by high power lasers. The optical waves may be applied to the treated biological structure. The time varying magnetic field may be applied to the treated biological structure as well. A repetition rate of the time-varying magnetic field may be at least 80 Hz, more preferably at least 100 Hz, most preferably at least 120 Hz. The repetition rate may be in a range of 100 to 250 Hz, more preferably in the range of 120 to 200 Hz, most preferably in the range of 140 to 185 Hz.

Alternatively the repetition rate of the time-varying magnetic field may be up to 80 Hz in order to improve adipose cells reduction as taught above.

The optical waves and the time-varying magnetic field may be simultaneously applied for at least 1 minute, more preferably at least 55 minutes, even more preferably at least 30 minutes, most preferably at least 60 minutes or up to 240 minutes.

Optical treatment may be applied after the magnetic treatment to provide contributing effect such as analgesic effect or it may further improve local metabolism. The magnetic treatment may induce at least muscle contraction or to stimulate a muscle structure to increase a muscular tonus of the target biological structure. Both effects may provide a massage effect for biological structures within the proximity of the target biological structure hence the blood and/or lymph circulation may be improved to promote local metabolism. The temperature may be locally increased by the improved blood flow and the target biological structure may accept the following optical treatment at significantly higher efficiency. Hence the muscle may be heated at higher quality. Additionally, the collagen and/or elastin fibers may be remodeled or restored and/or its neogenesis may be improved to provide a younger, smoother and enhanced skin appearance.

Additionally, previous application of magnetic treatment may improve acceptability of the optical treatment. The magnetic treatment may provide pain relieving effect for the biological structure hence the thermic effect caused by the optical treatment may be more tolerable for the patient.

Another benefit may be releasing the adipose cells from the muscle by at least muscle contraction and/or by temperature increase causing improved metabolism of adipose cells. Still another benefit of the at least muscle contraction may be mechanic breaking large adipose cells bulks into smaller bulks which may be easier removed by the lymphatic and/or blood flow. The liquidity of the smaller adipose bulks may be contributed by application of optical treatment. Due to improved liquidity, improved metabolism and/or blood circulation the cellulite may be treated in a short time and the visual effect on skin appearance may be significantly enhanced.

The treatment parameters of the magnetic field may vary as taught above. The treatment parameters may be e.g. repetition rate or magnetic flux density. The time duration may vary as well.

Optical waves may be also applied to attenuate the pain after the magnetic treatment.

The optical waves may be applied to the treated biological structure such as a muscle or adipose cells for at least 1 minute, more preferably at least 5 minutes, even more preferably at least 15 minutes, most preferably at least 30 minutes or up to 120 minutes. The optical waves may be applied the treated biological structure in pulsed mode and/or in continually. The optical waves may raise a temperature of the treated biological structure. The optical waves may liquefy adipose cells.

Combined treatments may be applied to one target biological structure to provide combined effect of magnetic and optical treatment. Alternatively the treatment may be applied to different target biological structures, e.g. optical treatment may be applied to at least adipose cell and magnetic treatment may be applied to at least one muscle fiber to improve local and/or adipose cell metabolism.

All applications of combined magnetic and optical treatment may amplify the resulting effect of the treatment. Therefore the results are achieved in significantly shorter time than the same results achieved by separate applications of the optical and magnet treatments. The treatment may be provided in various predefined treatment protocols focused on specific patient's needs, e.g. cellulite treatment, incontinence treatment, pain relieving etc. Each treatment parameter may be adjusted in the treatment protocol by the operator following the patient's needs. Alternatively the specific treatment may be designed by the operator for providing the most effective treatment following the patient's needs.

All the recited methods may be applied to a patient in a non-invasive and/or contactless way. Therefore the present methods provide an effective alternative approach of enhancing the visual appearance with no need of invasive treatment or surgery. Furthermore, the visual results are appreciable after several treatments. Additionally, the results include not only the visual appearance enhancement but even the improvement of the muscle structures hence the patient may feel firmer and tighter. The muscle structures may become toned with no need of any diet or spending time by exercising in fitness.

All the recited methods may be combined together and may be provided in various sequences to treat various issues during one treatment. Furthermore each application may induce a plurality of treatment effect, e.g. adipose cell reduction and/or reduction of cellulite.

The optical waves generating device may be placed in a distance up to 500 mm from the skin of the patient mm. Particularly in a range of 0.01 to 150 mm, more preferably in the range of 0.1 to 100 mm, even more preferably 1 to 50 mm, most preferably in the range of 2 to 25 mm.

The scanning unit may move over the tissue and stop in one or more predefined and/or random positions. Duration of the treatment may be in the range of 1 s to 90 min, more preferably in the range of 10 s to 75 min, even more preferably in the range of 30 s to 60 min, most preferably in the range of 1 to 30 minutes. The distance of the scanning unit from the tissue may be in the range of 0.5 cm to 100 cm, 1 cm to 80 cm or 3 cm to 65 cm. Scanning speed, defined as time change of distance of two focal point, may be in the range of 0.01 cm/s to 150 cm/s, more preferably in the range of 0.05 cm/s to 100 cm/s, most preferably in the range of 0.1 cm/s to 80 cm/s.

Applied optical waves may be electromagnetic waves, e.g. UV radiation, light, IR radiation, radiofrequency waves and/or microwave waves. Optical waves may be coherent, non-coherent, depolarized, polarized, monochromatic or polychromatic. The wavelength of the optical waves may be in the range of 200 nm to 15000 nm, more preferably in the range of 250 nm to 10000 nm, even more preferably in the range of 300 nm to 5000 nm, most preferably in the range of 400 nm to 3000 nm. The optical waves may be combined with the magnetic treatment, i.e. the optical and the magnetic field may be applied to the patient.

Optical waves may be also applied in the narrower spectral band. Some of the spectral bands may represent different colors of the visible part of the electromagnetic spectrum. The wavelength of the applied optical waves may be close to 254 nm, 405 nm, 450 nm, 532 nm, 560 nm, 575 nm, 635 nm, 660 nm, 685 nm, 808 nm, 830 nm, 880 nm, 915 nm, 970 nm, 980 nm, 1060 nm, 1064 nm, 1320 nm, 1440 nm and/or 1470 nm. Term "close to" refers to deviation of 20%, more preferably 15%, most preferably 10% from the nominal wavelength. Optical waves in the range of 620 to 750 nm may be beneficial for local circulation enhancement and restoration of connective tissue. Optical waves in the range of 400 to 500 nm may provide bactericidal effect; optical waves in the range of 560 to 600 nm may stimulate tissue rejuvenation. Wavelength may be changed during treatment. Method of treatment may include application aiming beam of any visible (e.g. red, blue, green or violet) color, i.e. specific wavelength and/or spectra.

Optical waves may be applied in one or more beams. One beam may include optical waves of more than one wavelength, e.g. when the optical waves are provided by more sources of different intensity. One beam may provide an optical spot having an optical spot size defined as a surface of tissue irradiated by one optical beam. One optical waves generating device may provide one or more optical spots e.g. by splitting one beam to plurality of beams. The optical spot size may be in the range of 0.001 $cm^2$ to 600 $cm^2$, more preferably in the range of 0.005 $cm^2$ to 300 $cm^2$, most preferably in the range of 0.01 $cm^2$ to 100 $cm^2$. Optical spots of different and/or same wavelength may be overlaid or may be separated. Optical spots may be separated by at least 1% of their diameter; optical spots may closely follow each other and/or be separated by a gap ranging from 0.1 cm to 20 cm. Optical spot may have any shape, e.g. circular shape. In case of application of more than one optical beams, the controller may control the treatment parameters of every optical beams independently.

Optical waves output may be up to 300, 250, 150 or 100 W. Optical waves may be applied in continuous manner or in pulses. Pulse frequency may be in the range of 0.2 Hz to 100 kHz, more preferably in the range of 0.25 Hz µs to 40 kHz, most preferably in the range of 0.4 Hz to 25 kHz. The pulse width may be in the range of 0.1 µs to 10 s, more preferably in the range of 25 µs to 5 s, even more preferably in the range of 50 µs to 2.5 s, most preferably in the range of 100 µs to 1000 ms. Pauses between two pulses may last 50 µs to 1 s, more preferably in a range of 1 ms to 1 s, most preferably in the range of 1 ms to 45 ms.

Pulse energy of the optical waves may be in the range of 0.1 mJ to 100 mJ, more preferably in the range of 0.5 mJ to 75 mJ, most preferably in the range of 1 mJ to 50 mJ. Energy density of the optical waves beam may be in the range of 0.1 $J/cm^2$ to 3000 $J/cm^2$, more preferably in the range of 1 $J/cm^2$ to 1500 $J/cm^2$, most preferably in the range of 5 $J/cm^2$ to 1000 $J/cm^2$.

The energy flux density of optical waves during the pulsed mode may be in range between 0.05 $mW/mm^2$ to 13 $W/mm^2$, more preferably in the range of 0.05 $mW/mm^2$ to 6 $W/mm^2$, even more preferably in the range of 0.05 $mW/mm^2$ to 2 $W/mm^2$, most preferably in the range of 0.05 $mW/mm^2$ to 0.6 $W/mm^2$.

Applied optical waves may be high level light. In this case, the output of the optical waves generating device may be in the range of 0.1 to 300 W, more preferably in the range of 0.2 to 75 W, even more preferably in the range of 0.35 W to 60 W, most preferably in the range of 0.5 to 50 W.

Energy flux density provided by optical waves in pulse mode may be in the range of 0.005 $W/cm^2$ to 75 $W/cm^2$, more preferably in the range of 0.01 $W/cm^2$ to 60 $W/cm^2$ and most preferably in the range of 0.01 $W/cm^2$ to 50 $W/cm^2$.

The energy flux density of optical waves during the continual mode may be in range between 0.05 $mW/mm^2$ to 1.2 $W/mm^2$, more preferably in the range of 0.05 $mW/mm^2$ to 0.63 $W/mm^2$, even more preferably in the range of 0.05 $mW/mm^2$ to 0.4 $W/mm^2$, most preferably in the range of 0.05 $mW/mm^2$ to 0.2 $W/mm^2$.

The magnetic treatment may be combined with mechanical treatment such as application of mechanical waves and/or a pressure. The target biological structures may be treated by the mechanical treatment and/or by the magnetic field simultaneously, alternating and/or in overlap. The application of mechanical waves may e.g. positively influence a metabolism of adipose cells, alternatively massage effect may be provided by the mechanical treatment. The magnetic and/or mechanical treatment may be applied by one treatment device generating the time-varying magnetic field and the mechanical treatment, or the treatments may be applied by at least two separate treatment devices.

The positive and/or negative pressure may be applied to the patient to promote at least blood and/or lymph flow. The negative pressure refers to pressure below atmospheric pressure. The positive pressure refers to pressure value above atmospheric pressure. Atmospheric pressure is pressure of the air in a room during the treatment. The pressure may be provided by a vacuum, a fluid flow or by a pressure changing element (e.g. a massaging element or pressure cells).

The mechanical treatment may cause synergic effects in combination with the treatment by the magnetic field. Hence the combined treatment may provide improved effectively of the treatment and/or reduced treatment time. Further the visual results are achieved in shorter time period.

Figure 10A:
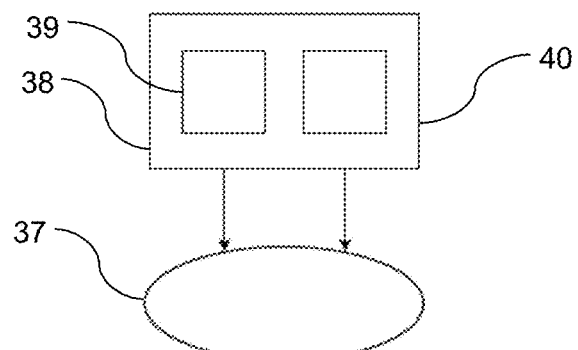
FIGS. 10a and 10b illustrate diagrams of a treatment device and/or an applicator providing magnetic and/or mechanical treatment.
Figure 10B:
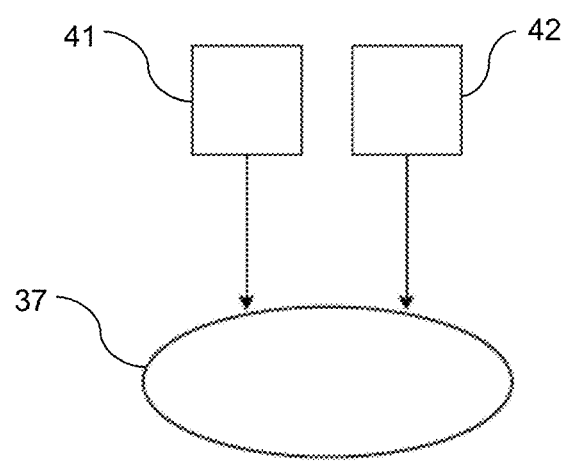

FIGS. 10a and 10b illustrate an applicator/a device providing the combined treatment to the body region of the patient 37.

FIG. 10a illustrates a treatment device 38 including a connection to power source, a magnetic field generating device 39 and mechanical waves and/or pressure generating device 40.

Alternatively the treatment device may include at least one device generating both, the magnetic field and the mechanical wave and/or pressure. Such a device may be the magnetic field generating device, e.g. a magnetic field generating device, including a metal or ferromagnetic material within proximity of the magnetic field generating device. The generated mechanical wave may be shock wave generated by electromagnetic principle. Alternatively the mechanical wave may be a vibration.

FIG. 10b illustrates alternative treatment applied to the patient 37 by two separate treatment devices, i.e. by a device providing magnetic treatment 41 and a device providing mechanical waves and/or pressure 42.

An applicator providing mechanical treatment to the patient may be separate from the applicator including a magnetic field generating device. Alternatively, the mechanical treatment and the time-varying magnetic field may be provided to the patient by a common applicator. Alternatively applicator providing mechanical treatment may be attached to the applicator providing the time-varying magnetic field or vice versa. Alternatively the mechanical applicator may be separate from the magnetic applicator and both applicators may be removably attached to a common mechanical fixture.

The treatment effect may be enhanced by applying negative pressure to the skin below the applicator. The negative pressure may be in the range of 1 Pa to 50 kPa below the atmospheric pressure, preferably in the range of 0.1 to 25 kPa below the atmospheric pressure, more preferably in the range of 1 to 15 kPa below the atmospheric pressure, most preferably in the range of 3 to 8 kPa below the atmospheric pressure. The skin may be pulled towards the inner surface of the applicator. Hence a contact may be enabled by applying the negative pressure. Further the skin may be stretched and a thickness of the skin may decrease. Alternatively the blood and/or lymph flow may be promoted.

The treatment effect may be enhanced by application of a positive pressure. The dermal blood flow may also be limited and/or eliminated by applying a constant static pressure. The pressure greater than systolic blood pressure may be used for temporary pushing the blood out of the dermal and/or subcutaneous veins. Alternatively the pressure application may provide correct contact of the applicator with the patient's skin.

Further the positive pressure may follow a predetermined pattern to provide a massage effect. A varying pressure may increase the blood and/or lymph flow. The local metabolism may be promoted. Alternatively a regeneration of the treated body region may be promoted as well.

The pressure may be alternatively applied by an applicator designed to correspond to the patient's body shape. The applicator may include at least one pressure applying element, more preferably a plurality of pressure applying elements may be used. An exemplary device may be e.g. a massage roller. A movement of the roller may follow a predetermined trajectory.

Alternatively the positive pressure may be applied by a flexible applicator which may be shaped to fit the patient's body, e.g. in a shape of a compression bag, a sleeve, trousers, shorts, a shirt, a jacket or other garment. The device may treat one or multiple body parts. The patient's body part such as a limb may not be entirely within or under the applicator. The plurality of body parts may be treated simultaneously.

One or more applicators may treat the body part individually and/or may be interconnected and may cooperate. Massage units may be designed for providing lymph drainage.

A correct placement of the compression sleeve may be provided by anatomical design of the applicator and/or at least one sensor. The correct placement may be important for improving a flow and/or propelling the lymph to lymphatic nodes.

The applicator may include at least one pressure changing element, such as a pressure cell or a rigid member, providing a massage to the patient. The at least one pressure changing element may move with respect to the patient. The movement may be rotational and/or translational. A plurality of pressure changing elements may create a pressure gradient.

The applicator may include at least one sensor for providing feedback. A treatment protocol may be adjusted automatically based on the feedback, semiautomatically and/or manually by the operator. Semiautomatically may be interpreted in the sense that a control system may provide a recommended adjustment of the treatment protocol which may be confirmed by the operator.

The device may be automatically controlled hence continual monitoring by the operator is not needed. It may reduce time duration and/or costs of the treatment. The operator may supervise more than one treated patient. Self-operated or automated devices may prevent mistakes during the treatment caused by human factors. Further benefit of the self-operated device may be an absence of the need for a skilled operator as when using a manual device.

A number of pressure changing elements may be up to 6000, preferably in the range of 1 to 1000, more preferably in the range of 8 to 80, even more preferably in the range of 2 to 40, most preferably in the range of 4 to 32.

A size and/or the shape of the pressure changing element may fit to the patient's body. One pressure changing element may apply the pressure to the patient's skin in an area of at least 0.1, 1, 10, 100, 1000 $cm^2$ or up to 2 $m^2$. In an exemplary application the area may be in the range of 1 $cm^2$ to 1 $m^2$, more preferably in the range of 10 $cm^2$ to 1000 $cm^2$, even more preferably in the range of 40 $cm^2$ to 800 $cm^2$, most preferably in the range of 150 $cm^2$ to 600 $cm^2$.

At least one pressure changing element may continually change the applied pressure. Alternatively the pressure may be changed in intervals, e.g. in the range of 5 ms to 10 s, more preferably in the range of 0.1 to 5 s, most preferably in the range of 0.5 to 2 s. A plurality of pressure changing elements may provide the pressure simultaneously and/or sequentially, i.e. the pressure changing elements may be switched in applying the pressure.

The method may change the positive and/or the negative pressure in time. A pressure change may be linear, exponential, logarithmic or sinusoidal. The pressure applied may be changed. Alternatively the applied pressure may create a pressure gradient. The pressure gradient may vary within the treatment. In preferred application the pressure gradient may propel the lymph to lymphatic nodes. Alternatively the pressure gradient may propel the lymph in reverse direction to physiologic lymph flow. A treatment protocol may influence the treated biological structure and/or a layer of the skin. The treatment protocol may be predefined and/or adjustable by the operator following the patient's needs.

The pressure gradient may arise between at least two pressure changing elements. The pressure gradient may be in the range of 0 to 100%, preferably in the range of 0 to 95%, more preferably in the range of 0 to 70%, most preferably in the range of 0 to 50%. In an exemplary application the pressure gradient may be 1%, i.e. the applied pressure between current and following pressure value decreases and/or increases with the pressure gradient of 1%. In an exemplary application the current pressure value may be 5 kPa and the following pressure value may be 5.05 kPa if the gradient increases or 4.95 kPa if the gradient decreases.

Cycles of the treatment, e.g. repeated pulse sequences, treatment patterns, repeated parts of the treatment protocols and/or its duration may vary following the patient's needs. A treatment pattern may be a line or a matrix. The pressure changing element may move in trajectories including linear, circular and/or curvilinear motion. Alternatively the motion may correspond to the patient's lymphatic system. A motion speed of the pressure changing element may vary. The speed be in the range of 0.1 and 50 cm/s, more preferably in the range of 1 to 30 cm/s, most preferably in the range of 5 to 15 cm/s.

The method may be applied to different body regions such as arms, legs, buttock, hips, torso or abdomen. The treated area may be at least 0.1 $mm^2$, 1 $mm^2$, 1 $cm^2$, 10 $cm^2$, 25 $cm^2$, 50 $cm^2$ or more. The treated area may be in range 0.1 $mm^2$ to 2 $m^2$, preferably in the range of 1 $mm^2$ to 1 $m^2$, more preferably in the range of 1 $cm^2$ to 500 $cm^2$, most preferably in the range of 2 $cm^2$ to 100 $cm^2$.

The applied pressure may be at least 0.1, 0.5, 1, 10, 60, 200 kPa or up to 400 kPa. The applied pressure may be in the range of 10 Pa to 30 kPa, more preferably in the range of 100 Pa to 20 kPa, even more preferably in the range of 500 Pa to 19 kPa, most preferably in the range of 1 kPa to 15 kPa.

The patient's skin may deflect by the applied positive pressure applied of at least 0.1, 0.5, 1, 2, 5, 10, 50, 100 mm or more. In the case of negative pressure applied the skin may be deflected oppositely.

The applied pressure may last at least 1 ms, at least 0.5, 1, 5 or 30 s. Alternatively, the pressure may be applied for 1, 5, 10, 20, 30, 45, 60 minutes or up to 2 hours. In exemplary applications the pressure may be applied for a time period in the range of 1 s to 5 min or in the range of 2 to 30 s. Values of applied pressure may vary during the cycles.

The following table illustrates exemplary treatment protocols

| Name | Recommended pressure range [kPa] | Recommended time [min] | Characteristic and effects of the program |
|---|---|---|---|
| Massage | 5-11 | 30 | The pressure cells are inflated and deflated in succession. The effect is similar to manual massage. |
| Physiological | 3.5-9.5 | 30 | Contributes a rehabilitation of the vascular system. |
| Preparation | 3.5-9.5 | 20 | Treatment of body's tissues before further lymphatic treatment. |
| Lymph drainage | 3.5-9.5 | 45 | Similar to manual lymphatic massage. The most suitable program for aesthetic medicine. |
| Elephantiasis | 3.5-11 | 45 | The pressure cells are inflated in succession and remain inflated. Improve lymph flow. |

-continued

| Name | Recommended pressure range [kPa] | Recommended time [min] | Characteristic and effects of the program |
|---|---|---|---|
| Venopress | 2.5-7 | 30 | The program for increasing blood flow in peripheries. Helps to prevent vascular problems. |
| Embrocation | 3.5-9.5 | 45 | Sequential inflating of single pressure cell in order to ensure careful removing of lymphatic fluid. |
| Reversed combi | 3.5-9.5 | 45 | Pressure cells are inflated in preset pattern. Successively pushing the lymphatic mass proximally. |

The combined treatment using the magnetic field and application of pressure to the patient may provide a massage effect, improve blood and/or lymph circulation or provide anti-edematous effect. A removing of the adipose cells, local metabolism including the local metabolism of the adipose cells, elastogenesis and/or neocollagenesis may be accelerated. The adipose cells may be reduced by natural catabolism. Due to improved blood and/or lymph circulation a panniculitis may be prevented. Erythema may also be reduced.

The skin tightening effect may occur. Hence the skin appearance may obtain younger and smoother appearance.

Further improved regeneration of the treated biological structure such as a muscle may be promoted hence a muscle fatigue may occur after longer time period and the treatment may last longer. Enhanced results may be achieved compared to the treatment by single methods.

The magnetic treatment may be combined with application of mechanical waves. One type of mechanical waves may be shock waves and/or acoustic waves which are characterized by steep pressure amplitude growth in comparison to the surrounding pressure. The shock wave is further characterized by non-linearity during the propagation. The positive peak pressure is above 0.1 MPa, more preferably 3 MPa, even more preferably at least 7 MPa, most preferably at least 15 MPa or up to 150 MPa. The pulse duration of the shock wave (based on the time the pressure exceeds a half value of peak positive pressure) may be preferably in the range of hundreds of nanoseconds to tens of microseconds, e.g. shock wave pulse may last in a range of 200 ns to 30 µs, preferably in the range of 400 ns to 15 µs, more preferably in the range of 400 ns to 2.5 µs, most preferably in the range of 800 ns to 1.5 µs.

The pulse width of a shock wave pulse positive phase may be in a range of 0.1 µs to 30 µs, preferably in the range of 0.5 µs to 10 µs, even more preferably in the range of 0.7 µs to 5 µs, most preferably in the range of 0.8 µs to 2 µs. The rise time of a shock wave pulse may be in a range of 50 ns to 2000 ns, preferably in the range of 60 ns to 1000 ns, more preferably in the range of 70 ns to 700 ns, even more preferably in the range of 80 ns to 500 ns, most preferably in the range of 100 ns to 400 ns.

An energy of one energy pulse may be in a range of 1 to 1000 mJ, preferably in the range of 5 to 700 mJ, more preferably in the range of 10 to 500 mJ, even more in the range of 25 to 350 mJ, most preferably in the range of 50 to 200 mJ, The energy of the pulse may be adjustable by the operator.

Shock waves may propagate naturally non-focused/radial, planar or moderately focused. Non-focused/radial, planar shock waves are characterized by smooth/soft propagation and therefore these waves are preferred. A pneumatic principle of generating shock waves may be performed by pressurized gas vibrating a percussion guide or by ballistic shock waves which may be generated by striking of a bullet inside a guiding tube to a percussion guide. The bullet may be accelerated by pressurized gas, electric field, magnetic field, spring or other technique. The applicator including the shock waves generator may be preferably positioned in a direction perpendicular to the skin of the patient.

Shock waves may differ from ultrasound waves. The difference may be in waveform and/or in its propagation. Significant differences may also be in physical effect of ultrasound and shock waves on the treated tissue, particularly a cavitation effect. Shock waves may reduce the cavitation and the violent break up of cells resulting from the cavitation.

The treatment method may use the magnetic treatment and the treatment by shock waves enabling improvement of the biological structure such as soft tissue, e.g. a connective tissue in the skin area such as collagen, elastin and/or adipose cells in epidermis, dermis, hypodermis and/or in peritoneal cavity. The structures below the skin such as a muscle may remain untreated and/or unharmed. Alternatively the treatment may also create micro-disruptions of the treated tissue, create a movement, rotation or polarization of particles by the magnetic field. The improvement of the connective tissue may be promoted by collagen and/or elastin generation and/or remodeling. Alternatively the adipose cells may be reduced. The blood and/or lymph flow may increase. The shock waves may be applied to a body region in a range of 1 $cm^2$ to 2 $m^2$, more preferably in the range of 50 $cm^2$ to 1.75 $m^2$, most preferably in the range of 100 $cm^2$ to 1.5 $m^2$.

The combined treatment may result in increased cell membrane permeability, which may result in increased liquefying of adipose cells or lipolysis. Combination of both treatment methods may highly reduce a risk of adipose cells inflammation.

The combined treatment may improve lymph and/or blood flow. Further the treatment by shock waves may provide a pain relief and/or myorelaxation effect. Similar effects may also be provided by the treatment methods using the magnetic field hence the effect may be provided by two different synergic treatments. The results achieved by combined treatment are more significant than results achieved by single method application.

The shock waves may be applied to the patient prior, during and/or after applying the magnetic field to the patient.

The shock waves applied prior the application of magnetic field may mechanically disrupt larger clusters of adipose cells to smaller clusters which may be better treated by the magnetic field.

Treatment may be applied to the patient, particularly to the body region including calf, thigh, saddlebag, buttock, abdomen, love handle, bra fat region, arm, face, neck, breast, shoulder and/or thorax. The present method may be used for treatment of sexual issues such as erectile dysfunction. Treatment may be targeted to the cavities of the body, e.g. mouth, vagina or anus.

The applicator may be moved along the lymphatic vessels. The treatment may increase the velocity of lymph flow in lymph vessels. Proper movement of the applicator may be performed by the operator via direct or indirect control and/or by a robotic system. The applicator may be moved in continuous longitudinal movements. Alternatively the movement may be of any shape e.g. a loop, circular and/or random. The applicator may also be moved in straight line. The movement of the applicator may be in a direction from the center of the treated body part to its periphery. Movement of the applicator may also be in the direction from the periphery of the treated body part towards the body. Continuous movement may be directed to one or more lymph nodes e.g. lymph nodes in the groins. Exemplary treatments may be found in U.S. patent application Ser. No. 15/471,946.

A cream or a lotion may be topically applied on the skin of the patient in order to prevent friction forces which may occur between the skin and the applicator including the energy delivery element. The cream or lotion may be preferentially applied prior to the application of shock waves. The cream or lotion may include any substance for enhancing treatment effect. At least a contact part of the applicator, e.g. energy delivery element, may be cover by a sleeve or tip in order to prevent damaging the applicator by the cream or lotion applied onto the skin in the body region. The sleeve or tip may be preferably made of fluid resistant material such as silicone or any other biocompatible material.

Alternatively skin may be manually folded and shock waves may be applied to the skin fold.

A repetition rate of the shock waves may be in the range of 0.1 to 100 Hz, more preferably in the range of 0.5 to 50 Hz, most preferably in the range of 1 to 40 Hz. The shock waves may be applied in burst mode. Each burst may include one train of subsequent shock waves and a time period of no shock waves application. The burst duty cycle may be in a range of 1 to 99%, preferably in the range of 2 to 90%, more preferably in the range of 5 to 75%, even more preferably in the range of 10 to 60%, most preferably in the range of 15 to 50%. Exemplary train may include at least two shock waves, preferably 4, 8, 12, 16 or 20 shock waves. The number of shock waves within the train may be independent on the repetition rate of the shock waves. One treatment session may include applying a plurality of shock waves to the body region. A total number of the waves within one treatment session may be at least 250, preferably at least 500, more preferably at least 1000, even more preferably at least 2000, most preferably at least 5000 or up to 20000. The treatment session may last in order of seconds, e.g. 5, 10, 15, 30 or 45 seconds, or preferably in order of minutes such as 2, 5, 10, 15, 20, 30 or more minutes.

An energy flux density of the shock wave may be in the range of 0.001 and 160 mW/mm$^2$, more preferably in the range of 0.001 to 100 mW/mm$^2$, most preferably in the range of 0.001 to 50 mW/mm$^2$.

Methods may include a direct contact of the applicator with the tissue which may result in a deflection of the tissue by the applicator. The deflection may be in the range of 0.01 to 30 mm, 0.02 to 20 mm or 0.05 to 10 mm.

A surface of an energy delivery element providing shock waves may be at least 0.01 cm$^2$, preferably in the range of 0.05 to 50 cm$^2$, more preferably in the range of 0.75 to 40 cm$^2$, most preferably in the range of 0.1 to 35 cm$^2$.

The direct contact of the applicator with the tissue may form a recess in the tissue during the treatment. The recess may be in the range of 0.01 to 80 mm, 0.1 to 60 mm, 0.5 to 40 mm or 0.1 to 35 mm.

The magnetic field and shock waves may be applied with a ratio which may provide significant results, optimal treatment and minimal adverse effects. The ratio between the repetition rate of the magnetic field and the frequency of shock waves (Hz/Hz) may be in the range of 0.001 to 50, more preferably in the range of 0.02 to 30, most preferably in the range of 0.06 to 15.

The time-varying magnetic field may be applied to a body region simultaneously with the shock waves. Alternatively the time-varying magnetic field may be applied to the body region separately, i.e. prior or after shock waves. Alternatively the shock waves may be applied to first body region and the time-varying magnetic field may be applied to second body region different from the first body region. Alternatively shock waves may be applied to first location of the body region and the time-varying magnetic field may be applied to second location of the same body region, e.g. applying shock waves to left abdominal area and applying the time-varying magnetic field to right abdominal area or vice versa.

The shock wave treatment may be preferably repeated at least two time, more preferably at least five time, most preferably ten times or more. A repetition of the treatments by shock waves may be once a day, two to five times a week, once a week, once in two-weeks or once a month. Alternatively at least one treatment by time-varying magnetic field may alternate with the shock wave treatment, e.g. a plurality of treatments by time-varying magnetic field may be applied to the patient between the subsequent treatments by shock waves.

Another type of mechanical waves may be ultrasound waves. Ultrasound waves are characterized by periodic pressure oscillation during propagation and possible cavitation effect within the target biological structure, e.g. in adipose tissue.

A cavitation is a formation of gas bubbles in a fluid environment which occurs during a negative pressure wave in a liquid. Ultrasonic cavitation bubbles represent acoustic inhomogeneity in which incoming acoustic energy is absorbed and dissipated. Due to high frequency of the ultrasound waves, the acoustic energy may cause rapid growth of cavitation bubbles and cavitation effects, with breakup of the bubbles and violent damage of the surrounding tissue, e.g. adipose cells.

A rate of generating such microdamages may be in the range of 1 to 1 000 per second, preferably in the range 5 to 800 per second, even more preferably in the range 10 to 750 per second, most preferably in the range of 50 to 500 or up to 10 000 per second. Alternatively the rate of generation the microdamages may be higher.

The ultrasound waves may be focused, unfocused or weakly focused.

Generally, the ultrasound waves are generated in a frequency range from 100 kHz to 100 MHz, preferably in the range of 1 to 20 MHz, more preferably in the range of 2 to 12 MHz, even more preferably in the range of 3 to 10 MHz, most preferably in the range of 4 to 7 MHz. The frequency of the generated ultrasound waves may vary depending on an application, a depth of penetration and/or a target biological structure.

Ultrasound waves of power density up to 1 W/cm$^2$ and frequency in the range of 1 to 20 MHz may be used for medical imaging. Imaging ultrasound waves may be used for targeting the target biological structure which may be treated. Imaging ultrasound waves avoid heating and/or the cavitation effect due to low power density.

A power of the treatment ultrasound waves used for the present method may be in the range of 0.1 to 200 W, preferably in the range of 0.5 to 100 W, more preferably, even more in the range of 1 to 50 W, most preferably in the range of 2 to 20 W, or up to 10 kW.

A power density of the ultrasound waves may be in the range of 0.1 W/cm$^2$ to 1 kW/cm$^2$, more preferably in the range of 10 to 500 W/cm$^2$, most preferably in the range of 20 to 100 W/cm$^2$.

Energy applied to the target biological structure may be 0.1, 1, 10, 50, 100, 500 J or more. An exemplary applied energy may be in the range of 0.1 J to 1 kJ, preferably in the range of 1 to 500 J, more preferably in the range of 5 to 250 J, most preferably in the range of 10 to 100 J.

A frequency of the ultrasound waves used for an aesthetic treatment may be in the range of at least 100 kHz, e.g. in the range of 0.5 to 100 MHz, preferably in the range of 1 to 50 MHz, more preferably in the range of 2 to 30 MHz, even more preferably in the range of 3 to 20 MHz, most preferably in the range of 5 to 15 MHz. The frequency may vary within one treatment. A plurality of ultrasound waves of different frequency may be applied to achieve different treatment effects such as ablation, coagulation, cavitation or non-thermal effect.

The ultrasound waves may be applied in pulses. Time duration of the pulses may be in the range of 1 µs to 60 s, more preferably in the range of 1 to 5000 ms, even more preferably in the range of 5 to 750 ms, most preferably in the range of 50 to 500 ms. Alternatively the ultrasound pulses may be applied in bursts including a plurality of subsequent ultrasound pulses. A time period between two subsequent ultrasound pulses may be in a range of 5 ms to 120 s, more preferably in the range of 10 ms to 5 s, most preferably in the range of 20 ms to 2 s. Alternatively the ultrasound waves may be applied continuously.

A repetition rate of the pulses may be at least 0.1, 5, 10, 25, 50, 100 Hz, or more. The high repetition rate of the pulses in order of kHz may also be used, e.g. 1 or 5 kHz.

Further, ultrasound waves may generate heat within the target biological structure, e.g. adipose cells. A temperature of the target biological structure may be e.g. in the range of 37 to 60° C. or in the range of 43 to 48° C. Apoptosis of the adipose cells may be induced. The treatment device may include a temperature sensor for adjusting the power of the ultrasound waves to maintain the target biological structure within optimal temperature range.

The treatment may last at least 5 seconds, preferably at least 1, 5, 10, 20, 30, 60 minutes or up to 240 minutes.

An applicator may be moveable. A motion of the applicator may follow a predetermined trajectory, e.g. scanning motion may be used. Alternatively zig-zag, curvilinear or circular motion may be used.

The treatment device may calculate a correct speed of the motion. Further the speed of the motion may be monitored by at least one sensor and the treatment device may provide information to the operator. A human machine interface may notify the operator in a human perceptible form that the speed of the motion is incorrect. A notification may be visual, e.g. flashing light or light change; audible such as beep; or mechanically perceptible form such as vibration of the applicator. The speed may be adjusted following the patient's needs.

Following the speed of the motion the pulses may be spaced apart in distances in the range of 0.01 to 25 mm, more preferably in the range of 0.1 to 10 mm, even more preferably in the range of 0.5 to 5 mm, most preferably in the range of 1 to 3 mm.

The target biological structure such as adipose cells in a fat layer may be targeted by imaging ultrasound. The imaging ultrasound may be used for adjusting the frequency, focus and/or energy of the treatment ultrasound. The ultrasound energy may be delivered to the target biological structure where the cavitation effect or heat may be generated.

A specific depth of the fat layer may be treated due to specific penetration depth and/or the focus which may be adjusted by the operator. The specific depth may be at least 1, 5, 10, 25, 50, 100, 150 mm or more. Exemplary depth may be in the range of 0 to 150 mm, more preferably in the range of 1 to 100 mm, even more preferably in the range of 5 to 50, most preferably in the range of 5 to 30 mm.

Alternatively the treatment method may be applied to shallow layers of the skin such as in the depth up to several millimeters, e.g. in the range of 0.01 to 20 mm, more preferably in the range of 0.1 to 10 mm, even more preferably in the range of 0.2 to 5 mm, most preferably in the range of 0.75 to 3 mm.

An ultrasound waves generating element may be coupled to the patient's skin. Alternatively the ultrasound waves generating element may be in the applicator in mechanical waves transmitting medium, e.g. a fluid such as water or oil, alternatively rigid transmitting medium may be used. The ultrasound waves transmission from the applicator to the patient may be enabled by ultrasound gel.

The treatment method may be used for reducing adipose cells in number and/or in volume, further the method may reduce cellulite appearance. The treatment may cause lipolysis, preferably apoptosis of the adipose cells. Adipose cell metabolism may also be increased. Further blood and/or lymph flow or local metabolism may increase.

The treatment by ultrasound waves may be preferably combined with another mechanical treatment which may provide physical damage of large adipose cells cluster to smaller clusters to provide enhanced results. Further the combined mechanical treatment method may move and/or stretch the fibrous septae hence the cellulite appearance may also be reduced.

Alternatively the method may be used for enhancing a visual appearance of a skin. Enhancing the visual appearance of the skin may be interpreted as an increase of skin elasticity or collagen and/or elastin production; reduction of adipose cells in number and/or volume, scars, stretch marks, wrinkles or circumferential reduction. Enhancing the visual appearance of the skin may result in skin rejuvenation or skin tightening effect, skin laxity may also be reduced.

The treatment may be applied to the face of the patient. The skin compartments, e.g. elastic fibers such as collagen or elastin may be remodeled and/or a new production of the elastic fibers may be promoted. Non-invasive treatment method reduces downtime for recovery comparing to currently used invasive methods. Further the method may be comfortable for the patient.

In general the mechanical treatment may be applied prior, during or after the treatment by magnetic field. The blood and/or lymph flow may be increased, metabolism may be improved. Further collagen and/or elastin production may increase.

Shock, acoustic and/or ultrasound waves may break large clusters of adipose cells into smaller clusters which may be better metabolized. The shock wave may also provide a relaxation effect for the treated body region hence the treated body region may be prepared for the following magnetic treatment.

Alternatively shock waves may be applied after the magnetic treatment to promote lipolysis and/or adipose cells apoptosis influencing ER stress which may result from the applied magnetic field prior the shock waves application.

Alternatively the positive and/or negative pressure application may prepare a metabolism for the treatment by magnetic field.

The ultrasound waves applied prior the magnetic field may cause damages to adipose cells, e.g. a disruption. Further the ultrasound waves may heat the adipose cell and/or liquefy the adipose tissue. The adipose cells may be metabolized at higher quality by the following magnetic treatment promoting local metabolism, blood and/or lymph flow. Further the applied magnetic field may promote a lipolysis by the muscle contraction.

Exemplary application of a combined treatment may be application of ultrasound waves for damaging the adipose cells followed by the magnetic treatment. The shock waves may be subsequently applied to promote a lymph circulation and/or enhance metabolism of the treated adipose cells.

Another exemplary application may be application of positive and/or negative pressure simultaneously with the magnetic field. The local metabolism, blood and/or lymph flow may be improved as well. Further skin tightening effect may be achieved.

The time-varying magnetic field may treat biological structures below the skin such as a muscle. Induced muscle contraction may move the skin layer. On the other hand, the mechanical treatment may influence the skin, the layers below the skin may be less influenced due to dissipation of the pressure within the skin layers. Combination of the mechanical treatment and the magnetic treatment may provide a complex treatment method enhancing visual appearance of the patient's body by, e.g. reducing adipose cells or cellulite appearance; providing smoother skin and/or increasing skin elasticity or shaping the muscle. The combined treatment may achieve the treatment effect in significantly shorter time periods compared to single treatment methods.

The magnetic field may be combined with application of heat and/or cold. The body region may be heated/cooled. The target biological structures may be selectively treated due to different tolerance of various biological structures to heating/cooling. Applying of heat/cold may improve metabolism of the biological structure, alternatively a reduction of the biological structure may occur.

The magnetic treatment may be combined with optical treatment. The optical treatment may be used for remodeling, reducing the volume and/or number of adipose cells, body contouring or tightening skin, skin rejuvenation, wrinkles and/or stretch mark reduction, mole mark removal, tattoo removal, enhanced skin tightening, hair removal, treatment of vascular lesions, acne treatment, sweating reduction and other appearance improving and/or pain relief treatment without contacting the skin. The treatment may optionally be performed simultaneously or consecutively during the same session.

Optical treatment may selectively heat the target biological structure. Optical treatment may remove and/or remodel e.g. adipose tissue. Before/after, with some overlap or simultaneously the magnetic treatment of the target biological structure may induce a muscle contraction within the target biological structure to remodel the adipose tissue by natural adipose tissue catabolism. Adipose tissue catabolism may be caused by apoptosis and/or necrosis of the adipocytes. The muscle contraction caused by induced eddy current may be equivalent to a natural muscle contraction. The adipose tissue may be reduced in natural way. Additionally, the muscle may be toned and/or shaped in a natural way. The treatment results may be significantly improved.

Combined applications of optical waves and magnetic field may be used. The optical treatment may include treatment by optical waves. The magnet treatment may be provided by permanent magnets, electromagnetic devices generating a static magnetic field or preferably by magnetic devices generating time-varying magnetic field. In the preferred application the method may combine treatment by a pulsed magnetic field and optical treatment. The application is not limited by the recited combination so the combined method may include magnetic treatment and any treatment by electromagnetic field such as radiofrequency waves, e.g. microwaves, short waves or long waves.

Various biological structures have a different tolerance to heating/cooling. Hence target biological structures may be remodeled, e.g. adipose cells may be selectively reduced. The cells different from adipose cells such as epidermal cells, are not reduced by the heating/cooling. The selective reduction of adipose cell may be caused by e.g. crystallization within adipose cells. The heating/cooling of the adipose cell may reduce the number and/or volume of adipose cells by lipolysis, apoptosis and/or necrosis.

Although the following exemplary treatment describes applying cold to the patient, the treatment method is not limited to the exemplary application. The method may include heating the patient instead of cooling the patient.

The cooling treatment may be used for treatment of structures in the epidermis, dermis, subcutaneous tissue such as adipose cells, muscle, nerve tissue, etc.), hair follicles, sebaceous glands, sweat glands, nerves, blood vessels, collagen, elastin fibers, acne, hyperhidrosis, wrinkles, fine lines, pores, moles, freckles, port wine stains, and other vascular issues, or the like. Additionally or alternatively, treatments may be used for skin rejuvenation, skin resurfacing or pain relief.

The cooling may be provided by cooling means. The cooling means may be a cooling element and/or a cooling media. The cooling may be provided in a contact, indirect contact and/or non-contact manner. Contact cooling may be provided by a cooling element placed to the proximity of the treated body region, e.g. a thermally conductive material such as metal, gel or ice may be used. Indirect contact may be provided by a flow of cooling media within a layer of flexible and/or rigid material, e.g. cooling media such as glycerol, saline or water solution may be used. The cooling element may include a plurality of passages which the cooling media may flow in. Non-contact cooling may be provided by radiant cooling. Alternatively cooling media may be applied directly on the body region. The cooling media used for non-contact heating/cooling may be preferably a fluid, e.g. a gas or liquid. The gas may be applied in form of a spray, e.g. cold air, $CO_2$ or $N_2$ may be used. The cooling media may be at a predetermined temperature which may be controlled by the device to induce selective treatment of the target biological structure.

The cooling may cool epidermis, dermis and hypodermis such as adipose cells. In an exemplary application the adipose cells may be selectively treated by cooling. Cooling means may be applied to the body region. A reduction of adipose cell may be induced by cooling the adipose cell. Disruption of adipose cells may occur. The cells different from adipose cells may not be reduced by the cooling, i.e. the cells may be unimpeded by irreversible changes such as disruption.

The temperature of the cooling media and/or element may be less than the temperature of the patient's body. The temperature of cooling media may be at least $-196°$ C. The temperature of the cooling media may be in a range of $-90$ to +20° C., preferably in the range of −60 to 10° C., more preferably in the range of −45 to 5° C., most preferably in the range of −20 to 0° C. Alternatively a cooling media may be chilled by the treatment device providing cooling treatment. The cooling media may be preferably ambient air chilled by treatment device. The ambient air may be chilled by a coolant in the treatment device. The coolant may be rigid, e.g. a Peltier device, solid state refrigerator or thermoelectric cooler. Fluid coolants may be gases such as helium, carbon dioxide or sulfur hexafluoride. Two-phase coolants may be halomethanes, haloalkanes, anhydrous ammonia etc. Liquid coolant may be e.g. water with organic antifreeze additives such as ethylene glycol, propylene glycol etc. The coolant temperature may be in a range of −100 to 10° C., preferably in the range of −75 to 5° C., more preferably in the range of −60 to 0° C., most preferably in the range of −50 to −5° C. A flow rate of the cooling media cooling the patient may be regulated by the treatment device, e.g. the flow rate may be in a range of 0.1 to 50 l/s, preferably in the range of 0.5 to 35 l/s, more preferably in the range of 1 to 20 l/s, most preferably in the range of 5 to 15 l/s. The cooling media may be applied to the body region by a hose for directing the cooling media from the treatment device to the body region. The hose may alternatively include at least one nozzle/jet for targeting the cooling media flow onto small body region.

The applicator including at least one cooling element may contact a flat surface up to 1000 cm$^2$, preferably in a range of 1 to 750 cm$^2$, more preferably in the range of 10 to 500 cm$^2$, most preferably 350 cm$^2$. The cooling element may be preferably made of thermally conductive material such as metal or alloy. A shape of cooling element may preferably correspond with a shape of the applicator. Each cooling element may preferably include a contact plate for contacting the patient's skin.

The cooling element may be a Peltier device. Alternatively the cooling element may be passively cooled by coolant flowing inside the cooling element. Alternatively the cooling element may include an inner tubing for directing a coolant within the coolant inside the cooling element in order to cool the cooling element. The coolant may be a phase change medium or precooled coolant of specific heat capacity. The specific heat capacity may be preferably high.

The temperature of the cooling element may be preferably in the range of 40 to −40° C., more preferably in the range of 20 to −20° C., even more preferably in the range of 10 to −15° C. or in the range of 5 to −10° C. The cooling element may have cooling power in a range of up to 100 W, preferably in a range of 1 to 75 W, more preferably in a range of 5 to 50 W, most preferably in the range of 10 to 35 W.

According to another embodiment an applicator including the magnetic field generating device may by cooled by a cooling media. A temperature of the cooling media may be sufficient to cool down the casing of the applicator in order to be a cooling means and to cool the skin.

A cryoprotectant may be applied to the skin prior to cooling the skin in order to prevent irreversible damages to epidermis by applying the cooling to the body region.

The cryoprotectant may have a freezing temperature in a range of −40 to 0° C. The freezing temperature should be suitable with the temperature of the cooling element. The cryoprotectant may be applied onto epidermis and/or the cooling element. Alternatively the cryoprotectant may be on a mesh or fabric and it may be placed between the cooling element/media and patient's skin. The cryoprotectant may reduce the freezing temperature of body fluids below 0° C., e.g. to −2, −5, −10 or −15° C. The cryoprotectant may be a paste, gel, hydrogel or liquid. The cryoprotectant should be thermoconductive and biocompatible. Examples of cryoprotectants are well known in state of the art.

A temperature of the adipose cells may be above a freezing point of water to prevent a reduction of cells including water. The temperature of the hypodermis, e.g. adipose cells, may be preferably in the range of 37 to −10° C., more preferably in the range of 20 to −4° C., even more preferably in the range of 15 to −2° C. or around 4° C. The temperature of epidermis may be at least −40, −20, −10, 15, 20, 35° C., more preferably the temperature of epidermis may be in the range of around 5 to −5° C. A temperature of dermis may be higher than temperature of epidermis. The temperature of dermis may be in a range of −15 to 20° C., preferably in the range of −10 to 15° C., more preferably in the range of −8 to 10° C., even more preferably in the range of −4 to 5° C., most preferably in the range of −2 to 3° C. The term around may be interpreted to mean in the range of 10% of the particular value.

The temperature of adipose cells may vary during the treatment. The temperature of the adipose cells may oscillate around a predetermined temperature. The temperature of the adipose cells may also follow a temperature profile in a predefined temperature range. The temperature and/or the temperature range may be adjusted following the patient's needs.

Alternatively the adipose cells may be heated prior, during and/or after cooling. The term "heat prior" refers to preheating the adipose cells before cooling treatment. The term "heat during" refers to cyclically changing periods of cooling and heating the adipose cells during the treatment. The treatment may also include passive periods between heating and/or cooling. The term "passive period" refers to applying neither heating nor cooling. The term "heat after" refers to applying heat after the cooling treatment. The periods of heating/cooling and/or passive periods may be adjusted following by the patient's need.

The cooling may be applied for at least 10 seconds. Time duration of cooling the body region may be in the range of 1 to 240 minutes, more preferably in the range of 5 to 120 minutes, even more preferably 10 to 60 minutes, most preferably in the range of 15 to 30 minutes.

The cooling element and/or media may be applied continuously and/or in pulses. Continuous application may be used for a cooling element and/or media at a temperature above 0° C. Pulsed mode may be used for application of fluids below 0° C. The cooling may be provided cyclically for short periods in order of milliseconds, e.g. $N_2$ may be applied cyclically to prevent damage to epidermis/dermis. The cooling element and/or media may be applied preferably non-invasively, e.g. by topical application. Alternatively the cooling element and/or media may be applied subcutaneously, e.g. injected.

The cooling element may correspond with the body region. The cooling element may be adjustable in shape to fit the body region. The cooling element may be made of flexible material to be modified in shape to follow the shape and/or contour of the body region. A fitting of the cooling element may provide homogenous treatment and/or temperature distribution. Further the heat transfer may be optimized at the contacted surface. Alternatively an applicator may apply a negative pressure to the treated body region in order to provide contact between the applicator including the cooling element and patient's skin.

According to an exemplary application the treated body region may be cleaned prior the cooling treatment. The cooling treatment may be applied to the patient by positioning the applicator including the cooling element to direct or indirect contact with the patient. The applicator may preferably include a handle for user-friendly maneuvering and positioning the applicator onto the body region. Static position of the applicator with respect to the patient may be provided by fixing the applicator to the patient by a positioning member such as length adjustable belt or by negative pressure. The cooling treatment may start and heat transfer between hypodermis and the cooling element may start. After the treatment the treated body region may be preferably treated by mechanical treatment such as manual massage.

According to another exemplary application the applicator delivering the cooling media may be placed proximate to the treated body region. The cooling media may be applied to the body region. The applicator may be preferably moved over the treated body region in order to prevent thermal damages to the skin. During the treatment the cooling treatment parameters may be adjusted manually or automatically. The cooling treatment parameters may be cooling media temperature, cooling media flow or distance of the applicator from the skin of the patient.

A treatment may induce a thermal gradient in the body region, i.e. the shallow layer of the skin such as epidermis and/or dermis may have a lower temperature than the deeper layer such as adipose tissue. The effect of cooling may be improved by limiting and/or eliminating dermal blood flow. The dermal blood flow may be limited by applying vasoconstrictive medicine, preferably topically administered.

A thermal gradient may be also a temperature difference between the cooling element and/or media and biological structure such as hypodermis. A temperature difference $\Delta T1$ may be between cooling element and the hypodermis. A temperature difference $\Delta T2$ may be between the cooling media and the hypodermis.

Absolute values of the temperature difference $\Delta T1$ may be in the range of 0 to 70° C., preferably in the range of 2 to 50° C., even more preferably in the range of 5 to 25° C., most preferably in the range of 10 to 15° C.

Absolute values of temperature difference $\Delta T2$ may be in a range of 0 to 200° C., preferably in the range of 5 to 100° C., more preferably in the range of 10 to 75° C., most preferably in the range of 20 to 40° C.

The cooling may cool down the hypodermis up to 15 cm, preferably in a range of 0.01 to 10 cm, more preferably in the range of 0.05 to 7.5 cm, most preferably in the range of 0.1 to 5 cm. A volume of frozen tissue may be up to 2500 $cm^3$, more preferably in a range of 10 to 1500 $cm^3$, more preferably in the range of 25 to 1000 $cm^3$, most preferably in the range of 50 to 500 $cm^3$.

The device may comprise one or more sensors providing feedback information to control unit, user interface and/or to an individual controlling system. Based on evaluated feedback information, cooling treatment parameters may be adjusted by control unit, by a user and/or by any controlling mechanism. A sensor may be located in a heat exchanger, cooling element and/or in the applicator. Sensors in the device may measure: pressure under the applicator, temperature, viscosity of heat transmitter, flow of the heat transmitter, impedance, capacity, permittivity, conductivity, susceptibility of any part of the device and/or patient's body, sensors analyzing backscattered signal, infrared radiated spectrum and its intensity, heat capacity, voltage, electric current, phase shift of delivered and backscattered signal of treatment energy, pulse of the patient and any other biological, biochemical and/or physical parameter e.g.: skin tension, muscle tension, level of muscle contraction, amount of perspiration etc.

Temperature of the soft tissue may be measured by a sensor directly evaluating temperature as a physical quantity (e.g. thermometer, thermal imager, etc.) Another method to evaluate temperature may be by measuring a different physical quantity other than temperature, wherein the physical quantity is thermally dependent (e.g. by measuring impedance of the soft tissue beneath the epidermis and counting soft tissue temperature based on a correlation function that describes such soft tissue dependence of impedance on temperature). Indirect methods of measuring soft tissue temperature may be beneficial to evaluate noninvasively temperature of the soft tissue under the epidermis, dermis and/or hypodermis.

The above described sensors may be used for feedback preventing occurrence of frostbites. In order to prevent occurrence of the frostbites cryoprotectants may be used, cooling temperature and/or treatment time may be adjusted. Alternatively a distance between skin and the cooling element may be adjusted. Cooling media flow rate or a distance between the skin and the applicator directing the cooling media to the body region may be adjusted as well.

The dermal blood flow may also be limited and/or eliminated by applying a pressure. The pressure greater than systolic blood pressure may be used for pushing the blood out of the dermal and/or subcutaneous veins. The deeper adipose cells may be cooled and/or the cooling of the adipose cells to the temperature sufficient to reducing the adipose cells may be reached in shorter time period. Furthermore appropriate contact of the cooling element may be provided by the pressure in case of contact treatment.

The treatment effect may also be enhanced by applying negative pressure to the skin below the applicator, e.g. a convex applicator including the cooling element may be used. The skin may be pulled towards the inner surface of the cooling element. Hence the contact may be enabled by applying negative pressure. The skin pulled inside the applicator by the negative pressure may be cooled by the cooling element. Alternatively, the folded tissue may be pinched by two or more cooling elements and the cooling may be applied to the tissue, particularly to adipose cells. Further the skin may be stretched and a thickness of the skin may decrease. Skin thickness decrease may promote improved heat transfer to/from adipose cells. Alternatively the negative pressure may be applied cyclically, i.e. in pulsed mode. The cyclically applied negative pressure may pulse with a repetition rate of pulses in a range of 0.1 to 10 Hz, more preferably in the range of 0.5 to 7 Hz, most preferably in the range of 1 to 5 Hz. The cyclically applied negative pressure may promote lymph and/or blood circulation within the treated body region. Hence the cyclic negative pressure may be preferentially applied during last few seconds or minutes of the treatment.

The cooling may be applied with application mechanical treatment such as acoustic, ultrasound, and/or shockwave treatment to enable more homogenous treatment effect. The adipose cells reduction may also be promoted by physical movement of the body region by e.g. massaging, or vibrations. The pressure applied to the body region may vary to improve the results.

An apoptotic index may increase after cooling the body region. The apoptotic index refers to a percentage of apoptotic cells in specimen. The apoptotic index may increase due to cooling up to ten times greater value compared with the value prior the cooling.

Based on the apoptotic index a treatment combining various methods may be designed as a tailor-made solution following the patient's need. The cooling may be applied to the body region of the patient prior, during and/or after applying a magnetic field to the patient. Cooling may be applied to the patient by one treatment device, i.e. the treatment device may apply to the patient the cooling and the time-varying magnetic field by at least one applicator. Alternatively the cooling may be provided by one applicator and the time-varying magnetic field may be applied by another applicator.

A pain relieving medicament may be provided during the treatment if the patient is more sensitive to decreased temperature. A topical application may be preferred. The pain relief effect may be provided by a magnetic field of repetition rate at least 100 Hz, more preferably 120 Hz, even more preferably at least 140 Hz or at least 180 Hz. The pain relieving effect may be provided before, during or after the treatment.

Cooling the body region prior to applying the magnetic field may influence a metabolism of adipose cells. Alternatively, the cooling of the adipose cells may induce apoptosis, lipolysis, autophagy and/or disruption of the adipose cells. A release of FFA from adipose cells may induce ER stress as recited above. The application of the magnetic field may cause at least muscle contraction reducing the adipose cells. Furthermore the released FFA from adipose cells influenced by cooling may be used as energy source for muscle work. Hence the cooling may be followed by treating a patient by magnetic field inducing at least muscle contraction. Due to the combined effect of cooling and magnetic treatment the adipose cells may be reduced in number and/or volume. Moreover the muscles may be shaped, tightened, strengthened and/or the volume of the muscle may increase. Additionally, the cellulite appearance may be reduced due to muscle work.

The magnetic treatment may provide a massage effect. Hence blood and/or lymph flow may be improved. Additionally cooled tissue may be relaxed.

Alternatively at least one cooling treatment may cause significant adipose cells reduction. This cooling treatment or a plurality of cooling treatments may be followed by at least one treatment by magnetic field in order to treat the muscle and/or reduce the adipose cells. The muscle may obtain tone, strength and/or volume. The at least one treatment by magnetic field may follow the at least one cooling treatment immediately or after a time period lasting at least 0.01, 0.05, 0.1, 0.5, 1 or up to 10 hours, more preferably at least one day, even more preferably around one week or up to one month. The period between the cooling treatment may be up to 6 months, preferably 1 day to 3 months, more preferably 1 week to 2 months, most preferably 2 to 6 weeks.

The combined magnetic treatment may be applied immediately after an auxiliary treatment method, more preferably around 0.01 to 24 hours after an auxiliary treatment, e.g. 1, 2, 8 or 20 hours. The combined treatment may be applied periodically. Alternatively, the an auxiliary treatment method and/or magnetic field may be applied separately, e.g. treatments may alternate in appropriate periods. The period between two treatments may last from 12 hours to 1 month or longer, more preferably from 1 day to 2 weeks, most preferably from 3 days to 1 week.

In an exemplary application of the treatment method a patient's body region may be cooled by a cooling element for e.g. at least 20 minutes up to 1 hour. After stopping the cooling the body region may be treated by magnetic field for e.g. 15 to 45 minutes.

In another exemplary application of combined treatment method the body region may be treated by cooling. After cooling a multiple treatments by time-varying magnetic field may follow. Alternatively cooling may be repeated after a period of 2 to 6 weeks.

Cooling the body region may be applied simultaneously while the body region is treated by magnetic field within one treatment.

The cooling may be provided to the patient while the patient is being treated by magnetic field.

Alternatively, cooling may alternate with treatment by magnetic field, i.e. the magnetic field is applied when cooling is not provided to the patient or vice versa. Periods of alternating cooling and magnetic treatment may vary.

The magnetic field may be preferably applied in burst mode. Each burst contains train of magnetic impulses and a period of no magnetic treatment. The train may include a plurality of magnetic impulses. A number of magnetic impulses may vary in the range of at least 1 to 10000 impulses, more preferably in the range of at least 10 to 1000 impulses. The time duration of the train and/or the period of no magnetic treatment may vary in order of milliseconds to order of seconds, e.g. in the range of 100 milliseconds to 100 seconds, more preferably in the range of 1 to 30 seconds, most preferably in the range of 5 to 15 seconds.

In one exemplary application the body region may be cooled for a period of e.g. at least 5 minutes. After stopping the cooling the body region may be treated by a magnetic field for a period of e.g. at least 5 minutes. After stopping the magnetic treatment the body region may be cooled.

The cooling may also be applied after magnetic treatment. The treatment by magnetic field may provide stimulation, pain relief and/or a myorelaxation effect for the treated body area before cooling. The cooling applied with pressure may be better accepted by the adipose tissue when the muscle below the adipose cells is relaxed. Alternatively the magnetic treatment may provide a temporary pain relief effect hence a patient suffering from a lower pain threshold, e.g. cool sensitivity, may be treated.

Further the adipose cells within the body region treated by the time-varying magnetic field may tend to be more prone to cooling induced apoptosis.

In an exemplary application the body region may be treated by a magnetic field for a period of e.g. at least 15, 20 or 30 minutes. After stopping the magnetic treatment the body region may be cooled.

The cooling may be applied immediately after magnetic treatment, more preferably around 1 to 24 hours after magnetic treatment, e.g. 1, 2, 8 or 20 hours after magnetic treatment. The combined treatment may be applied periodically.

In an exemplary application of the treatment method a patient's body region may be treated by magnetic field for e.g. at least 20 minutes up to 1 hour. After stopping the magnetic treatment the body region may be treated by cooling for e.g. 15 to 45 minutes.

In the previously described exemplary treatment methods the cooling of the patient may be replaced by heating the patient.

Figure 11A:
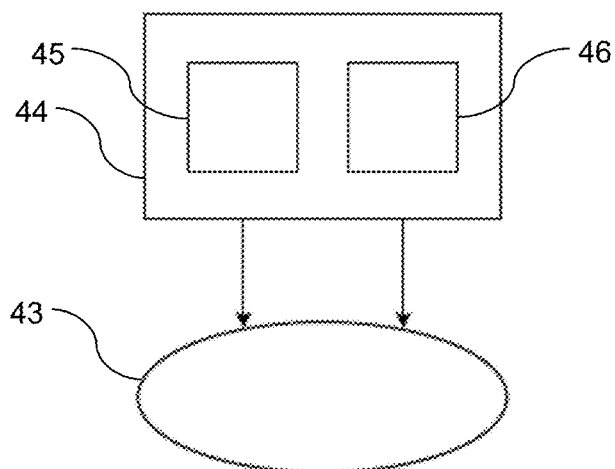
FIGS. 11a and 11b illustrate diagrams of a treatment device and/or an applicator providing magnetic and/or thermal treatment.
Figure 11B:
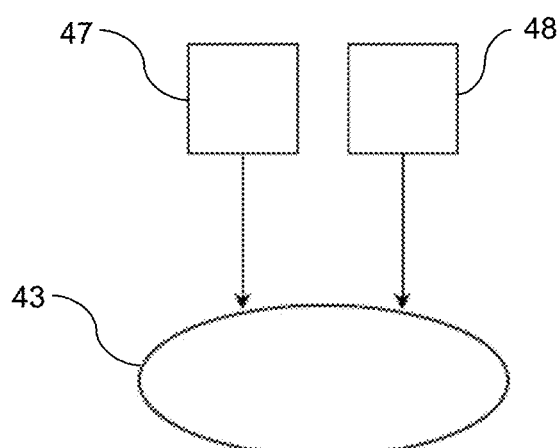

FIGS. 11a and 11b illustrate a device/devices providing the combined treatment to the body region of the patient 43.

FIG. 11a illustrates a treatment device 44 including a connection to power source, a magnetic field generating device 45 and means for providing heating/cooling 46, e.g. RF source or cooling element. In an alternative embodiment the treatment device may include at least one magnetic field generating device which is also able to provide radiofrequency waves.

FIG. 11b illustrates alternative treatment applied to the patient 43 by two separate treatment devices, i.e. by a device providing magnetic treatment 47 and a device providing heating/cooling 48.

All the recited combined treatment methods may be provided by at least one applicator. The applicator may provide cooling and magnetic treatment. Alternatively one applicator may provide cooling and second applicator may provide magnetic treatment. Alternatively cooling and magnetic treatment may be provided by separate treatment devices, i.e. one treatment device for cooling the patient and second device for applying the time-varying magnetic field to the patient. Cooling and time-varying magnetic field may be applied to the patient by one applicator independently, i.e. simultaneously or prior/after each other.

The target structure may be treated by combined methods which may be used for remodeling the adipose tissue, body shaping and/or contouring, muscle toning, skin tightening, skin rejuvenation, wrinkle removing, reducing stretchmarks, breast lifting, lip enhancement or treatment of cellulite in general by application of electromagnetic radiation to target structure to selectively heat the target tissue to remove and/or remodel adipose tissue from the target tissue. The second approach is to transmit a magnetic treatment to the target structure, inducing at least muscle contraction within the target structure to remodel the adipose tissue by natural adipose tissue catabolism. Adipose tissue catabolism may be caused by apoptosis or necrosis of the adipocytes. The muscle contraction caused by induced eddy current is the same as a natural contraction. The adipose tissue may be reduced in natural way. Additionally, the muscle may be shredded in a natural way. Therefore the effect resulting in body shaping and/or contouring may be significantly improved.

The combination of the recited method may improve currently used applications in various aspects and the effect of the treatments may be significantly enhanced. The application of a radiofrequency electromagnetic field may be combined with application of a magnetic field applied before, simultaneously or after the radiofrequency treatment. The application of a magnetic field may induce many benefits for radiofrequency treatment, such as applications inducing at least muscle contraction, myorelaxation effect or analgesic effect. The perfusion or metabolism may be improved as well.

The at least muscle contraction may induce enhanced effects on adipose tissue reduction by catabolism of the adipose tissue and burning energy from adipose tissue. The total adipose tissue reduction effect may be enhanced by radiofrequency treatment.

Additionally, the at least muscle contraction may improve a blood flow and/or perfusion in the treated body region. The improved blood flow may be caused by activation of muscle pump and/or by the muscle necessity of more oxygen due to the at least partial contraction. The blood flow may increase rapidly and it may last temporarily, preferably up to 1 hour, more preferably up to 45 minutes, most preferably up to 30 minutes. Due to increased blood flow and/or local perfusion, the risk of overheated muscle may be limited or even eliminated. Further the homogeneity of the thermal field induced by thermal effect of radiofrequency treatment may be significantly enhanced and/or the temperatures may be well-balanced/compensated in the target body region. Still another benefit may be prevention of creation any hot spot caused by steep thermal gradient.

Due to improved blood flow, perfusion and/or lymph flow the metabolism may be improved. Additionally, the effect of radiofrequency treatment may be enhanced by improved metabolism, e.g. cellulite treatment, body shaping and/or contouring, skin tightening or skin rejuvenation. Further benefit may be reducing or eliminating the risk of panniculitis or local skin inflammation since any clustering of the treated adipocytes may be prevented by the improved metabolism. The improved blood and/or lymph flow may contribute the removing of the adipocytes. The removing of the adipocytes may be promoted by higher number of cells phagocytosing the adipocytes as well. Synergic effects of magnetic and RF treatment may significantly improve metabolism. Therefore the possibility of adverse event occurrence may be limited and treatment results induced by the present invention may be reached in shorter time period.

Further the at least muscle contraction may improve the movement of lymphatic vessel and the lymph flow may be improved.

In the preferred application the RF and/or magnetic field may be modulated. In the most preferred application both treatments are modulated. The magnetic treatment may be modulated in the magnetic flux density domain, repetition rate domain, or impulse duration domain, to provide different treatment effects and to prevent adaptation of the target biological structure. The radiofrequency treatment may be modulated in the frequency domain, intensity domain and/or time domain to reach the most complexity and/or efficiency of the target treated biological structure. The modulation in the time domain may be changing the active and passive periods of treatment, e.g. the radiofrequency treatment may include period with no stimulation, i.e. the radiofrequency treatment may be not continual but the treatment may be provided in pulses. The periods of no stimulation may vary and may be adjusted by the operator. Due to modulation during the treatment, different target biological structures may be treated in the different depth.

The application may be contact or in the preferred application the treatment may be applied contactless. Contactless application may avoid all biocompatibility factors which may occur during contact treatment. In the most preferred application the treatment may be provided by self-operated device. Hence the applicator and/or magnetic field generating device needn't to be guided by the operator. The applicator may be positioned on the patient in static position or it may dynamically move and provide therapy in predetermined pattern. The device, the applicator and/or the magnetic field generating device needn't to be operated by the operator or needn't be under continual operator's surveillance for at least 5, 10, 30, 60, 240 seconds or longer with no risk to the patient. The applicator may be fixed in sufficient distance from the patient's skin enabling the safe treatment for the patient. Self-operated treatment may be provided by a hand-held applicator or the applicator may be fixed to stand-alone device. The self-operated treatment may be also enabled using various types of sensors in communication with the device for monitoring the treatment and/or the patient. The at least one sensor may be e.g. reactive sensor, electrochemical sensor, biosensor, biochemical sensor, temperature sensor, sorption sensor, pH sensor, voltage sensor, sensor for measuring distance of applicator from the patient surface and/or from the treated area, position sensor, motion detector, photo sensor, camera, sound detector, current sensor, sensor for measuring of specific human/animal tissue and/or any suitable sensors measuring biological parameters and/or combination thereof such as sensor for measuring dermal tensile forces, sensor for measuring the activity of the muscle, muscle contraction forces, tissue impedance or skin elasticity.

Further the homogeneity of the treatment may be improved by several approaches. A first approach may be represented by a moveable applicator providing the dynamic treatment to a large target area. The dynamic treatment may improve the homogeneity of applied treatment energy and additionally due to large area the effect is uniform and/or well balanced. Static positioning of the applicator may be used as well. Another approach of improving homogeneity may be represented by using a bolus. The bolus may provide improved transmittance of the electromagnetic energy to the treated biological structures. Additionally, the bolus may prevent occurrence of hot spots within the treated area; the bolus may provide constant temperature to the target treated surface area; or the bolus may increase the homogeneity of the radiofrequency waves application by providing a homogenous medium for electromagnetic waves propagation not being influenced by the interface of the target treated area and an air. The bolus may profile the electromagnetic field to enhance the effect of the treatment. In still another approach an air gap may be between the applicator and the patient.

The treatment by magnetic and/or electromagnetic field may be in continuous or discrete mode. In one application the magnetic treatment may be applied in continual mode with no pauses and the electromagnetic treatment may be applied in pulsed mode to provide improved adipose tissue reduction caused by natural process and by the increased temperature. In another application the electromagnetic treatment may be applied continuously with no pauses and the magnetic treatment may be applied in pulsed mode to provide improved thermal reduction of adipose tissue and by improved metabolism due to improved blood flow. Both modes may be combined in various treatment sequences.

The application of electromagnetic waves may lead to heating of the tissue. Energy flux provided by radiofrequency waves may be in the range of 0.001 W/cm$^2$ to 1500 W/cm$^2$, more preferably in the range of 0.01 W/cm$^2$ to 1000 W/cm$^2$, most preferably in the range of 0.5 W/cm$^2$ to 500 W/cm$^2$.

The sum of energy flux density of the radiofrequency waves and the optical waves applied to the patient during the therapy, where the therapy means simultaneous, successive or overlap treatment or treatments, may last up to 120 minutes, more preferably up to 60 minutes, most preferably up to 30 minutes, is in the range of 0.03 mW/mm$^2$ and 1.2 W/mm$^2$, more preferably in the range of 0.05 mW/mm$^2$ and 0.9 W/mm$^2$, most preferably in the range of 0.01 mW/mm$^2$ and 0.6 W/mm$^2$. The energy flux density of optical waves constitutes at least 1%, more preferably at least 3% and most preferably at least 5% of the sum of energy flux density.

In the preferred application the treatment may be started at the moment when the target biological structure reaches the predetermined temperature. The temperature in the target tissue may be up to 80° C., more preferably in the range of 37 to 60° C., even more preferably in the range of 40 to 45° C. The temperature may be adjusted based on the intended use, e.g. adipose tissue reduction, collagen production or muscle contraction. In an alternative application the intended use may be coagulation and/or ablation. The temperature in the target biological structure may be measured by invasive method, e.g. using an invasive probe; or by contact method, e.g. using thermocouple sensor; or by contactless method, e.g. using infrared sensor or camera.

The temperature of the target biological structure may be determined by a mathematic method. The sensor for measuring the temperature in the target biological structure may be attached to the applicator.

A benefit of the application of magnetic treatment and electromagnetic treatment may be causing an analgesic effect of the application and providing a possibility of treating a patient with higher sensitivity for thermal effects induced by electromagnetic treatment, i.e. patients with any predisposition inducing increased thermal sensitivity. The analgesic effect may be induced by magnetic treatment by suitable repetition rates and it may be induced immediately during the magnetic treatment. The analgesic effect may last up to several hours after magnetic treatment. The magnetic flux density of the magnetic treatment may preferably reach at least motor-threshold intensity inducing at least muscle contraction therefore the homogeneity of the thermal field may be significantly enhanced.

Another benefit of application the magnetic treatment may be causing a myorelaxation effect. The magnetic treatment may be applied on spastic muscle structures to relieve the hypertonus of the muscle and improving the blood and/or lymph flow. Therefore relieving the hypertoned muscle may contribute to the analgesic effect and contribute to the acceptability of the treatment by the patient.

The blood and/or lymph flow may be limited in the spastic muscles and the metabolism may be limited as well, meaning that the risk of clustering the treated target structures may be higher and possible adverse events may occur. The recited risks may be eliminated by the used of magnetic treatment.

In one aspect of the invention, the treatment by magnetic field may be applied to the target structure before the radiofrequency treatment to prepare the target structure for following treatment by radiofrequency field. The effect of magnetic treatment may be to induce at least muscle contraction or to treat a muscle structure to increase a muscular tonus of the target structure. Both effects may provide a massage effect for the structure within the proximity of the target structure hence the blood and/or lymph circulation may be improved to promote local metabolism. The temperature may be locally increased by the improved blood flow and the target structure may accept the following radiofrequency treatment at significantly higher quality. Additionally, the collagen and/or elastin fibers may be remodeled or restored and/or its neogenesis may be improved to provide a younger, smoother, firmer and enhanced skin appearance.

Additionally, previous application may improve acceptability of the electromagnetic field by increasing the temperature of the skin and the transmittance of the electromagnetic field may be improved due to less value of skin impedance. Further the radiofrequency may penetrate deeper target structures relative to treatment without a preceding magnetic treatment of the target structure and/or area.

Another benefit may be releasing the adipose tissue in the muscle by muscle contraction and/or by temperature increase causing better liquidity of adipose tissue. Still another benefit of the at least muscle contraction may be mechanical breaking large adipose tissue bulks into smaller bulks which may be easier metabolized and/or the smaller adipose tissue bulks may be removed faster by the lymphatic and/or blood flow. Due to improved metabolism and/or circulation the cellulite may be treated in a short time and the visual effect on skin appearance may be significantly enhanced.

In another aspect of the invention, the treatment by magnetic field may be applied to the target structure simultaneously with the radiofrequency treatment to improve effects of the electromagnetic treatment inducing heat in the target structure.

The simultaneous application of magnetic treatment and radiofrequency treatment may be in two modes: a first mode may generate the magnetic impulses while radiofrequency treatment is active or another mode may generate radiofrequency treatment while the magnetic treatment is not in an active treatment period, i.e. the period of magnetic treatment and radiofrequency treatment alternates. Both modes amplify the resulting effect of the treatment. Therefore the results may be achieved in significantly shorter time than the same results achieved by separate applications of the radio frequency and magnetic treatments.

The simultaneous method of magnetic treatment and radiofrequency treatment of the target tissue may increase the peak magnetic component of the entire treatment resulting in improved heating of the target structure including containing higher water volume, e.g. skin. Due to increased temperature of skin, the production and/or remodeling of collagen and/or elastin fibers may be improved and the skin may be provided with a younger, smoother, firmer and enhanced appearance. The effect of overheating the muscle may be reduced by the improved blood flow.

In still another aspect of the invention, the treatment by magnetic field may be applied to the target structure after the treatment by electromagnetic field to enhance and/or contribute to the effects of radiofrequency treatment by influencing the target structure by magnetic field.

The magnetic field may treat the target structure to cause at least muscle contraction proximate to the target structure to improve blood flow and provide homogenous temperature distribution at high quality after creating a temperature distribution at lower quality by radiofrequency treatment.

All of the methods may be provided by the above recited technical solutions. The above mentioned methods may be used separately or in any combination.

The method may cause the circumferential reduction i.e. a reduction of the size of the treated body region. The method may be mostly indicated for the regions with cellulite, especially for buttock, saddlebag, love handle, abdomen, hip, thigh or arm. However, the indication is not limited to the mentioned regions and the method may be used for treatment of any other body region.

The at least one applicator may include at least one magnetic field generating device. The plurality of magnetic field generating devices may be positioned in isolated locations of the at least one applicator. Alternatively, the magnetic field generating devices may be positioned next to each other, in an array or matrix, in a pattern or in randomized locations of the at least applicator.

The magnetic field generating devices may be positioned and/or moved in the at least one applicator in one plane; in at least two mutually tilted planes defined by a convex or concave angle, or perpendicular to each other; or in at least two parallel planes with the at least one magnetic field generating device in each parallel plane. The movement of the at least one magnetic field generating device may be translational and/or rotational, constant or accelerated. The movement may follow a predetermined, random or predefined trajectory, such as a pattern, array or matrix. The movement of the at least one applicator may be handled in similar manner as the movement of the at least one magnetic field generating device. The angles of the planes and/or the movement of the at least one magnetic field generating device may be adjusted by an operator following the patient's needs. The positioning may be provided by mechanical holder, enabling tilting, distancing and positioning magnetic field generating device in various planes. In an alternative embodiment the patient may be positioned in the intersection of the magnetic fields generated by the plurality of magnetic field generating devices. In the preferred application the at least one applicator may be movable and the movement may be circular.

The plurality of magnetic field generating devices may be positioned within one applicator having form of mechanical holder. The shape of the applicator having form of mechanical holder may be adjustable, e.g. the applicator may include at least one moveable part. In a preferred embodiment the applicator having form of mechanical holder may provide spatial arrangement of the energy delivery elements in one axis, two axes or three axes and/or provide tilting and/or rotation. The applicator having form of mechanical holder may provide fixation of the at least one magnetic field generating device in one position. The moveable parts may be connected by sliding mechanism and/or by a joint mechanism. An exemplary embodiment of such an applicator may be found in U.S. Pat. No. 9,468,774, incorporated herein by reference. The applicator may be adjustable following the body region and/or biological structure.

The present methods may also induce muscle contraction to reduce effect of skin laxity. Skin laxity may be caused by e.g. aging process or increasing number and/or volume of adipose cells which pulls down the skin by gravity, rapid weight loss or skin stretching during the pregnancy. The muscles may be treated by the induced electric current to contract. Repetitive contractions may cause the muscles to obtain the tonus and flexibility. Therefore the skin appearance may be enhanced by treating the flabby muscles. The effect of skin tightening may be achieved. The method also may promote the collagen and elastin fibers in the layers subtending the epidermis hence the skin may obtain enhanced visual appearance. The method may be widely applied but not limited to application to the regions of neck, breasts, arms or abdomen. The method may provide the smoother and younger appearance of the skin to the patient.

Similar methods of the muscle structure treatment by time-varying magnetic field for inducing the at least muscle contraction may be used for treatment of wrinkles as well. Wrinkles are results of extrinsic and intrinsic factors. Nowadays, wrinkles are considered to be negative effect of natural aging process which decreases the production of collagen and elastin fibers and weakens the skin which becomes thinner. As the muscle treatment by the magnetic flux density may induce at least muscle contraction, the collagen and elastin fibers neogenesis may be improved. Additionally, the muscles subtending the treated region may be toned and the skin may obtain a younger and enhanced visual appearance. Therefore, the effect of skin tightening may be achieved.

Wrinkles may be prevented or reduced by practicing facial exercises which may cause a massage effect to the facial tissues, improving blood and lymph circulation. Additionally, the facial muscles may be relaxed and toned after the exercise. A similar effect as facial exercise may be achieved by non-invasive and/or contactless method of treating the facial muscles by magnetic flux density. Further additional advantage of the present method may be the improvement of restoration of the collagen and elastin fibers, more effective toning and strengthening of the facial muscles.

The present methods may improve the neogenesis and remodeling of collagen fibers in the lips to reach a full, plump and firmer appearance. The magnetic flux density may be applied to the lips by an applicator. Therefore the lips may become fuller and firmer without any need of invasive method such as injection of the synthetic fillers, permanent makeup or the facial implants. The present method may promote the remodeling and/or neogenesis of collagen fibers in a natural way. Additionally, the collagen is natural substance of the human body which may provide the elasticity to the structure.

The present methods may be used for enhancing the visual appearance of breasts. Cooper's ligament may be treated, improved and/or firmed by the at least muscle contraction. The treatment may induce the elevation of the breast tissue. Additionally, the breast tissue may be treated to be modified in a shape, wherein the shape includes the size and/or the contour of the breast tissue. Therefore the visual appearance may be enhanced and breasts may be more attractive for the patient. The present method may be a non-invasive alternative for current aesthetic surgery method for the treatment of sagging breast tissue. The present method may provide a patient a method of breast visual appearance enhancement without surgery. Therefore the method lacks post-surgery complications such as scars, postoperative pain or long recovery period. Various treatment protocols may be used.

Following the recited methods the treatment may be but is not limited to continuous, pulsed, randomized or burst. The impulse may be but not limited to monophasic, polyphasic, biphasic and/or static magnetic field. In the preferred application the magnetic impulse may be in biphasic regime, i.e. it is consisted of two phases, preferably positive and negative.

Repetition rate and/or magnetic flux density may vary during the treatment protocol. Further the treatment may include several periods of different repetition rates, therefore the modulation may be in repetition rate domain. The treatment may include several periods of different magnetic flux densities, therefore the modulation may be in magnetic flux density domain. Alternatively the treatment may include different impulse durations, therefore the modulation may be in impulse duration domain. In yet another approach the treatment may be modulated by any combinations thereof.

In one embodiment the repetition rate may be modulated during one treatment protocol. In one example the train may refer to a plurality of pulses wherein the at least two following pulses in the train are applied to the patient with the first repetition rate and wherein the train includes at least two different following pulses applied to the patient with the second repetition rate. Wherein the first repetition rate may be in the range of 10 to 100 Hz or 11 to 80 Hz or 12 to 50 Hz and wherein the second repetition rate may be in the range 0.1 to 30 Hz or 0.5 to 25 Hz or 1 to 20 Hz or 1 of 12 Hz. According to the same example the pulses of the first and the second repetition rates may be applied in order to provide incomplete tetanus contraction of the treated muscle or complete tetanus contraction of treated muscle. According to the same example the pulses of the first repetition rate may be applied in order to provide incomplete tetanus contraction of the treated muscle or complete tetanus contraction of treated muscle. In still another example the train may refer to a plurality of pulses including more than two different repetition rates.

Various envelopes and/or waveforms, e.g. pulse, sinusoidal, rectangular, square, triangular, saw-tooth, trapezoidal, exponential etc. for the purpose of muscle treatment may also be used, and are not limited to recited shapes.

The values of magnetic flux density and repetition rate are cited in several preferred applications since the perception of the treatment is subjective. Nevertheless, the magnetic flux density and repetition rates are not limited by the recited values. A person skilled in the physical therapy is able to repeat and apply the treatment methods adjusting the magnetic flux density and/or repetition rate following the patient's sensitivity or needs.

The present method is not limited to be used independently. For enhancing the results the methods may be used in combination with other auxiliary treatment method.

A combined treatment may improve the blood flow, create micro-disruptions of treated tissue such as adipose cells, and/or create movement, rotation or polarization of particles by induced current and/or magnetic field which increase the temperature of treated tissue. The combined treatment may result in increased cell membrane permeability resulting in increased liquefying of clusters of adipose cells and/or lipolysis. The combined treatment highly reduces the risk side effect associated with currently used treatment methods such as occurrence of e.g. panniculitis or swelling.

An exemplary application of the combined treatment method may use application of cold, mechanical treatment, heating and magnetic field. Such application may be cooling the body region and maintaining the adipose cells to the temperature in the range of 15 to −2° C. Cooling may cool the adipose cells and the adipose cells may be at least partially damaged. Further the mechanical treatment may be applied to the body region to break large clusters to smaller clusters of adipose cells. Further the body region may be heated by e.g. radiofrequency treatment. The smaller clusters of adipose cells may be heated by the radiofrequency waves more homogenously compared to heating of the large adipose cells cluster. Finally the time-varying magnetic field may be applied to the body region. The induced muscle contraction may improve blood and/or lymph flow. The treated adipose cells may be better metabolized and/or removed from the treated body region. Further the muscle contraction may metabolize released FFA as a primary energy source.

Another exemplary application may use heating the adipose cells by radiofrequency waves. Alternatively the adipose cells may be heated by ultrasound waves or light. Additionally, the cavitation may induce disruption of the adipose cells. Further the magnetic treatment may cause the muscle contraction increasing blood and/or lymph flow. The muscle contraction may metabolize released FFA as a primary energy source. Further the mechanical treatment may provide the massage effect for the treated body region for better regeneration and/or faster removing lactate and/or metabolic products. Alternatively the exemplary application may include cooling the body region after applying mechanical treatment to improve reducing of the adipose cells.

Still another exemplary application may use heating the adipose cells by radiofrequency waves. Alternatively the adipose cells may be heated by ultrasound waves or light. Further the shock waves may be applied to the body region to break large clusters to smaller clusters of adipose cells and/or improve the blood and/or lymph flow to prepare the treated body region for treatment by magnetic field. The following magnetic field may cause muscle contraction, metabolize released FFA. Finally, the shock waves may provide the massage effect for the treated body region for better regeneration and/or faster removing lactate and/or metabolic products.

The combined treatment may be applied for at least 10 seconds. Time duration of the combined treatment of the body region may be in the range of 1 to 240 minutes, more preferably in the range of 5 to 120 minutes, even more preferably 10 to 60 minutes, most preferably up to 30 minutes.

Each treatment method of the combined treatment, e.g. magnetic, mechanic or thermal treatment, may be applied immediately after a precedent treatment method, more preferably around 1 to 24 hours after the precedent treatment method, e.g. 1, 2, 8 or 20 hours after the precedent treatment method. The combined treatment may be applied periodically.

Alternatively, the combined treatment may be applied separately, e.g. treatments may alternate in appropriate periods. The period may last from 12 hours to 1 month, more preferably from 1 day to 2 weeks, most preferably from 3 days to 1 week.

All the recited methods may be applied to a patient in a non-invasive and/or contactless way. Therefore the present methods provide an effective alternative approach of enhancing the visual appearance with no need of invasive treatment or surgery. Further, the visual results are appreciable after several treatments. Additionally, the results include not only the visual appearance enhancement but even the improvement of the muscle structures, hence the patient feels firmer and tighter. The muscle structures become toned with no need of any diet or spending time by exercising in fitness.

The patient may feel firmer and/or tighter. The skin may be also tighter. Additionally, adipose tissue reduction may occur. Furthermore, cellulite may be reduced as well.

Alternatively the combined treatment may influence a sport performance. The combined treatment may be used for regeneration after sport performance and/or for recovering of the athletes after injuries by regenerating the muscles, improving local metabolism, preventing atrophy and/or by selective training of correct motion patterns. Hence a muscle memory and/or motion coordination of the athlete may be improved as well.

All the recited method may be combined together and may be provided in various sequences to treat various issues during one treatment. Furthermore each application may induce a plurality of treatment effect, e.g. adipose cell reduction, intramuscular fat decrease and/or reduction of cellulite.

Thus, novel systems and methods have been described. Various changes and substitutions may of course be made without departing from the spirit and scope of the invention. The invention, therefore, should not be limited, except by the following claims and their equivalents.

The following U.S. Patent Applications and their combinations with this patent application are incorporated herein by reference: Provisional U.S. Patent Application No. 62/357,679; Provisional U.S. Patent Application No. 62/587,716; U.S. patent application Ser. No. 15/678,915; U.S. patent application Ser. No. 15/786,303; U.S. patent application Ser. No. 15/478,943; U.S. patent application Ser. No. 15/471,946, now U.S. patent Ser. No. 10/080,906; U.S. patent application Ser. No. 16/134,116; U.S. patent application Ser. No. 15/584,747; U.S. patent application Ser. No. 16/205,401; U.S. patent application Ser. Nos. 16/218,735 and 16/217,724; U.S. patent application Ser. Nos. 16/196,798 and 16/196,837; U.S. patent application Ser. No. 16/042,093; U.S. patent application Ser. No. 15/344,811; U.S. patent application Ser. Nos. 16/034,752 and 16/034,793; U.S. patent application Ser. No. 15/954,783; U.S. patent application Ser. No. 15/862,410; U.S. patent application Ser. No. 15/860,443; U.S. patent application Ser. No. 15/677,371; U.S. patent application Ser. No. 15/446,951; U.S. patent application Ser. No. 15/396,073; U.S. patent application Ser. No. 15/178,455; U.S. patent application Ser. No. 15/151,012; U.S. patent application Ser. No. 15/099,274; U.S. patent application Ser. No. 15/073,318; U.S. patent application Ser. No. 14/951,093; U.S. patent application Ser. No. 14/926,365; U.S. patent application Ser. No. 14/789,156; U.S. patent application Ser. No. 14/789,658; U.S. patent application Ser. No. 15/601,719; U.S. patent application Ser. No. 15/473,390; U.S. patent application Ser. No. 15/404,384; U.S. patent application Ser. No. 16/194,800; Provisional U.S. Patent Application No. 62/440,912; Provisional U.S. Patent Application No. 62/440,936; Provisional U.S. Patent Application No. 62/440,940; and Provisional U.S. Patent Application No. 62/441,805; U.S. patent application Ser. No. 14/412,875.

All the above-listed applications are incorporated herein by reference in their entireties.

The invention claimed is:

1. A method for toning muscles of a patient using a treatment device that generates time-varying magnetic fields, the method comprising:
   charging a first energy storage device and a second energy storage device;
   discharging the first energy storage device to a first magnetic field generating coil disposed in a first applicator, and discharging the second energy storage device to a second magnetic field generating coil disposed in a second applicator;
   placing the first applicator and the second applicator in contact with the patient's skin or clothing at a body region, the body region comprising the patient's buttocks or abdomen;
   causing the first magnetic field generating coil to generate a first time-varying magnetic field, and simultaneously causing the second magnetic field generating coil to generate a second time-varying magnetic field, the first and second time-varying magnetic fields each having a magnetic flux density in a range of 0.5 to 7 Tesla at surfaces of the first and second magnetic field generating coils; and
   applying each of the first and second time-varying magnetic fields in trains of magnetic pulses to muscle fibers, neuromuscular plates, or nerves innervating muscle fibers in the body region, the magnetic pulses having a repetition rate in a range of 1 to 300 Hz, such that muscles of the body region are caused to contract.

2. The method of claim 1, further comprising:
   positioning the first applicator and the second applicator at the body region in mutually tilted planes defined by an angle.

3. The method of claim 1, further comprising:
   coupling the first and second applicators to the patient with an adjustable flexible belt, so that the belt holds the first and second applicator to the patient's skin or clothing.

4. The method of claim 3, wherein the coupling does not fix the first and second applicators in particular static positions during the treatment.

5. The method of claim 1, further comprising:
   positioning the first magnetic generating coil on the patient with reference to a visual marker on the first applicator, wherein the visual marker is aligned with the center of the first magnetic field generating coil; and positioning the second magnetic generating coil on the patient with reference to a visual marker on the second applicator, wherein the visual marker is aligned with the center of the second magnetic field generating coil.

6. The method of claim 1, further comprising:

assembling the magnetic pulses of the-time-varying magnetic fields in a trapezoidal envelope.

7. The method of claim 1, further comprising:

applying the first and second time-varying magnetic fields to cooperating muscles.

8. A method for toning muscles of a patient using a treatment device that generates time-varying magnetic fields, the method comprising:

placing a first applicator comprising a first magnetic field generating coil disposed in a casing in contact with the patient's skin or clothing;

placing a second applicator comprising a second magnetic field generating coil disposed in a casing in contact with the patient's skin or clothing;

attaching the first applicator and the second applicator to the patient's buttocks or abdomen with an adjustable flexible belt so that that the belt holds the first applicator and the second applicator to the patient's skin or clothing at the buttocks or abdomen;

generating simultaneous time-varying magnetic fields by the first and the second magnetic field generating coils; and applying pulses of the first and the second time-varying magnetic fields to a muscle group comprising one of a gluteus maximus, a gluteus medius, a gluteus minimus, a rectus abdominis, an abdominal internal oblique, an abdominal external oblique, a transverse abdominal, or a pyramidalis.

9. The method of claim 8, further comprising:

placing the first and the second applicators in contact with the patient's skin or clothing in a body region such that the time-varying magnetic fields are applied to muscle fibers, neuromuscular plates, or nerves innervating muscle fibers of cooperating muscles.

10. The method of claim 8, further comprising:

applying the time-varying magnetic fields to muscle fibers, neuromuscular plates, or nerves innervating muscle fibers such that an incomplete tetanus contraction is achieved in opposing sides of the patient's buttocks or abdomen.

11. The method of claim 10, further comprising:

applying the time-varying magnetic fields to peripheral nerves such that a complete tetanus contraction is achieved in opposing sides of the patient's buttocks or abdomen.

12. The method of claim 8, further comprising:

positioning the first and second applicators such that the centers of the magnetic field generating coils are spaced apart at a distance in a range of 15 cm to 40 cm during the treatment.

13. The method of claim 8, further comprising:

assembling pulses of the time-varying magnetic fields in a trapezoidal envelope.

14. The method of claim 8, further comprising:

initiating a treatment protocol using a touchscreen graphical user interface, wherein the treatment protocol comprises a set of predetermined treatment sequences having predetermined repetition rates applied for a predetermined time period.

15. A treatment device for toning muscles of a patient using time-varying magnetic fields, the treatment device comprising:

a control unit;

a first energy storage device;

a second energy storage device;

a first applicator, the first applicator comprising:
 a first casing; and
 a first magnetic field generating coil disposed within the first casing;

a first connecting tube coupling the first applicator to the control unit and to the first energy storage device;

a second applicator, the second applicator comprising:
 a second casing; and
 a second magnetic field generating coil disposed within the second casing; and a second connecting tube coupling the second applicator to the control unit and to the second energy storage device, wherein the treatment device is configured so that the first energy storage device can be discharged to the first magnetic field generating coil, and the second energy storage device can be discharged to the second magnetic field generating coil, wherein the first applicator and the second applicator are configured to be placed in contact with the patient's skin or clothing at a body region, the body region comprising the patient's buttocks or abdomen, wherein the treatment device is further configured so that the first and second magnetic field generating coils can each generate time-varying magnetic fields with magnetic flux densities in a range of 0.5 to 7 Tesla at surfaces of the first and second magnetic field coils, and wherein the treatment device is further configured so that the first and second time-varying magnetic fields can each be applied in trains of magnetic pulses to muscle fibers, neuromuscular plates, or nerves innervating muscle fibers in the body region, the magnetic pulses having a repetition rate in a range of 1 to 300 Hz, such that muscles of the body region are caused to contract.

16. The device of claim 15, wherein the treatment device is further configured so that the first and second energy storage devices can be discharged simultaneously.

17. The device of claim 15, further comprising:

a touchscreen graphical user interface coupled to the control unit, wherein the touchscreen graphical user interface is configured to enable an operator of the treatment device to cause discharge of the first and second energy storage devices.

18. The device of claim 15, wherein the treatment device is further configured to apply the time-varying magnetic fields to muscle fibers, neuromuscular plates, or nerves innervating muscle fibers such that a complete tetanus contraction is achieved in the patient's buttocks or abdomen.

19. The device of claim 15, wherein the first applicator further comprises a visual marker on the first casing, wherein the visual marker is aligned with the center of the first magnetic field generating coil, and wherein the second applicator further comprises a visual marker on the second casing, wherein the visual marker is aligned with the center of the second magnetic field generating coil.

20. The device of claim 15, wherein the control unit is configured to generate time-varying magnetic fields in a trapezoidal envelope during the treatment.

21. The device of claim 15, wherein each of the first and second applicators forms a concavity.

22. The device of claim 15, wherein a projection of an area of the first magnetic field generating coil is between 45 cm² and 450 cm², and wherein a projection of an area of the second magnetic field generating coil is between 45 cm² and 450 cm².

23. The device of claim 15, further comprising:

an adjustable flexible belt, wherein the adjustable flexible belt is configured to be coupled to both the first applicator and the second applicator so that that the belt holds the first applicator and the second applicator to the patient's skin or clothing at the buttocks or abdomen.

24. The device of claim 23, wherein each of the first and second applicators forms a concavity for receiving the belt.

25. The device of claim 23, wherein the belt does not fix the first and second applicators in particular static positions during the treatment.

26. The device of claim 15, the first applicator further comprising:

a handle formed on the upper side of the first casing; and the second applicator further comprising:

a handle formed on the upper side of the second casing.

27. The device of claim 15, the first applicator further comprising:

a visual marker aligned with the center of the first magnetic field generating coil to aid in positioning the first applicator by the operator; and the second applicator further comprising:

a visual marker aligned with the center of the second magnetic field generating coil to aid in positioning the second applicator by the operator.

28. The device of claim 15, wherein the treatment device does not include an adjustable positioning arm for supporting the first applicator or the second applicator during the treatment.

29. The device of claim 15, wherein the first connecting tube connects the first applicator to a source of fluid and the second connecting tube connects the second applicator to the source of fluid.

* * * * *